US012661133B2

(12) United States Patent
Perler et al.

(10) Patent No.: US 12,661,133 B2
(45) Date of Patent: *Jun. 23, 2026

(54) APPARATUS, SYSTEM, AND METHOD FOR PATIENT-SPECIFIC METHODS AND INSTRUMENTATION

(71) Applicant: Treace Medical Concepts, Inc., Ponte Vedra, FL (US)

(72) Inventors: Adam D. Perler, St. Petersburg, FL (US); James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 357 days.

This patent is subject to a terminal disclaimer.

(21) Appl. No.: 18/196,985

(22) Filed: May 12, 2023

(65) Prior Publication Data
US 2023/0363773 A1     Nov. 16, 2023

Related U.S. Application Data

(60) Provisional application No. 63/341,362, filed on May 12, 2022.

(51) Int. Cl.
*A61B 17/17* (2006.01)
*A61B 17/15* (2006.01)
(Continued)

(52) U.S. Cl.
CPC ........ *A61B 17/1775* (2016.11); *A61B 17/151* (2013.01); *A61B 17/56* (2013.01);
(Continued)

(58) Field of Classification Search
CPC ..... A61B 17/17; A61B 17/1775; A61B 17/15; A61B 17/151; A61B 17/152; A61B 17/56
See application file for complete search history.

(56) References Cited

U.S. PATENT DOCUMENTS

| 3,664,022 A | 5/1972 | Small |
| 4,069,824 A | 1/1978 | Weinstock |
| | (Continued) | |

FOREIGN PATENT DOCUMENTS

| AU | 2009227957 B2 | 7/2014 |
| AU | 2009222469 B2 | 2/2015 |
| | (Continued) | |

OTHER PUBLICATIONS

"Foot and Ankle Instrument Set," Smith & Nephew, 2013, 2 pages.
(Continued)

*Primary Examiner* — Christopher J Beccia
(74) *Attorney, Agent, or Firm* — Fredrikson & Byron, P.A.

(57) ABSTRACT

An apparatus, system, and method is disclosed for correcting a condition present in a patient. The apparatus may include a body having a superior side, an inferior side, a medial side, a lateral side, a proximal side, and a distal side. In addition, the apparatus may include a resection feature between a proximal end and a distal end that guides resection of a metatarsal of a patient's foot. Moreover, the apparatus may include a bone attachment feature configured to couple the body to the metatarsal. Also, the apparatus may include a bone engagement surface configured to register to the metatarsal based on medical imaging taken of the patient's foot.

19 Claims, 16 Drawing Sheets

(51) Int. Cl.
　　*A61B 17/56* 　　　(2006.01)
　　*G06T 7/00* 　　　(2017.01)
(52) U.S. Cl.
　　CPC ...... *G06T 7/0012* (2013.01); *A61B 2017/568*
　　　　　(2013.01); *G06T 2207/30008* (2013.01)

(56) References Cited

U.S. PATENT DOCUMENTS

| | | | |
|---|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,436,684 A | 3/1984 | White |
| 4,440,168 A | 4/1984 | Warren |
| 4,509,511 A | 4/1985 | Neufeld |
| 4,565,191 A | 1/1986 | Slocum |
| 4,570,624 A | 2/1986 | Wu |
| 4,628,919 A | 12/1986 | Clyburn |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,839,822 A | 6/1989 | Dormond et al. |
| 4,895,141 A | 1/1990 | Koeneman et al. |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,049,149 A | 9/1991 | Schmidt |
| 5,053,039 A | 10/1991 | Hofmann et al. |
| 5,112,334 A | 5/1992 | Alchermes et al. |
| 5,147,364 A | 9/1992 | Comparetto |
| 5,171,244 A | 12/1992 | Caspari et al. |
| 5,176,685 A | 1/1993 | Rayhack |
| 5,207,676 A | 5/1993 | Canadell et al. |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,643,270 A | 7/1997 | Combs |
| 5,662,656 A | 9/1997 | White |
| 5,667,510 A | 9/1997 | Combs |
| H1706 H | 1/1998 | Mason |
| 5,722,978 A | 3/1998 | Jenkins, Jr. |
| 5,749,875 A | 5/1998 | Puddu |
| 5,779,709 A | 7/1998 | Harris, Jr. et al. |
| 5,788,695 A | 8/1998 | Richardson |
| 5,803,924 A | 9/1998 | Oni et al. |
| 5,810,822 A | 9/1998 | Mortier |
| 5,836,950 A | 11/1998 | Hansson |
| 5,839,438 A | 11/1998 | Graettinger et al. |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,957,927 A | 9/1999 | Magee et al. |
| 5,980,526 A | 11/1999 | Johnson et al. |
| 5,984,931 A | 11/1999 | Greenfield |
| 6,007,535 A | 12/1999 | Rayhack et al. |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | Von Hoffmann et al. |
| 6,676,662 B1 | 1/2004 | Bagga et al. |
| 6,712,824 B2 | 3/2004 | Millard et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,780,190 B2 | 8/2004 | Maroney |
| 6,796,986 B2 | 9/2004 | Duffner |
| 6,859,661 B2 | 2/2005 | Tuke |
| 6,944,518 B2 | 9/2005 | Roose |
| 6,964,645 B1 | 11/2005 | Smits |
| 7,033,361 B2 | 4/2006 | Collazo |
| 7,097,647 B2 | 8/2006 | Segler |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,351,203 B2 | 4/2008 | Jelliffe et al. |
| 7,377,924 B2 | 5/2008 | Raistrick et al. |
| 7,465,303 B2 | 12/2008 | Riccione et al. |
| 7,473,255 B2 | 1/2009 | Mcgarity et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,670,345 B2 | 3/2010 | Plassky et al. |
| 7,686,811 B2 | 3/2010 | Byrd et al. |
| 7,691,108 B2 | 4/2010 | Lavallee |
| 7,763,026 B2 | 7/2010 | Egger et al. |
| 7,789,885 B2 | 9/2010 | Metzger |
| D629,900 S | 12/2010 | Fisher |
| 7,875,058 B2 | 1/2011 | Holmes, Jr. |
| 7,972,338 B2 | 7/2011 | O'Brien |
| 7,983,777 B2 | 7/2011 | Melton et al. |
| D646,389 S | 10/2011 | Claypool et al. |
| 8,057,473 B2 | 11/2011 | Orsak et al. |
| 8,057,478 B2 | 11/2011 | Kuczynski et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton |
| 8,083,746 B2 | 12/2011 | Novak |
| 8,114,087 B2 | 2/2012 | Long et al. |
| 8,123,753 B2 | 2/2012 | Poncet |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,187,280 B2 | 5/2012 | May et al. |
| 8,192,441 B2 | 6/2012 | Collazo |
| 8,197,487 B2 | 6/2012 | Poncet et al. |
| 8,206,153 B2 | 6/2012 | Suttin et al. |
| 8,231,623 B1 | 7/2012 | Jordan |
| 8,231,663 B2 | 7/2012 | Kay et al. |
| 8,246,561 B1 | 8/2012 | Agee et al. |
| 8,246,680 B2 | 8/2012 | Betz et al. |
| D666,721 S | 9/2012 | Wright et al. |
| 8,262,664 B2 | 9/2012 | Justin et al. |
| 8,262,665 B2 | 9/2012 | Massoud |
| 8,277,455 B2 | 10/2012 | Couture et al. |
| 8,282,644 B2 | 10/2012 | Edwards |
| 8,282,645 B2 | 10/2012 | Lawrence et al. |
| 8,287,541 B2 | 10/2012 | Nelson et al. |
| 8,292,966 B2 | 10/2012 | Morton |
| 8,303,596 B2 | 11/2012 | Plaky et al. |
| 8,323,281 B2 | 12/2012 | Hotchkiss et al. |
| 8,323,289 B2 | 12/2012 | Re |
| 8,357,111 B2 | 1/2013 | Caillouette et al. |
| 8,377,105 B2 | 2/2013 | Bscher |
| 8,388,690 B2 | 3/2013 | Singhatat et al. |
| D679,395 S | 4/2013 | Wright et al. |
| 8,435,246 B2 | 5/2013 | Fisher et al. |

(56)            References Cited

U.S. PATENT DOCUMENTS

| | | | |
|---|---|---|---|
| 8,475,462 | B2 | 7/2013 | Thomas et al. |
| 8,484,001 | B2 | 7/2013 | Glozman et al. |
| 8,518,045 | B2 | 8/2013 | Szanto |
| 8,523,870 | B2 | 9/2013 | Green et al. |
| 8,529,568 | B2 | 9/2013 | Bouadi |
| 8,532,807 | B2 | 9/2013 | Metzger |
| 8,551,106 | B2 | 10/2013 | Harrold |
| D694,884 | S | 12/2013 | Mooradian et al. |
| D695,402 | S | 12/2013 | Dacosta et al. |
| 8,641,721 | B2 | 2/2014 | Aram et al. |
| 8,652,142 | B2 | 2/2014 | Geissler |
| 8,657,820 | B2 | 2/2014 | Kubiak et al. |
| D701,303 | S | 3/2014 | Cook |
| 8,663,234 | B2 | 3/2014 | Grimm et al. |
| 8,668,700 | B2 | 3/2014 | Catanzarite et al. |
| 8,685,030 | B2 | 4/2014 | Gtte et al. |
| 8,696,719 | B2 | 4/2014 | Lofthouse et al. |
| 8,702,686 | B2 | 4/2014 | Geebelen et al. |
| 8,702,712 | B2 | 4/2014 | Jordan et al. |
| 8,715,289 | B2 | 5/2014 | Smith |
| 8,715,363 | B2 | 5/2014 | Ratron et al. |
| 8,728,084 | B2 | 5/2014 | Berelsman et al. |
| 8,758,354 | B2 | 6/2014 | Habegger et al. |
| 8,777,948 | B2 | 7/2014 | Bernsteiner |
| 8,784,457 | B2 | 7/2014 | Graham |
| 8,795,286 | B2 | 8/2014 | Sand et al. |
| 8,808,298 | B2 | 8/2014 | Raub et al. |
| 8,808,301 | B1 | 8/2014 | Nofsinger |
| 8,808,302 | B2 | 8/2014 | Roose et al. |
| 8,828,012 | B2 | 9/2014 | May et al. |
| 8,838,263 | B2 | 9/2014 | Sivak et al. |
| 8,858,602 | B2 | 10/2014 | Weiner et al. |
| 8,864,773 | B2 | 10/2014 | Paul et al. |
| 8,882,778 | B2 | 11/2014 | Ranft |
| 8,882,816 | B2 | 11/2014 | Kartalian et al. |
| 8,892,235 | B2 | 11/2014 | Choi et al. |
| 8,898,043 | B2 | 11/2014 | Ashby et al. |
| D720,456 | S | 12/2014 | Dacosta et al. |
| 8,900,247 | B2 | 12/2014 | Tseng et al. |
| 8,911,444 | B2 | 12/2014 | Bailey |
| 8,920,428 | B2 | 12/2014 | Zakaria et al. |
| 8,926,612 | B2 | 1/2015 | Graham |
| 8,932,299 | B2 | 1/2015 | Bono et al. |
| 8,939,982 | B2 | 1/2015 | Chellaoui |
| 8,939,984 | B2 | 1/2015 | Budoff |
| 8,945,132 | B2 | 2/2015 | Play et al. |
| 8,965,075 | B2 | 2/2015 | Arnaud et al. |
| 8,974,460 | B2 | 3/2015 | De La Fuente et al. |
| 8,979,856 | B2 | 3/2015 | Catanzarite et al. |
| 8,992,531 | B2 | 3/2015 | Chow et al. |
| 8,992,532 | B2 | 3/2015 | Wong |
| 8,998,903 | B2 | 4/2015 | Price et al. |
| 8,998,904 | B2 | 4/2015 | Zeetser et al. |
| 8,998,907 | B2 | 4/2015 | Myers |
| 8,998,909 | B2 | 4/2015 | Gillman et al. |
| 9,005,207 | B2 | 4/2015 | Dodds et al. |
| 9,011,451 | B2 | 4/2015 | Long et al. |
| 9,011,452 | B2 | 4/2015 | Iannotti et al. |
| 9,011,456 | B2 | 4/2015 | Ranawat et al. |
| 9,014,835 | B2 | 4/2015 | Azernikov et al. |
| 9,017,329 | B2 | 4/2015 | Tyber et al. |
| 9,017,336 | B2 | 4/2015 | Park et al. |
| 9,023,052 | B2 | 5/2015 | Lietz et al. |
| 9,044,250 | B2 | 6/2015 | Olsen et al. |
| 9,060,788 | B2 | 6/2015 | Bollinger |
| 9,060,822 | B2 | 6/2015 | Wright et al. |
| 9,089,376 | B2 | 7/2015 | Medoff et al. |
| 9,101,421 | B2 | 8/2015 | Blacklidge |
| 9,107,715 | B2 | 8/2015 | Blitz et al. |
| 9,113,915 | B2 | 8/2015 | Thomas et al. |
| 9,113,957 | B2 | 8/2015 | Axelson, Jr. et al. |
| 9,138,237 | B2 | 9/2015 | Meade et al. |
| 9,138,332 | B2 | 9/2015 | Harris et al. |
| D740,424 | S | 10/2015 | Dacosta et al. |
| 9,173,665 | B2 | 11/2015 | Couture |
| 9,173,691 | B2 | 11/2015 | Orbay et al. |
| 9,186,154 | B2 | 11/2015 | Li |
| 9,186,160 | B1 | 11/2015 | Song |
| 9,198,678 | B2 | 12/2015 | Frey et al. |
| 9,204,897 | B2 | 12/2015 | Jones et al. |
| 9,211,128 | B2 | 12/2015 | Gillman et al. |
| 9,220,509 | B2 | 12/2015 | Boyer et al. |
| 9,220,518 | B2 | 12/2015 | Neal et al. |
| 9,220,519 | B2 | 12/2015 | Kaneyama et al. |
| 9,220,551 | B2 | 12/2015 | Waizenegger |
| 9,232,951 | B2 | 1/2016 | Johannaber |
| 9,232,955 | B2 | 1/2016 | Bonin, Jr. et al. |
| 9,254,155 | B2 | 2/2016 | Iannotti et al. |
| 9,295,497 | B2 | 3/2016 | Schoenefeld et al. |
| 9,301,768 | B2 | 4/2016 | Buza et al. |
| 9,301,783 | B2 | 4/2016 | Gerold et al. |
| 9,308,006 | B2 | 4/2016 | Martin et al. |
| 9,308,037 | B2 | 4/2016 | Richter et al. |
| 9,320,609 | B2 | 4/2016 | Schon et al. |
| 9,345,497 | B2 | 5/2016 | Gonzalvez et al. |
| 9,351,738 | B2 | 5/2016 | Aram et al. |
| 9,351,743 | B2 | 5/2016 | Kehres et al. |
| 9,370,380 | B2 | 6/2016 | Riccione |
| 9,375,220 | B2 | 6/2016 | Horan et al. |
| 9,402,636 | B2 | 8/2016 | Collazo |
| 9,402,640 | B2 | 8/2016 | Reynolds et al. |
| 9,408,641 | B2 | 8/2016 | Zhang et al. |
| 9,414,846 | B2 | 8/2016 | Gillman et al. |
| 9,414,847 | B2 | 8/2016 | Kurtz |
| 9,414,877 | B2 | 8/2016 | Helenbolt et al. |
| 9,421,021 | B2 | 8/2016 | Keppler |
| 9,427,240 | B2 | 8/2016 | Von Zabern et al. |
| D765,844 | S | 9/2016 | Dacosta |
| D766,434 | S | 9/2016 | Dacosta |
| D766,437 | S | 9/2016 | Dacosta |
| D766,438 | S | 9/2016 | Dacosta |
| D766,439 | S | 9/2016 | Dacosta |
| 9,433,452 | B2 | 9/2016 | Weiner et al. |
| 9,445,823 | B2 | 9/2016 | Harris et al. |
| 9,452,050 | B2 | 9/2016 | Miles et al. |
| 9,456,902 | B2 | 10/2016 | Hacking et al. |
| 9,463,034 | B2 | 10/2016 | Wong et al. |
| 9,492,182 | B2 | 11/2016 | Keefer |
| 9,517,145 | B2 | 12/2016 | Meridew et al. |
| 9,522,023 | B2 | 12/2016 | Haddad et al. |
| 9,526,514 | B2 | 12/2016 | Kelley et al. |
| 9,545,276 | B2 | 1/2017 | Buchanan et al. |
| 9,561,041 | B2 | 2/2017 | Snider et al. |
| 9,566,103 | B2 | 2/2017 | Mayer |
| 9,579,106 | B2 | 2/2017 | Lo et al. |
| 9,579,107 | B2 | 2/2017 | Schoenefeld |
| 9,579,112 | B2 | 2/2017 | Catanzarite et al. |
| 9,592,084 | B2 | 3/2017 | Grant |
| 9,603,605 | B2 | 3/2017 | Collazo |
| 9,603,640 | B2 | 3/2017 | Palmer et al. |
| 9,622,820 | B2 | 4/2017 | Baloch et al. |
| 9,629,726 | B2 | 4/2017 | Reiley et al. |
| 9,652,889 | B2 | 5/2017 | Young et al. |
| 9,662,220 | B2 | 5/2017 | Warburton |
| 9,668,746 | B2 | 6/2017 | Lee et al. |
| 9,675,471 | B2 | 6/2017 | Bojarski et al. |
| 9,687,261 | B2 | 6/2017 | Serbousek et al. |
| 9,693,787 | B2 | 7/2017 | Ammann et al. |
| 9,693,878 | B2 | 7/2017 | Kunz et al. |
| 9,700,433 | B2 | 7/2017 | Myers |
| 9,713,484 | B2 | 7/2017 | Sammarco |
| 9,737,311 | B2 | 8/2017 | Lavallee et al. |
| 9,737,367 | B2 | 8/2017 | Steines et al. |
| 9,750,538 | B2 | 9/2017 | Soffiatti et al. |
| 9,785,747 | B2 | 10/2017 | Geebelen |
| 9,788,958 | B2 | 10/2017 | Melamed et al. |
| 9,788,975 | B2 | 10/2017 | Li |
| 9,795,392 | B2 | 10/2017 | Zajac |
| 9,795,394 | B2 | 10/2017 | Bonutti |
| 9,814,474 | B2 | 11/2017 | Montoya et al. |
| 9,820,868 | B2 | 11/2017 | Witt et al. |
| 9,826,981 | B2 | 11/2017 | Schoenefeld et al. |
| 9,839,438 | B2 | 12/2017 | Eash |
| 9,848,929 | B2 | 12/2017 | Dacosta et al. |

(56) References Cited

U.S. PATENT DOCUMENTS

| | | | |
|---|---|---|---|
| 9,849,019 | B2 | 12/2017 | Miller et al. |
| 9,877,754 | B2 | 1/2018 | Patel et al. |
| 9,883,954 | B1 | 2/2018 | Murphy |
| 9,888,931 | B2 | 2/2018 | Bake |
| 9,888,950 | B2 | 2/2018 | Perez et al. |
| 9,918,658 | B2 | 3/2018 | Mccaulley et al. |
| 9,918,769 | B2 | 3/2018 | Provencher et al. |
| 9,925,049 | B2 | 3/2018 | Goldstein et al. |
| 9,925,068 | B2 | 3/2018 | Bays et al. |
| 9,956,089 | B2 | 5/2018 | Kelman et al. |
| 9,968,456 | B2 | 5/2018 | Song |
| 9,980,760 | B2 | 5/2018 | Dacosta et al. |
| 9,987,092 | B2 | 6/2018 | Hladio et al. |
| 9,990,765 | B2 | 6/2018 | Ju et al. |
| 9,993,256 | B2 | 6/2018 | Lipman et al. |
| 10,002,227 | B2 | 6/2018 | Netravali et al. |
| 10,004,516 | B2 | 6/2018 | Johannaber |
| 10,010,431 | B2 | 7/2018 | Eraly et al. |
| 10,016,177 | B2 | 7/2018 | Aram et al. |
| 10,022,170 | B2 | 7/2018 | Leemrijse et al. |
| 10,028,756 | B2 | 7/2018 | Liu |
| 10,034,753 | B2 | 7/2018 | Dressler et al. |
| 10,052,114 | B2 | 8/2018 | Keppler et al. |
| 10,055,536 | B2 | 8/2018 | Maes et al. |
| 10,058,335 | B2 | 8/2018 | Lee et al. |
| 10,089,413 | B2 | 10/2018 | Wirx-Speetjens et al. |
| 10,098,761 | B2 | 10/2018 | Sherman et al. |
| 10,105,145 | B2 | 10/2018 | Lavallee |
| 10,123,807 | B2 | 11/2018 | Geebelen |
| 10,130,378 | B2 | 11/2018 | Bryan |
| 10,149,722 | B2 | 12/2018 | Aram et al. |
| 10,159,480 | B2 | 12/2018 | Tuten |
| 10,159,499 | B2 | 12/2018 | Dacosta et al. |
| 10,159,512 | B2 | 12/2018 | Robinson |
| 10,201,357 | B2 | 2/2019 | Aram et al. |
| 10,206,692 | B2 | 2/2019 | Sanders |
| 10,217,530 | B2 | 2/2019 | Couture et al. |
| 10,219,812 | B2 | 3/2019 | Torrie et al. |
| 10,226,292 | B2 | 3/2019 | Lundquist et al. |
| 10,231,745 | B2 | 3/2019 | Geebelen et al. |
| 10,238,382 | B2 | 3/2019 | Terrill et al. |
| 10,251,654 | B2 | 4/2019 | Fritzinger |
| 10,251,690 | B2 | 4/2019 | Katrana et al. |
| 10,262,084 | B2 | 4/2019 | Lavallee et al. |
| 10,265,080 | B2 | 4/2019 | Hughes et al. |
| 10,271,886 | B2 | 4/2019 | Abiven |
| 10,278,713 | B2 | 5/2019 | Richter et al. |
| 10,282,488 | B2 | 5/2019 | Eash |
| 10,286,197 | B2 | 5/2019 | Pouliot et al. |
| 10,325,065 | B2 | 6/2019 | Li et al. |
| 10,327,829 | B2 | 6/2019 | Dacosta et al. |
| 10,342,529 | B2 | 7/2019 | Fallin et al. |
| 10,350,022 | B2 | 7/2019 | Jansen et al. |
| 10,357,261 | B2 | 7/2019 | Kugler et al. |
| 10,357,299 | B2 | 7/2019 | Weiner et al. |
| 10,363,052 | B2 | 7/2019 | Park et al. |
| 10,376,268 | B2 | 8/2019 | Fallin et al. |
| 10,398,510 | B2 | 9/2019 | Goto |
| 10,420,613 | B2 | 9/2019 | Azevedo Da Silva et al. |
| 10,456,205 | B2 | 10/2019 | Meridew et al. |
| 10,512,470 | B1 | 12/2019 | Bays et al. |
| 10,524,808 | B1 | 1/2020 | Hissong et al. |
| 10,524,845 | B2 | 1/2020 | Orsak et al. |
| 10,537,392 | B2 | 1/2020 | Millahn et al. |
| 10,543,100 | B2 | 1/2020 | Couture et al. |
| 10,548,667 | B2 | 2/2020 | Flett et al. |
| 10,548,668 | B2 | 2/2020 | Furrer et al. |
| 10,575,862 | B2 | 3/2020 | Bays et al. |
| 10,582,969 | B2 | 3/2020 | Couture et al. |
| 10,610,241 | B2 | 4/2020 | Wagner et al. |
| 10,631,878 | B2 | 4/2020 | Fritzinger |
| 10,631,902 | B2 | 4/2020 | Weiner et al. |
| 10,653,432 | B2 | 5/2020 | Luttrell et al. |
| 10,653,464 | B2 | 5/2020 | Hill et al. |
| 10,653,467 | B2 | 5/2020 | Brumfield et al. |
| 10,675,096 | B2 | 6/2020 | Utz et al. |
| 10,682,147 | B2 | 6/2020 | Grant et al. |
| 10,709,567 | B2 | 7/2020 | Welker et al. |
| 10,716,581 | B2 | 7/2020 | Fritzinger et al. |
| 10,722,309 | B2 | 7/2020 | Gillman |
| 10,722,310 | B2 | 7/2020 | Luby |
| 10,779,867 | B2 | 9/2020 | Penzimer et al. |
| 10,779,890 | B2 | 9/2020 | Weir |
| 10,786,291 | B2 | 9/2020 | Weiner et al. |
| 10,792,081 | B2 | 10/2020 | Weiner et al. |
| 10,806,469 | B2 | 10/2020 | Fiechter et al. |
| 10,849,665 | B2 | 12/2020 | Singh et al. |
| 10,849,670 | B2 | 12/2020 | Santrock et al. |
| 10,856,891 | B2 | 12/2020 | Rhodes et al. |
| 10,856,925 | B1 | 12/2020 | Pontell |
| 10,869,722 | B2 | 12/2020 | Caldwell et al. |
| 10,874,408 | B2 | 12/2020 | Couture |
| 10,881,416 | B2 | 1/2021 | Couture et al. |
| 10,881,417 | B2 | 1/2021 | Mahfouz |
| 10,888,340 | B2 | 1/2021 | Awtrey et al. |
| 10,898,211 | B2 | 1/2021 | Fallin et al. |
| 10,905,444 | B2 | 2/2021 | Siccardi et al. |
| 10,912,574 | B2 | 2/2021 | Kim et al. |
| 10,925,622 | B2 | 2/2021 | Kehres et al. |
| 10,939,926 | B2 | 3/2021 | Kam et al. |
| 10,939,939 | B1 | 3/2021 | Gil et al. |
| 10,973,529 | B2 | 4/2021 | Lavallee et al. |
| 11,000,327 | B2 | 5/2021 | Schlotterback et al. |
| 11,020,128 | B2 | 6/2021 | Guilloux et al. |
| 11,033,336 | B2 | 6/2021 | Bohl |
| 11,058,546 | B2 | 7/2021 | Hollis et al. |
| 11,065,011 | B2 | 7/2021 | Bake et al. |
| 11,074,688 | B2 | 7/2021 | Chabin et al. |
| 11,090,069 | B2 | 8/2021 | Park |
| 11,090,161 | B2 | 8/2021 | Hodorek |
| 11,112,770 | B2 | 9/2021 | Roh et al. |
| 11,116,518 | B2 | 9/2021 | Hafez |
| 11,129,625 | B2 | 9/2021 | Song et al. |
| 11,129,678 | B2 | 9/2021 | Park |
| 11,154,362 | B2 | 10/2021 | Kim et al. |
| 11,158,047 | B2 | 10/2021 | Shah |
| 11,160,567 | B2 | 11/2021 | Fallin et al. |
| 11,160,568 | B1 | 11/2021 | Park |
| 11,166,732 | B2 | 11/2021 | Maxson et al. |
| 11,172,945 | B1 | 11/2021 | Lian |
| 11,179,165 | B2 | 11/2021 | Schoenefeld |
| 11,179,168 | B2 | 11/2021 | Dacosta et al. |
| 11,207,134 | B2 | 12/2021 | Hafez |
| 11,213,305 | B2 | 1/2022 | Iannotti et al. |
| 11,213,406 | B2 | 1/2022 | Rodriguez et al. |
| 11,219,526 | B2 | 1/2022 | Mahfouz |
| 11,224,448 | B2 | 1/2022 | Bailey |
| 11,259,817 | B2 | 3/2022 | Fallin et al. |
| 11,259,874 | B1 | 3/2022 | Landon et al. |
| 11,284,909 | B2 | 3/2022 | Castricini et al. |
| 11,304,705 | B2 | 4/2022 | Fallin et al. |
| 11,304,735 | B2 | 4/2022 | Sayger et al. |
| 11,324,522 | B2 | 5/2022 | Metzger et al. |
| 11,324,607 | B2 | 5/2022 | Mauldin et al. |
| 11,331,148 | B2 | 5/2022 | Fritzinger |
| 11,331,205 | B2 | 5/2022 | Parr |
| 11,344,347 | B2 | 5/2022 | Treace et al. |
| 11,389,221 | B2 | 7/2022 | Tyber et al. |
| 11,399,849 | B2 | 8/2022 | Larche et al. |
| 11,419,726 | B2 | 8/2022 | Miller et al. |
| 11,426,184 | B2 | 8/2022 | Rivet-Sabourin et al. |
| 11,432,931 | B2 | 9/2022 | Lang |
| 11,436,801 | B2 | 9/2022 | Haslam et al. |
| 11,439,412 | B2 | 9/2022 | Woodard et al. |
| 11,457,980 | B2 | 10/2022 | Bonny et al. |
| 11,484,354 | B2 | 11/2022 | Singh et al. |
| 11,497,557 | B2 | 11/2022 | Haslam et al. |
| 11,508,102 | B2 | 11/2022 | Su et al. |
| 11,510,738 | B2 | 11/2022 | Stifter et al. |
| 11,532,402 | B2 | 12/2022 | Farley et al. |
| 11,557,036 | B2 | 1/2023 | Mansi et al. |
| 11,583,298 | B2 | 2/2023 | Robichaud et al. |
| 11,596,421 | B2 | 3/2023 | Saltzman et al. |
| 11,596,443 | B2 | 3/2023 | Treace et al. |

(56) References Cited

U.S. PATENT DOCUMENTS

| | | | |
|---|---|---|---|
| 11,602,386 B2 | 3/2023 | Smith et al. | |
| 11,607,250 B2 | 3/2023 | Treace et al. | |
| 11,627,954 B2 | 4/2023 | May et al. | |
| 11,628,003 B2 | 4/2023 | Nachtrab et al. | |
| 11,633,195 B2 | 4/2023 | Dhillon | |
| 11,648,019 B2 | 5/2023 | Bays et al. | |
| 11,653,938 B2 | 5/2023 | Siegler | |
| 11,684,423 B2 | 6/2023 | Jaramaz et al. | |
| 11,690,725 B2 | 7/2023 | Gemon et al. | |
| 11,717,359 B2 | 8/2023 | Chi | |
| 11,741,277 B2 | 8/2023 | Dayal et al. | |
| 11,751,892 B2 | 9/2023 | Woodard et al. | |
| 11,756,051 B2 | 9/2023 | Indani et al. | |
| 11,766,268 B2 | 9/2023 | Iannotti et al. | |
| 11,779,467 B2 | 10/2023 | Mimnaugh et al. | |
| 11,786,257 B2 | 10/2023 | Dayton et al. | |
| 11,793,549 B2 | 10/2023 | Rhodes et al. | |
| 11,812,978 B2 | 11/2023 | Trabish et al. | |
| 11,819,223 B2 | 11/2023 | Lee | |
| 11,819,224 B2 | 11/2023 | Allard et al. | |
| 11,849,933 B2 | 12/2023 | Denham et al. | |
| 11,849,957 B2 | 12/2023 | Couture et al. | |
| 11,849,961 B2 | 12/2023 | Khatibi et al. | |
| 11,849,962 B2 | 12/2023 | Singh et al. | |
| 11,854,683 B2 | 12/2023 | Casey et al. | |
| D1,011,524 S | 1/2024 | Santrock et al. | |
| 11,857,206 B2 | 1/2024 | Robichaud et al. | |
| 11,864,778 B2 | 1/2024 | Mcginley et al. | |
| 11,864,959 B2 | 1/2024 | Basta | |
| 11,911,046 B2 | 2/2024 | Carroll et al. | |
| 11,925,417 B2 | 3/2024 | Mosnier et al. | |
| 11,931,106 B2 | 3/2024 | Perler et al. | |
| 11,944,546 B2 | 4/2024 | Puncreobutr et al. | |
| 11,950,786 B2 | 4/2024 | Courtis et al. | |
| 11,963,687 B2 | 4/2024 | Langhorn et al. | |
| 11,963,703 B2 | 4/2024 | Dayton et al. | |
| 11,963,729 B2 | 4/2024 | Aljuri et al. | |
| 11,980,377 B2 | 5/2024 | Mauldin et al. | |
| 11,986,251 B2 * | 5/2024 | Perler | A61B 17/8095 |
| 12,004,789 B2 | 6/2024 | Mcaleer et al. | |
| 12,004,814 B2 | 6/2024 | Ryan et al. | |
| D1,034,985 S | 7/2024 | Hartson et al. | |
| 12,035,929 B2 | 7/2024 | Athwal et al. | |
| 12,045,943 B2 | 7/2024 | Chaoui et al. | |
| 12,048,600 B2 | 7/2024 | Azernikov et al. | |
| 12,050,999 B2 | 7/2024 | Poltaretskyi et al. | |
| 12,053,242 B2 | 8/2024 | Landon et al. | |
| 12,062,183 B2 | 8/2024 | Chaoui et al. | |
| 12,097,129 B2 | 9/2024 | Deransart et al. | |
| 12,115,083 B2 | 10/2024 | Mullen et al. | |
| 12,121,272 B2 | 10/2024 | Marien et al. | |
| 2002/0107519 A1 | 8/2002 | Dixon et al. | |
| 2003/0236522 A1 | 12/2003 | Long et al. | |
| 2004/0010259 A1 | 1/2004 | Keller et al. | |
| 2004/0039394 A1 | 2/2004 | Conti et al. | |
| 2004/0039396 A1 | 2/2004 | Couture et al. | |
| 2004/0097946 A1 | 5/2004 | Dietzel et al. | |
| 2004/0138669 A1 | 7/2004 | Horn | |
| 2005/0059978 A1 | 3/2005 | Sherry et al. | |
| 2005/0080424 A1 | 4/2005 | Cuckler et al. | |
| 2005/0267482 A1 | 12/2005 | Hyde | |
| 2005/0273112 A1 | 12/2005 | Mcnamara | |
| 2006/0129163 A1 | 6/2006 | Mcguire | |
| 2006/0206044 A1 | 9/2006 | Simon | |
| 2006/0229621 A1 | 10/2006 | Cadmus | |
| 2006/0241607 A1 | 10/2006 | Myerson et al. | |
| 2006/0241608 A1 | 10/2006 | Myerson et al. | |
| 2006/0264961 A1 | 11/2006 | Murray-Brown | |
| 2007/0010818 A1 | 1/2007 | Stone et al. | |
| 2007/0123857 A1 | 5/2007 | Deffenbaugh et al. | |
| 2007/0233138 A1 | 10/2007 | Figueroa et al. | |
| 2007/0265634 A1 | 11/2007 | Weinstein | |
| 2007/0276383 A1 | 11/2007 | Rayhack | |
| 2008/0009863 A1 | 1/2008 | Bond et al. | |
| 2008/0039850 A1 | 2/2008 | Rowley et al. | |
| 2008/0091197 A1 | 4/2008 | Coughlin | |
| 2008/0140081 A1 | 6/2008 | Heavener et al. | |
| 2008/0161815 A1 | 7/2008 | Schoenefeld et al. | |
| 2008/0172054 A1 | 7/2008 | Claypool et al. | |
| 2008/0288004 A1 | 11/2008 | Schendel | |
| 2009/0036931 A1 | 2/2009 | Pech et al. | |
| 2009/0089081 A1 | 4/2009 | Haddad | |
| 2009/0093849 A1 | 4/2009 | Grabowski | |
| 2009/0105767 A1 | 4/2009 | Reiley | |
| 2009/0198244 A1 | 8/2009 | Leibel | |
| 2009/0216089 A1 | 8/2009 | Davidson | |
| 2009/0222047 A1 | 9/2009 | Graham | |
| 2009/0254092 A1 | 10/2009 | Albiol Llorach | |
| 2009/0254126 A1 | 10/2009 | Orbay et al. | |
| 2009/0265012 A1 | 10/2009 | Engh et al. | |
| 2009/0287309 A1 | 11/2009 | Walch et al. | |
| 2010/0069910 A1 | 3/2010 | Hasselman | |
| 2010/0130981 A1 | 5/2010 | Richards | |
| 2010/0168799 A1 | 7/2010 | Schumer | |
| 2010/0185202 A1 | 7/2010 | Lester et al. | |
| 2010/0217270 A1 | 8/2010 | Polinski et al. | |
| 2010/0256687 A1 | 10/2010 | Neufeld et al. | |
| 2010/0274253 A1 | 10/2010 | Ure | |
| 2010/0318088 A1 | 12/2010 | Warne et al. | |
| 2011/0009865 A1 | 1/2011 | Orfaly | |
| 2012/0065689 A1 | 3/2012 | Prasad et al. | |
| 2012/0116203 A1 | 5/2012 | Vancraen et al. | |
| 2012/0123420 A1 | 5/2012 | Honiball | |
| 2012/0130434 A1 | 5/2012 | Stemniski | |
| 2012/0150242 A1 | 6/2012 | Mannion | |
| 2012/0191199 A1 | 7/2012 | Raemisch | |
| 2012/0234329 A1 | 9/2012 | Vancraen et al. | |
| 2012/0253350 A1 | 10/2012 | Anthony et al. | |
| 2012/0265301 A1 | 10/2012 | Demers et al. | |
| 2012/0277745 A1 | 11/2012 | Lizee | |
| 2013/0211410 A1 | 8/2013 | Landes et al. | |
| 2013/0236874 A1 | 9/2013 | Iannotti et al. | |
| 2013/0237989 A1 | 9/2013 | Bonutti | |
| 2013/0274778 A1 | 10/2013 | Mercier et al. | |
| 2013/0289570 A1 | 10/2013 | Chao | |
| 2013/0292870 A1 | 11/2013 | Roger | |
| 2014/0005672 A1 | 1/2014 | Edwards et al. | |
| 2014/0039501 A1 | 2/2014 | Schickendantz et al. | |
| 2014/0074099 A1 | 3/2014 | Vigneron et al. | |
| 2014/0094861 A1 | 4/2014 | Fallin | |
| 2014/0163568 A1 | 6/2014 | Wong et al. | |
| 2014/0257402 A1 | 9/2014 | Barsoum | |
| 2014/0259629 A1 | 9/2014 | Dion et al. | |
| 2014/0263674 A1 | 9/2014 | Cerveny | |
| 2014/0343555 A1 | 11/2014 | Russi et al. | |
| 2014/0371866 A1 | 12/2014 | Chao et al. | |
| 2014/0371897 A1 | 12/2014 | Lin et al. | |
| 2015/0032215 A1 | 1/2015 | Slamin et al. | |
| 2015/0045903 A1 | 2/2015 | Neal | |
| 2015/0066094 A1 | 3/2015 | Anderson et al. | |
| 2015/0081029 A1 | 3/2015 | Bojarski et al. | |
| 2015/0088142 A1 | 3/2015 | Gibson | |
| 2015/0093283 A1 | 4/2015 | Miller et al. | |
| 2015/0112348 A1 | 4/2015 | Schoenefeld et al. | |
| 2015/0142000 A1 | 5/2015 | Seedhom et al. | |
| 2015/0182342 A1 | 7/2015 | Hafez | |
| 2015/0227679 A1 | 8/2015 | Kamer et al. | |
| 2015/0230843 A1 | 8/2015 | Palmer et al. | |
| 2015/0305752 A1 | 10/2015 | Eash | |
| 2015/0342616 A1 | 12/2015 | Fryman | |
| 2015/0351780 A1 | 12/2015 | Anderson et al. | |
| 2015/0351916 A1 | 12/2015 | Kosarek et al. | |
| 2016/0015426 A1 | 1/2016 | Dayton | |
| 2016/0038161 A1 | 2/2016 | Gibson | |
| 2016/0100773 A1 | 4/2016 | Ching et al. | |
| 2016/0100847 A1 | 4/2016 | Maxson | |
| 2016/0151165 A1 | 6/2016 | Fallin et al. | |
| 2016/0175089 A1 | 6/2016 | Fallin et al. | |
| 2016/0192951 A1 | 7/2016 | Gelaude et al. | |
| 2016/0199076 A1 | 7/2016 | Fallin et al. | |
| 2016/0199198 A1 | 7/2016 | Dietz et al. | |
| 2016/0213384 A1 | 7/2016 | Fallin et al. | |
| 2016/0256176 A9 | 9/2016 | Lowery et al. | |
| 2016/0270829 A1 | 9/2016 | Duggal et al. | |

(56) References Cited

U.S. PATENT DOCUMENTS

| | | |
|---|---|---|
| 2016/0270855 A1 | 9/2016 | Kunz et al. |
| 2016/0287395 A1 | 10/2016 | Khalili et al. |
| 2016/0338715 A1 | 11/2016 | Bojarski et al. |
| 2016/0354128 A1 | 12/2016 | Jeng et al. |
| 2016/0367270 A1 | 12/2016 | Garlock et al. |
| 2017/0014169 A1 | 1/2017 | Dean et al. |
| 2017/0020537 A1 | 1/2017 | Tuten |
| 2017/0027593 A1 | 2/2017 | Bojarski et al. |
| 2017/0079803 A1 | 3/2017 | Lang |
| 2017/0143511 A1 | 5/2017 | Cachia |
| 2017/0209189 A9 | 7/2017 | Hatch et al. |
| 2017/0231645 A1 | 8/2017 | Metzger et al. |
| 2017/0245906 A1 | 8/2017 | Kugler et al. |
| 2017/0245935 A1 | 8/2017 | Kugler et al. |
| 2017/0249440 A1 | 8/2017 | Lang et al. |
| 2017/0281353 A1 | 10/2017 | Al Hares et al. |
| 2017/0360578 A1 | 12/2017 | Shin et al. |
| 2018/0021145 A1 | 1/2018 | Seavey et al. |
| 2018/0028325 A1 | 2/2018 | Bojarski et al. |
| 2018/0049758 A1 | 2/2018 | Amis et al. |
| 2018/0116804 A1 | 5/2018 | Hafez et al. |
| 2018/0221071 A1 | 8/2018 | Isch |
| 2018/0235706 A1 | 8/2018 | Asseln et al. |
| 2018/0242987 A1 | 8/2018 | Lintula et al. |
| 2018/0289423 A1 | 10/2018 | Singh et al. |
| 2018/0317986 A1 | 11/2018 | Jackman et al. |
| 2018/0344326 A1 | 12/2018 | Chan et al. |
| 2019/0000629 A1 | 1/2019 | Winslow |
| 2019/0008532 A1 | 1/2019 | Fitz et al. |
| 2019/0117239 A1 | 4/2019 | Verma |
| 2019/0175277 A1 | 6/2019 | Chav et al. |
| 2019/0175351 A1 | 6/2019 | Bojarski et al. |
| 2019/0307495 A1 | 10/2019 | Geldwert |
| 2019/0336140 A1* | 11/2019 | Dacosta ............ A61B 17/1682 |
| 2019/0365543 A1 | 12/2019 | Slamin et al. |
| 2020/0008813 A1 | 1/2020 | Bonny et al. |
| 2020/0046374 A1 | 2/2020 | Luttrell et al. |
| 2020/0046425 A1 | 2/2020 | Lopes et al. |
| 2020/0100909 A1 | 4/2020 | Lang et al. |
| 2020/0155323 A1 | 5/2020 | Lang et al. |
| 2020/0163721 A1 | 5/2020 | Aghazadeh |
| 2020/0214719 A1 | 7/2020 | Fraone et al. |
| 2020/0337714 A1 | 10/2020 | Hafez et al. |
| 2020/0356073 A1 | 11/2020 | Tokushima |
| 2020/0405322 A1 | 12/2020 | Brailovski et al. |
| 2021/0007760 A1 | 1/2021 | Reisin |
| 2021/0022781 A1 | 1/2021 | Dacosta et al. |
| 2021/0030429 A1 | 2/2021 | Rose et al. |
| 2021/0045756 A1 | 2/2021 | Zakhary et al. |
| 2021/0059691 A1 | 3/2021 | Zille |
| 2021/0059837 A1 | 3/2021 | Rhodes |
| 2021/0077120 A1 | 3/2021 | Hatch et al. |
| 2021/0077192 A1 | 3/2021 | Perler et al. |
| 2021/0085338 A1 | 3/2021 | Dacosta et al. |
| 2021/0090248 A1 | 3/2021 | Choi et al. |
| 2021/0106427 A1 | 4/2021 | Mahfouz |
| 2021/0113223 A1 | 4/2021 | Schaumann et al. |
| 2021/0121297 A1 | 4/2021 | Cavanagh et al. |
| 2021/0137537 A1 | 5/2021 | Zille |
| 2021/0137538 A1 | 5/2021 | Fallin et al. |
| 2021/0161543 A1 | 6/2021 | Mcauliffe et al. |
| 2021/0186704 A1 | 6/2021 | Fitz et al. |
| 2021/0192759 A1 | 6/2021 | Lang |
| 2021/0196290 A1 | 7/2021 | Iannotti et al. |
| 2021/0212705 A1 | 7/2021 | Reynolds et al. |
| 2021/0219989 A1 | 7/2021 | Chao |
| 2021/0244477 A1 | 8/2021 | Singh et al. |
| 2021/0256171 A1 | 8/2021 | Hosseini |
| 2021/0275196 A1 | 9/2021 | Wodajo |
| 2021/0282790 A1 | 9/2021 | Sellman et al. |
| 2021/0282823 A1 | 9/2021 | Day et al. |
| 2021/0290250 A1 | 9/2021 | Denham et al. |
| 2021/0298766 A1 | 9/2021 | Loring et al. |
| 2021/0307833 A1 | 10/2021 | Farley et al. |
| 2021/0307834 A1 | 10/2021 | Gillman et al. |
| 2021/0346038 A1 | 11/2021 | Fiechter et al. |
| 2021/0378752 A1 | 12/2021 | Paul et al. |
| 2021/0386437 A1 | 12/2021 | Dacosta et al. |
| 2021/0391058 A1 | 12/2021 | Kostrzewski et al. |
| 2021/0393304 A1 | 12/2021 | Geldwert |
| 2022/0039965 A1 | 2/2022 | Casey et al. |
| 2022/0087822 A1 | 3/2022 | Radermacher et al. |
| 2022/0096157 A1 | 3/2022 | Pollock et al. |
| 2022/0133484 A1 | 5/2022 | Lang |
| 2022/0160405 A1 | 5/2022 | Casey et al. |
| 2022/0167998 A1 | 6/2022 | Siccardi et al. |
| 2022/0192685 A1 | 6/2022 | Gazonnet et al. |
| 2022/0202495 A1 | 6/2022 | Pack |
| 2022/0211387 A1 | 7/2022 | Perler et al. |
| 2022/0233203 A1 | 7/2022 | Rhodes et al. |
| 2022/0249106 A1 | 8/2022 | Akallal et al. |
| 2022/0249143 A1 | 8/2022 | Hollis et al. |
| 2022/0270762 A1 | 8/2022 | Crawford et al. |
| 2022/0273450 A1 | 9/2022 | Steines et al. |
| 2022/0296285 A1 | 9/2022 | Le Besque et al. |
| 2022/0313284 A1 | 10/2022 | Korman |
| 2022/0323086 A1 | 10/2022 | Stemniski et al. |
| 2022/0338934 A1 | 10/2022 | Perler et al. |
| 2022/0346806 A1* | 11/2022 | Leemrijse ............ A61B 17/151 |
| 2023/0013727 A1 | 1/2023 | Korman et al. |
| 2023/0014384 A1 | 1/2023 | Cordonnier et al. |
| 2023/0077222 A1 | 3/2023 | Awtrey |
| 2023/0157705 A1 | 5/2023 | Reynolds |
| 2023/0190306 A1 | 6/2023 | Kowalczyk et al. |
| 2023/0281842 A1 | 9/2023 | Ribeiro et al. |
| 2023/0310013 A1 | 10/2023 | Perler et al. |
| 2023/0310051 A1 | 10/2023 | Hafez et al. |
| 2023/0389937 A1 | 12/2023 | Penner et al. |
| 2023/0404673 A1 | 12/2023 | Spitler et al. |
| 2024/0005504 A1 | 1/2024 | Ribeiro et al. |

FOREIGN PATENT DOCUMENTS

| | | |
|---|---|---|
| AU | 2015203808 B2 | 9/2017 |
| AU | 2020220169 A1 | 9/2020 |
| AU | 2021286392 A1 | 1/2022 |
| CA | 2491824 A1 | 9/2005 |
| CA | 2608464 C | 7/2012 |
| CA | 2854997 A1 | 5/2013 |
| CA | 2713309 C | 7/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| CN | 106236185 A | 12/2016 |
| CN | 205924106 U | 2/2017 |
| CN | 206151532 U | 5/2017 |
| CN | 105105853 B | 7/2017 |
| CN | 108030532 A | 5/2018 |
| CN | 207721902 U | 8/2018 |
| CN | 112914724 B | 2/2022 |
| CN | 117297772 B | 2/2024 |
| CN | 117322951 B | 2/2024 |
| CN | 109223098 B | 5/2024 |
| DE | 2910627 A1 | 9/1980 |

(56) References Cited

FOREIGN PATENT DOCUMENTS

| DE | 202006010241 U1 | 3/2007 |
|---|---|---|
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124832 B1 | 8/2012 |
| EP | 2750617 A1 | 7/2014 |
| EP | 2856951 A1 | 4/2015 |
| EP | 2624764 B1 | 12/2015 |
| EP | 3000443 A3 | 7/2016 |
| EP | 2083758 B1 | 11/2017 |
| EP | 2632349 B1 | 3/2018 |
| EP | 3013256 B1 | 11/2018 |
| EP | 3171795 B1 | 11/2018 |
| EP | 3672535 A1 | 7/2020 |
| EP | 2558010 B1 | 5/2021 |
| EP | 3948895 A1 | 2/2022 |
| EP | 3740141 B1 | 4/2022 |
| EP | 2844162 B1 | 7/2022 |
| FR | 2362616 A1 | 3/1978 |
| FR | 2764183 A1 | 12/1998 |
| FR | 2953120 B1 | 1/2012 |
| FR | 3030221 A1 | 6/2016 |
| FR | 3117328 B1 | 3/2023 |
| GB | 2154143 A | 9/1985 |
| GB | 2154144 A | 9/1985 |
| GB | 2334214 B | 1/2003 |
| GB | 2589960 A | 6/2021 |
| JP | S635739 A | 1/1988 |
| JP | 2004174265 A | 6/2004 |
| JP | 2006158972 A | 6/2006 |
| JP | 4134243 B2 | 8/2008 |
| JP | 2011092405 A | 5/2011 |
| JP | 4796943 B2 | 10/2011 |
| JP | 2014511207 A | 5/2014 |
| JP | 2014521384 A | 8/2014 |
| KR | 100904142 B1 | 6/2009 |
| KR | 1020160090006 A | 7/2016 |
| KR | 1020180118476 A | 10/2018 |
| KR | 101952368 B1 | 2/2019 |
| MD | 756 B1 | 7/1997 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| RU | 182499 U1 | 8/2018 |
| RU | 2789960 C2 | 2/2023 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009001083 A1 | 12/2008 |
| WO | 2009029798 A1 | 3/2009 |
| WO | 2009032101 A2 | 3/2009 |
| WO | 2010099231 A3 | 11/2010 |
| WO | 2011005327 A1 | 1/2011 |
| WO | 2011037885 A1 | 3/2011 |
| WO | 2012024317 A2 | 2/2012 |
| WO | 2012029008 A1 | 3/2012 |
| WO | 2012176077 A1 | 12/2012 |
| WO | 2013026786 A1 | 2/2013 |
| WO | 2013041618 A1 | 3/2013 |
| WO | 2013134387 A1 | 9/2013 |
| WO | 2013156816 A2 | 10/2013 |
| WO | 2014020561 A1 | 2/2014 |
| WO | 2014020562 A1 | 2/2014 |
| WO | 2014022055 A1 | 2/2014 |
| WO | 2014085882 A1 | 6/2014 |
| WO | 2014147099 A1 | 9/2014 |
| WO | 2014152219 A2 | 9/2014 |
| WO | 2014200017 A1 | 12/2014 |
| WO | 2015003284 A2 | 1/2015 |
| WO | 2015094409 A1 | 6/2015 |
| WO | 2015127515 A2 | 9/2015 |
| WO | 2016012731 A1 | 1/2016 |
| WO | 2016102025 A1 | 6/2016 |
| WO | 2017031000 A1 | 2/2017 |
| WO | 2017122076 A2 | 7/2017 |
| WO | 2017151833 A1 | 9/2017 |
| WO | 2018167369 A1 | 9/2018 |
| WO | 2019060780 A2 | 3/2019 |
| WO | 2019052622 A4 | 5/2019 |
| WO | 2019180747 A1 | 9/2019 |
| WO | 2020060349 A1 | 3/2020 |
| WO | 2021054518 A1 | 3/2021 |
| WO | 2021091071 A1 | 5/2021 |
| WO | 2021118733 A1 | 6/2021 |
| WO | 2021127625 A1 | 6/2021 |
| WO | 2021240290 A1 | 12/2021 |
| WO | 2022155208 A1 | 7/2022 |
| WO | 2022182312 A1 | 9/2022 |
| WO | 2023096516 A1 | 6/2023 |
| WO | 2024025840 A1 | 2/2024 |

OTHER PUBLICATIONS

"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Acumed "Acumed Osteotomy System" with partial English Translation, 2014, pp. 19.
Additive Orthopaedics, "The First and Only FDA Approved Patient Specific Talus Spacer", https://totaltalusreplacement.com, Downloaded: Mar. 4, 2022, pp. 11.
Aiyer et al. "Prevalence of Metatarsus Adductus in Patients Undergoing Hallux Valgus Surgery" Foot & Ankle International 2014, vol. 35(12), pp. 1292-1297.
Albano et al. "Biomechanical Study of Transcortical or Transtrabecular Bone Fixation of Patellar Tendon Graft With Bioabsorbable Pins in ACL Reconstruction in Sheep" Rev Bras Ortop. 2012, 47(1), pp. 43-49.
Alvine et al. "Peg and Dowel Fusion of the Proximal Interphalangeal Joint" Foot & Ankle vol. 1, No. 2, 1980 American Orthopaedic Foot Society, pp. 5.
Arthrex "Chevron Osteotomy" https://www.arthrex.com/foot-ankle/chevron-osteotomy, Retrieved Nov. 30, 2022, pp. 7.
Arthrex "Comprehensive Foot System" https://www.arthrex.com/resources/animation/8U3iaPvY6kO8bwFAwZF50Q/comprehensive-foot-system?referringTeam=foot_and_ankle, Published Aug. 27, 2013, pp. 3.
Arthrex, "Distal Tibia Allograft Workstation for Glenoid Bone Loss, Surgical Technique" Arthrex.com, 2018, pp. 8.
Baravarian, "Why the Lapidus Procedure is Ideal for Bunions" Podiatry Today, https://www.hmpgloballearningnetwork.com/site/podiatry/article/5542, May 2006 pp. 8.
Bauer et al. "Offset-V Osteotomy of the First Metatarsal Shaft in Hallux Abducto Valgus" Chapter 29, McGlamry's Comprehensive Textbook of Foot and Ankle Surgery, Fourth Edition, 2013, pp. 26.
Bednarz et al. "Modified Lapidus Procedure for the Treatment of Hypermobile Hallux Valgus" Foot & Ankle, American Orthopaedic Foot & Ankle Society, 2000, pp. 6.
Bennett et al. "Intraosseous Sliding Plate Fixation Used in Double Osteotomy Bunionectomy" Foot & Ankle International, 2019, vol. 40(1), pp. 85-88.
Biopro "Accu-Cut Osteotomy Guide System Accurate and consistent hallux valgus correction" Document Dates Sep. 16, 2019, pp. 2.
Boffeli et al. "Can We Abandon Saw Wedge Resection in Lapidus Fusion? A Comparative Study of Joint Preparation Techniques

(56) References Cited

OTHER PUBLICATIONS

Regarding Correction of Deformity, Union Rate, and Preservation of First Ray Length" The Journal of Foot & Ankle Surgery, 58, 2019, pp. 1118-1124.

Bouaicha et al. "Fixation of Maximal Shift Scarf Osteotomy with Inside-Out Plating: Technique Tip" Foot & Ankle International, vol. 32, No. 5, May 2011, pp. 567-569.

Buda et al. "Effect of Fixation Type and Bone Graft on Tarsometatarsal Fusion" Foot & Ankle International 2018, vol. 39(12), pp. 1394-1402.

Carr et al. "Correctional Osteotomy for Metatarsus Primus Varus and Hallux Valgus*" The Journal of Bone and Joint Surgery, vol. 50-A, No. 7, Oct. 1968, pp. 1353-1367.

Catanese et al. "Measuring Sesamoid Position in Hallux Valgus When Is the Sesamoid Axial View Necessary?" Foot & Ankle Specialist, Downloaded Aug. 15, 2016, pp. 1-3.

Chesser et al. "New Advances With The Tarsometatarsal" Podiatry Today, vol. 30, Issue 10, Oct. 2017, pp. 28-36.

Chomej et al. "Lateralising DMMO (MIS) for simultaneous correction of a pes adductus during surgical treatment of a hallux valgus" Journal Pre-proof, The Foot, Accepted Jul. 16, 2020, pp. 33.

Cichero et al. "Different fixation constructs and the risk of non-union following first metatarsophalangeal joint arthrodesis" Foot and Ankle Surgery, 27, 2021, Accepted Oct. 15, 2020, pp. 789-792.

Coetzee et al., "Revision Hallux Valgus Correction," Operative Techniques in Foot and Ankle Surgery, Section I, Chapter 15, 2011, pp. 84-96.

Collan et al., "The biomechanics of the first metatarsal bone in hallux valgus: A preliminary study utilizing a weight bearing extremity CT," Foot and Ankle Surgery, vol. 19, 2013, pp. 155-161.

"Futura Forefoot Implant Arthroplasty Products," Tornier, Inc., 2008, 14 pages.

"HAT-TRICK Lesser Toe Repair System, Foot and Ankle Technique Guide, Metatarsal Shortening Osteotomy Surgical Technique," Smith & Nephew, 2014, 16 pages.

"HAT-TRICK Lesser Toe Repair System," Smith & Nephew, Brochure, Aug. 2014, 12 pages.

"Hoffmann II Compact External Fixation System", Stryker, Brochure, Literature No. 5075-1-500, 2006, 12 pages.

"Hoffmann II Micro Lengthener", Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Patient to Patient Precision, Accu-Cut, Osteotomy Guide System, BioPro, Foot & Ankle International Journal, vol. 23, No. 8, Aug. 2002, 2 pages.

Blomer "Problems and complications of knee endoprostheses from a manufacturer's point of view Orthopade 200, 29, pp. 688-696, English Abstract."

"Prophecy Inbone Preoperative Navigation Guides", Wright Medical Technology, Inc., Nov. 2013, 6 pages.

"RAYHACK Ulnar Shortening Generation II Low-Profile Locking System Surgical Technique," Wright Medical Technology, Inc., Dec. 2013, 20 pages.

Smith & Nephew scores a HAT-TRICK with its entry into the high-growth hammer toe repair market, Smith & Nephew, Jul. 31, 2014, 2 pages.

"Lag Screw Target Bow," Stryker Leibinger GmbH & Co. KG, Germany 2004, 8 pages.

Anderson et al. "Uncemented STAR Total Ankle Protheses" Journal of Bone Joint Surgery America, Sep. 2004, Abstract of Article, pp. 6.

Coetzee et al., "The Lapidus Procedure: A Prospective Cohort Outcome Study," Foot & Ankle International, vol. 25, No. 8, Aug. 2004, pp. 526-531.

Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.

Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.

Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.

Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.

Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.

Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.

Decarbo et al., "The Weil Osteotomy: A Refresher," Techniques in Foot and Ankle Surgery, vol. 13, No. 4, Dec. 2014, pp. 191-198.

Defendant Fusion Orthopedics LLC's Invalidity Contentions, No. CV-22-00490-PHX-SRB, US District Court for the District of Arizona, Aug. 27, 2022, 41 pages.

Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.

Dinapoli et al., "Metatarsal Osteotomy for the Correction of Metatarsus Adductus," Reconstructive Surgery of the Foot and Leg, 1989, pp. 242-250.

Disior, "Bonelogic Foot & Ankle Module" , https://www.disior.com/foot--ankle.html, Downloaded Jun. 1, 2022, pp. 6.

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

Dubovik et al., "Talonavicular Joint Arthrodesis and Medial Displacement Calcaneal Osteotomy for Treatment of Patients With Planovalgus Deformity" Traumatology and Orthopedics of Russia, vol. 18, No. 3, Sep. 30, 2012, pp. 83-88.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Easley et al., "Current Concepts Review: Hallux Valgus Part II: Operative Treatment," Foot and Ankle International, vol. 28, No. 6, Jun. 2007, pp. 748-758.

(56) References Cited

OTHER PUBLICATIONS

Easley et al., "What is the Best Treatment for Hallux Valgus?," Evidence-Based Orthopaedics—The Best Answers to Clinical Questions, Chapter 73, 2009, pp. 479-491.

EBI Extra Small Rail Fixator, Biomet Trauma, retrieved Dec. 19, 2014, from the Internet: < http://footandanklefixation.com/product/biomet-trauma-ebi-extra-small-rail-fixator>, 7 pages.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Eustace et al., "Hallux valgus, first metatarsal pronation and collapse of the medial longitudinal arch—a radiological correlation," Skeletal Radiology, vol. 23, 1994, pp. 191-194.

Fallin et al., US Provisional Application Entitled Indexed Tri-Planar Osteotomy Guide and Method, U.S. Appl. No. 62/118,378, filed Feb. 19, 2015, 62 pages.

Fazal et al., "First metatarsophalangeal joint arthrodesis with two orthogonal two hole plates," Acta Orthopaedica et Traumatologica Turcica, vol. 52, 2018, pp. 363-366.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Ferrari et al., "A Radiographic Study of the Relationship Between Metatarsus Adductus and Hallux Valgus," The Journal of Foot and Ankle Surgery, vol. 42, No. 1, 2003, pp. 9-14.

Ferreyra et al., "Can we correct first metatarsal rotation and sesamoid position with the 3D Lapidus procedure?," Foot and Ankle Surgery, vol. 28, No. 3, Apr. 2022, pp. 313-318.

Fibretuff, "3D Printing, CNC Machining, Molding and Extruding Biocompatible material's with "bone like" Qualities for 3D Printing" https://fibretuff.us, Downloaded Feb. 24, 2023, pp. 22.

Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Flavin et al., "Arthrodesis of the First Metatarsophalangeal Joint Using a Dorsal Titanium Contoured Plate," Foot & Ankle International, vol. 25, No. 11, Nov. 2004, pp. 783-787.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fraissler et al., "Treatment of hallux valgus deformity," Efort Open Reviews, vol. 1, Aug. 2016, pp. 295-302.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, pp. 437-440.

Garthwait, "Accu-Cut System Facilitates Enhanced Precision," Podiatry Today, vol. 18, No. 6, Jun. 2005, 6 pages.

Gerard et al., "The Modified Lapidus Procedure," Orthopedics, vol. 31, No. 3, Mar. 2008, 7 pages.

Ghali et al., "The Management of Metatarsus Adductus et Supinatus," The Journal of Bone and Joint Surgery, vol. 66-B, No. 3, May 1984, pp. 376-380.

Giannoudis et al., "Hallux Valgus Correction," Practical Procedures in Elective Orthopaedic Surgery, Pelvis and Lower Extremity, Chapter 38, 2012, 22 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems fr die Knieendoprothetik," Forschungsberichte, Technische Universitat Munchen, 165, 2002, 11 pages, including partial English Translation.

Gould et al., "A Prospective Evaluation of First Metatarsophalangeal Fusion Using an Innovative Dorsal Compression Plating System," The Journal of Foot & Ankle Surgery, vol. 60, 2021, pp. 891-896.

Gregg et al., "Plantar plate repair and Weil osteotomy for metatarsophalangeal joint instability," Foot and Ankle Surgery, vol. 13, 2007, pp. 116-121.

Greiner, "The Jargon of Pedal Movements," Foot & Ankle International, vol. 28, No. 1, Jan. 2007, pp. 109-125.

Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).

Groves, "Functional Position Joint Sectioning: Pre-Load Method for Lapidus Arthrodesis," The Podiatry Institute, Update 2015, Chapter 6, 2015, pp. 23-29.

Groves, "Operative Report," St. Tammany Parish Hospital, Date of Procedure, Mar. 26, 2014, 2 pages.

Gutteck et al., "Comparative study of Lapidus bunionectomy using different osteosynthesis methods," Foot and Ankle Surgery, vol. 19, 2013, pp. 218-221.

Gutteck et al., "Is it feasible to rely on intraoperative X ray in correcting hallux valgus?," Archives of Orthopaedic and Trauma Surgery, vol. 133, 2013, pp. 753-755.

Hardy et al., "Observations on Hallux Valgus," The Journal of Bone and Joint Surgery, vol. 33B, No. 3, Aug. 1951,pp. 376-391.

Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.

Hatch et al., "Triplane Hallux Abducto Valgus Classification," The Journal of Foot & Ankle Surgery, vol. 57, No. 5, Sep./Oct. 2018, published online: May 18, 2018, pp. 972-981.

Hetherington et al., "Evaluation of surgical experience and the use of an osteotomy guide on the apical angle of an Austin osteotomy," The Foot, vol. 18, 2008, pp. 159-164.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.

Ho et al., "Hallux rigidus," Efort Open Reviews, vol. 2, Jan. 2017, pp. 13-20.

Hunt et al., "Locked Versus Nonlocked Plate Fixation For Hallux MTP Arthrodesis," Foot and Ankle International, vol. 32, No. 7, Jul. 2011, pp. 704-709.

Integra, "Integra Large Qwix Positioning and Fixation Screw, Surgical Technique," 2012, 16 pages.

Jackson III et al., "The Surgical Learning Curve for Modified Lapidus Procedure for Hallux Valgus Deformity," Foot & Ankle Specialist, Jul. 2021, 5 pages.

Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

(56) References Cited

OTHER PUBLICATIONS

Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.

KLS Martin Group, "Individual Patient Solutions IPS Implants", https://www.klsmartin.com/en-na/products/individual-patient-solutions/ips-implants/, Downloaded: Jun. 1, 2022, pp. 8.

Kurup et al., "Midfoot arthritis—current concepts review," Journal of Clinical Orthopaedics and Trauma, vol. 11, 2020, pp. 399-405.

La Reaux et al., "Metatarsus adductus and hallux abducto valgus: their correlation," The Journal of Foot Surgery, vol. 26, No. 4, Jul. 1987, pp. 304-308, Abstract Only.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Lapidus, "The Author's Bunion Operation From 1931 to 1959," Clinical Orthopaedics, vol. 16, 1960, pp. 119-135.

Latif et al., "First metatarsophalangeal fusion using joint specific dorsal plate with interfragmentary screw augmentation: Clinical and radiological outcomes," Foot and Ankle Surgery, vol. 25, 2019, pp. 132-136.

Le et al., "Tarsometatarsal Arthrodesis," Operative Techniques in Foot and Ankle Surgery, Section II, Chapter 40, 2011, pp. 281-285.

Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.

Little, "Joint Arthrodesis For Hallux Valgus," Clinics in Podiatric Medicine and Surgery, Hallux Abducto Valgus Surgery, updated Apr. 19, 2014, retrieved online from <https://www.footankleinstitute.com/first-metatarsophalangeal-joint-arthrodesis-in-the-treatment-of-hallux-valgus>, 7 pages.

Lopez et al., "Metatarsalgia: Assessment Algorithm and Decision Making," Foot and Ankle Clinics, vol. 24, No. 4, Dec. 2019, published online: Sep. 25, 2019, pp. 561-569.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Machacek Jr. et al., "Salvage of a Failed Keller Resection Arthroplasty," The Journal of Bone and Joint Surgery, vol. 86A, No. 6, Jun. 2004, pp. 1131-1138.

Magin, "Computernavigierter Gelenkersatz am Knie mit dem Orthopilot," Operative Orthopdie und Traumatologie, vol. 22, No. 1, 2010, pp. 63-80, including English Abstract on p. 64.

Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.

Marshall et al., "The identification and appraisal of assessment tools used to evaluate metatarsus adductus: a systematic review of their measurement properties," Journal of Foot and Ankle Research, vol. 11, No. 25, 2018, 10 pages.

Mcaleer et al., "A systematic approach to the surgical correction of combined hallux valgus and metatarsus adductus deformities," The Journal of Foot & Ankle Surgery, May 21, 2021, 6 pages.

Mcaleer et al., "Radiographic Outcomes Following Triplanar Correction of Combined Hallux Valgus and Metatarsus Adductus Deformities," ACFAS Scientific Conference, Poster, Feb. 2022, 1 page.

Mccabe et al., "Anatomical reconstruction of first ray instability hallux valgus with a medial anatomical TMTJ1 plate," Foot and Ankle Surgery, vol. 27, No. 8, Dec. 2021, pp. 869-873.

Mehtar et al., "Outcomes of bilateral simultaneous hallux MTPJ fusion," Foot and Ankle Surgery, vol. 27, 2021, pp. 213-216.

Michelangelo Bunion System, Surgical Technique ", Instratek Incorporated, publication date unknown, 4 pages."

Miller et al., "Variable Angle Locking Compression Plate as Alternative Fixation for Jones Fractures: A Case Series," Kansas Journal of Medicine, vol. 12, No. 2, May 2019, pp. 28-32.

Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.

Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.

Mizuno et al., "Detorsion Osteotomy of the First Metatarsal Bone in Hallux Valgus," Japanese Orthopaedic Association, Tokyo, 1956; 30:813-819.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).

Mortier et al., "Axial Rotation of the First Metatarsal Head in a Normal Population and Hallux Valgus Patients," Orthopaedics and Traumatology: Surgery and Research, vol. 98, 2012, pp. 677-683.

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Musculoskeletal Key "Arthrodesis of the Tarsmetatarsal Joint" https://musculoskeletalkey.com/arthrodesis-of-the-tarsometatarsal-joint/, Retrieved May 8, 2020, pp. 11.

Myerson, "Cuneiform-Metatarsal Arthrodesis," The Foot and Ankle, Chapter 9, 1997, pp. 107-117.

Nagy et al., "The AO Ulnar Shortening Osteotomy System Indications and Surgical Technique," Journal of Wrist Surgery, vol. 3, No. 2, 2014, pp. 91-97.

NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.

Nix et al., "Prevalence of hallux valgus in the general population: a systematic review and meta-analysis," Journal of Foot and Ankle Research, vol. 3, No. 21, 2010, 9 pages.

Novastep, "Pecaplasty Percutaneous Bunion Correction" Downloaded Jun. 29, 2022, pp. 24.

Novastep, "Pecaplasty Percutaneous Bunion Correction—Brochure Pecaplasty Targeting Guide" Downloaded Dec. 15, 2021, pp. 4.

Odenbring et al., "A guide instrument for high tibial osteotomy," Acta Orthopaedica Scandinavica, vol. 60, No. 4, 1989, pp. 449-451.

Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.

Instratek, "Michelangelo Bunion System, Surgical Technique", Instratek Incorporated, publication date unknown, 4 pages.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Weber et al., "A Simple System For Navigation Of Bone Alignment Osteotomies Of The Tibia," International Congress Series, vol. 1268, Jan. 2004, pp. 608-613, (Abstract Only).

Wukich et al., "Hypermobility of the First Tarsometatarsal Joint," Foot and Ankle Clinics, vol. 10, No. 1, Mar. 2005, pp. 157-166.

(56) References Cited

OTHER PUBLICATIONS

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fuchirurgie Das V-tek-System," ABW Wissenschaftsverlag GmbH, 2009, 11 pages, including English Abstract.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Wienke et al., "Bone Stimulation For Nonunions: What the Evidence Reveals," Podiatry Today, vol. 24, No. 9, Sep. 2011, pp. 52-57.

Williams et al., "Metatarsus adductus: Development of a non-surgical treatment pathway," Journal of Paediatrics and Child Health, vol. 49, 2013, pp. E428-433.

Yasuda et al., "Proximal Supination Osteotomy of the First Metatarsal for Hallux Valgus," Foot and Ankle International, vol. 36, No. 6, Jun. 2015, pp. 696-704.

Walker et al., "The Role of First Ray Insufficiency in the Development of Metatarsalgia," Foot and Ankle Clinics, vol. 24, No. 4, Dec. 2019, published online: Sep. 5, 2019, pp. 641-648.

Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.

Wright Medical, "How BLUEPRINT Works—from CT to 3D [CAW-9389]", https://www.wrightmeded.com/videos/how-blueprint-works-from-ct-to-3d-caw-9389, video time mark 32 seconds to 48 seconds, Dated May 26, 2022.

Tricot et al., "3D-corrective osteotomy using surgical guides for posttraumatic distal humeral deformity," Acta Orthopaedica Belgica, vol. 78, No. 4, 2012, pp. 538-542.

Vaida et al., "Effect on Foot Width With Triplanar Tarsometatarsal Arthrodesis for Hallux Valgus," Foot & Ankle Orthopaedics, vol. 5, No. 3, 2020, pp. 1-5.

Nyska, Synergy 3D Med, "Anatomical Model: Calcaneus", 2022, pp. 3.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.

Park et al., "Comparative analysis of clinical outcomes of fixed-angle versus variable-angle locking compression plate for the treatment of Lisfranc injuries," Foot and Ankle Surgery, vol. 26, 2020, pp. 338-342.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.

Perler, "Cuboid Suspension in Charcot Reconstruction. Using 3D Imaging for Planning, Printing and Execution for Complex Deformity Correction" Downloaded Apr. 2021, pp. 4.

Peters et al., "Flexor Hallucis Longus Tendon Laceration as a Complication of Total Ankle Arthroplasty," Foot & Ankle International, vol. 34, No. 1, 2013, pp. 148-149.

Ray et al., "Hallux Valgus," Foot & Ankle Orthopaedics, vol. 4, No. 2, 2019, pp. 1-12.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Rx-Fix Mini Rail External Fixator, Wright Medical Technology, Brochure, Aug. 15, 2014, 2 pages.

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Santrock et al., "Hallux Valgus Deformity and Treatment: A Three-Dimensional Approach: Lapiplasty," Foot & Ankle Clinics, vol. 23, No. 2, 2018, pp. 281-295.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Schon et al., "Cuneiform-Metatarsal Arthrodesis for Hallux Valgus," The Foot and Ankle, Second Edition, Chapter 8, 2002, pp. 99-117.

Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.

Shima et al., "Operative Treatment for Hallux Valgus With Moderate to Severe Metatarsus Adductus," Foot & Ankle International, vol. 40, No. 6, 2019, pp. 641-647.

Shurnas et al., "Proximal Metatarsal Opening Wedge Osteotomy," Operative Techniques in Foot and Ankle Surgery, Section I, Chapter 13, 2011, pp. 73-78.

Siddiqui et al. "Fixation Of Metatarsal Fracture With Bone Plate In A Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.

Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

Smith et al., "Intraoperative Multiplanar Alignment System to Guide Triplanar Correction of Hallux Valgus Deformity," Techniques in Foot & Ankle Surgery, 2017, 8 pages.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Smith et al., "Understanding Frontal Plane Correction in Hallux Valgus Repair," Clinics in Podiatric Medicine and Surgery, vol. 35, 2018, pp. 27-36.

(56)     References Cited

OTHER PUBLICATIONS

Sokoloff, "Lapidus Procedure," Textbook of Bunion Surgery, Chapter 15, 1981, pp. 277-287.

Stableloc External Fixation System, Acumed, Product Overview, Effective date Sep. 2015, 4 pages.

Stahl et al., "Derotation Of Post-Traumatic Femoral Deformities By Closed Intramedullary Sawing," Injury, vol. 37, No. 2, Feb. 2006, pp. 145-151, (Abstract Only).

Stamatis et al., "Mini Locking Plate as Medial Buttress for Oblique Osteotomy for Hallux Valgus," Foot & Ankle International, vol. 31, No. 10, Oct. 2010, pp. 920-922.

Stryker, "PROstep Minimally Invasive Surgery" https://www.stryker.com/us/en/foot-and-ankle/products/prostep.html, Downloaded Jun. 23, 2023, pp. 10.

Synergy 3D Med, "Anatomical Model: Calcaneus" Downloaded Mar. 2, 2023, pp. 2.

Synopsys, "Medical Image Segmentation with Machine Learning—Simpleware Automated Solution Modules", https://www.synopsys.com/simpleware/software/auto-segmenter-modules.html#simpleware-as-ortho, 2022, pp. 12.

Talbot et al., "Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Tornier Technology, "Tornier Blueprint 3D Planning + PSI" , https://www.wrightemedia.com/ProductFiles/Files/PDFs/CAW-8609_EN_HR_LE.pdf, Feb. 2017, pp. 12.

Total Ankle Institute, "Prophecy: Preoperative Navigation Guides", https://www.totalankleinstitute.com/infinity-products/prophecy-preoperative-navigation-guides/, 2019, pp. 6.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

Treace "FastGrafter Autograft Harvesting System" Downloaded from https://www.lapiplasty.com/surgeons/other-products/fastgrafter/, Dec. 4, 2024, pp. 8.

Treace Medical Concepts, "Adductoplasty Midfoot Correction System", https://www.lapiplasty.com/surgeons/other-products/adductoplasty-system/, Downloaded May 2, 2022, pp. 9.

Use for BME Speed Nitinol Staple Fixation for the Lapidus Procedure, "date unknown, 1 page."

Virzi et al. "Comprehensive Review of 3D Segmentation Software Tools for MRI Usable for Pelvic Surgery Planning", Journal of Digital Imaging (2020) 33, pp. 99-110.

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.

D'Amico et al., "Motion of the First Ray: Clarification Through Investigation," Journal of the American Podiatry Association, vol. 69, No. 1, Jan. 1979, pp. 17-23.

Dayton et al., "Biwinged Excision for Round Pedal Lesions," The Journal of Foot and Ankle Surgery, vol. 35, No. 3, 1996, pp. 244-249.

Coughlin "Proximal Metatarsal Osteotomy and Distal Soft Tissue Reconstruction for Hallux Valgus in Juveniles" Orthopaedics and Traumatology, vol. 7, Published: Jun. 1999, pp. 133-143.

Dayton et al., "Medial Incision Approach to the First Metatarsophalangeal Joint," The Journal of Foot and Ankle Surgery, vol. 40, No. 6, Nov./Dec. 2001, pp. 414-417.

Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.

Dayton et al., "Use of the Z Osteotomy for Tailor Bunionectomy," The Journal of Foot and Ankle Surgery, vol. 42, No. 3, May/Jun. 2003, pp. 167-169.

Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Dayton et al., "The Extended Knee Hemilithotomy Position for Gastrocnemius Recession," The Journal of Foot and Ankle Surgery, vol. 49, 2010, pp. 214-216.

Dayton et al., "A User-Friendly Method of Pin Site Management for External Fixators," Foot and Ankle Specialist, Sep. 16, 2011, 4 pages.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Principles of Management of Growth Plate Fractures in the Foot and Ankle," Clinics in Podiatric Medicine and Surgery, Pediatric Foot Deformities, Oct. 2013, 17 pages.

Crawford et al. "Metatarsus Adductus: Radiographic and Pathomechanical Analysis" Chapter 5, https://www.podiatryinstitute.com/pdfs/Update_2014/2014_05.pdf, Published 2014, pp. 25-30.

Dayton et al., "Clarification of the Anatomic Definition of the Bunion Deformity," The Journal of Foot and Ankle Surgery, vol. 53, 2014, pp. 160-163.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Dayton et al., "Technique for Minimally Invasive Reduction of Calcaneal Fractures Using Small Bilateral External Fixation," The Journal of Foot and Ankle Surgery, Article in Press, 2014, 7 pages.

Dayton, "Tarsal-Metatarsal Joint: Primary & Revision Arthrodesis" Disclosure: Speaker for Orthofix and Biomet, Apr. 2014, pp. 38.

Dalat et al. "Does arthrodesis of the first metatarsophalangeal joint correct the intermetatarsal M1M2 angle? Analysis of a continuous series of 208 arthrodeses fixed with plates" Orthopaedics & Traumatology: Surgery & Research 101, 2015, pp. 709-714.

Dayton et al., "A new triplanar paradigm for bunion management," Lower Extremity Review, Apr. 2015, 9 pages.

(56)         References Cited

OTHER PUBLICATIONS

Dayton et al., "Comparison of Complications for Internal and External Fixation for Charcot Reconstruction: A Systematic Review," The Journal of Foot and Ankle Surgery, Article in Press, 2015, 4 pages.

Dayton et al., "Complications of Metatarsal Suture Techniques for Bunion Correction: A Systematic Review of the Literature," The Journal of Foot and Ankle Surgery, Article in Press, 2015, 3 pages.

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

Dayton et al. "Comparison of Tibial Sesamoid Position on Anteroposterior and Axial Radiographs Before and After Triplane Tarsal Metatarsal Joint Arthrodesis" The Journal of Foot & Ankle Surgery 56, 2017, pp. 1041-1046.

Dayton "Evidence-Based Bunion Surgery: A Critical Examination of Current and Emerging Concepts and Techniques" Springer International Publishing, 2017, pp. 254.

Dayton et al. "Biomechanical Characteristics of Biplane Multiplanar Tension-Side Fixation for Lapidus Fusion" The Journal of Foot & Ankle Surgery, 2018, pp. 1-5.

Dayton et al. "Progression of Healing on Serial Radiographs Following First Ray Arthrodesis in the Foot Using a Biplanar Plating Technique Without Compression" The Journal of Foot & Ankle Surgery, 2018, pp. 1-7.

Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.

Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.

Conti et al., "Effect of the Modified Lapidus Procedure for Hallux Valgus on Foot Width," Foot & Ankle International, Feb. 1, 2020, published online: Oct. 30, 2019, 6 pages.

Conti et al., "Effect of the Modified Lapidus Procedure on Pronation of the First Ray in Hallux Valgus," Foot & Ankle International, Feb. 1, 2020, published online: Oct. 16, 2019, 8 pages.

Dayton et al. "Comparison of Radiographic Measurements Before and After Triplane Tarsometatarsal Arthrodesis for Hallux Valgus" The Journal of Foot & Ankle Surgery 59, 2020, pp. 291-297.

Curran et al. "Functional Capabilities After First Metatarsal Phalangeal Joint Arthrodesis Using a Locking Plate and Compression Screw Construct" The Journal of Foot & Ankle Surgery, 2021, pp. 1-5.

De Carvalho, et al. "Automated Three-dimensional distance and coverage mapping of hallux valgus: a case-control study" Journal of Foot and Ankle, 2022; 16(1), pp. 5.

Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

De Heer et al., "Procedure-Specific Hardware Removal After Evans Osteotomy" Journal of the American Podiatric Medical Association, vol. 110, No. 2, Mar./Apr. 2020, pp. 1-7.

DeCarbo et al., "Locking Plates: Do They Prevent Complications?," Podiatry Today, Apr. 2014, 7 pages.

DeCarbo et al., "Resurfacing Interpositional Arthroplasty for Degenerative Joint Disease of the First Metatarsalphalangeal Joint," Podiatry Management, Jan. 2013, pp. 137-142.

* cited by examiner

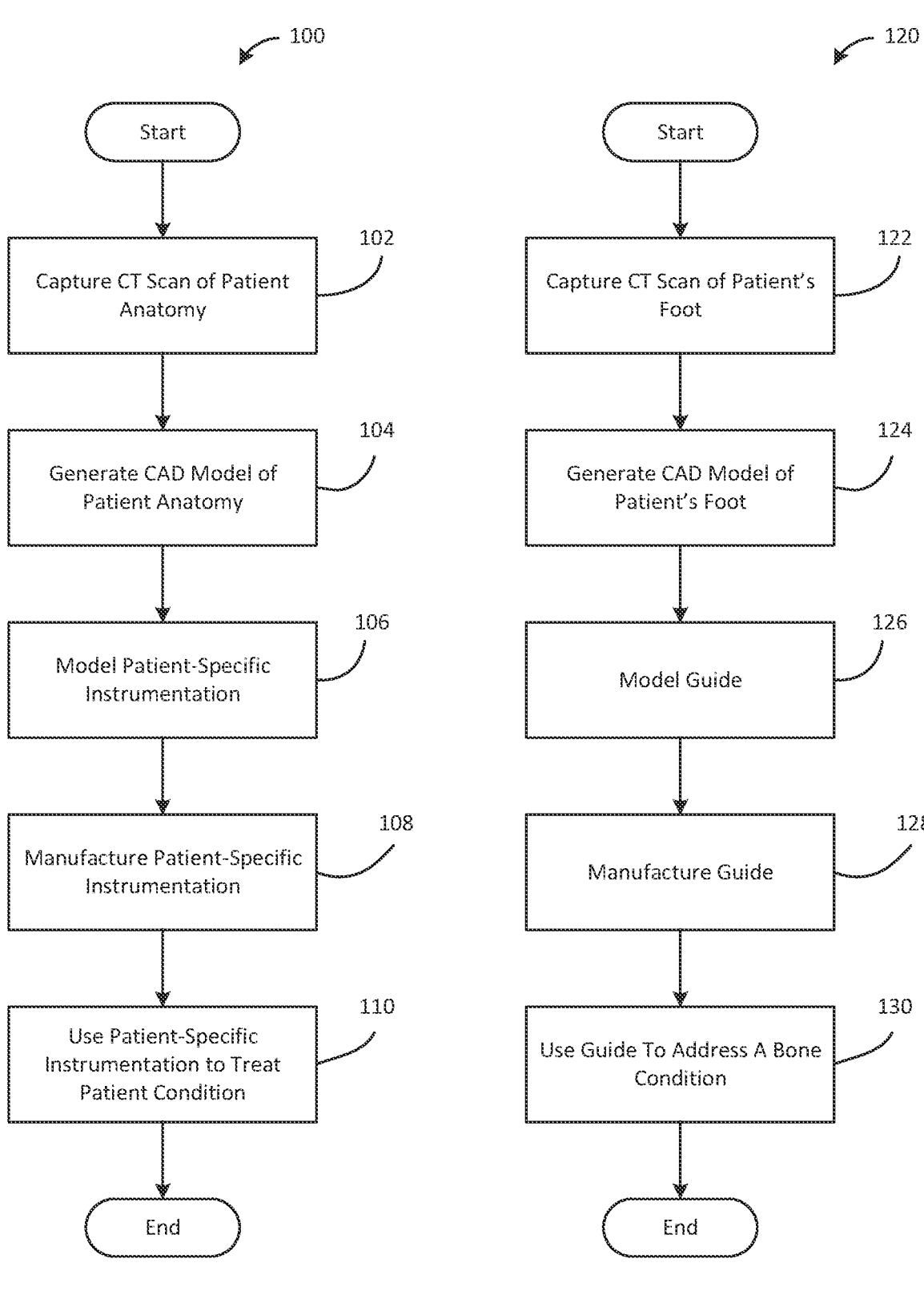
FIG. 1A                    FIG. 1B

264
Frontal
Plane

Transverse
Plane
266

262
Sagittal
Plane

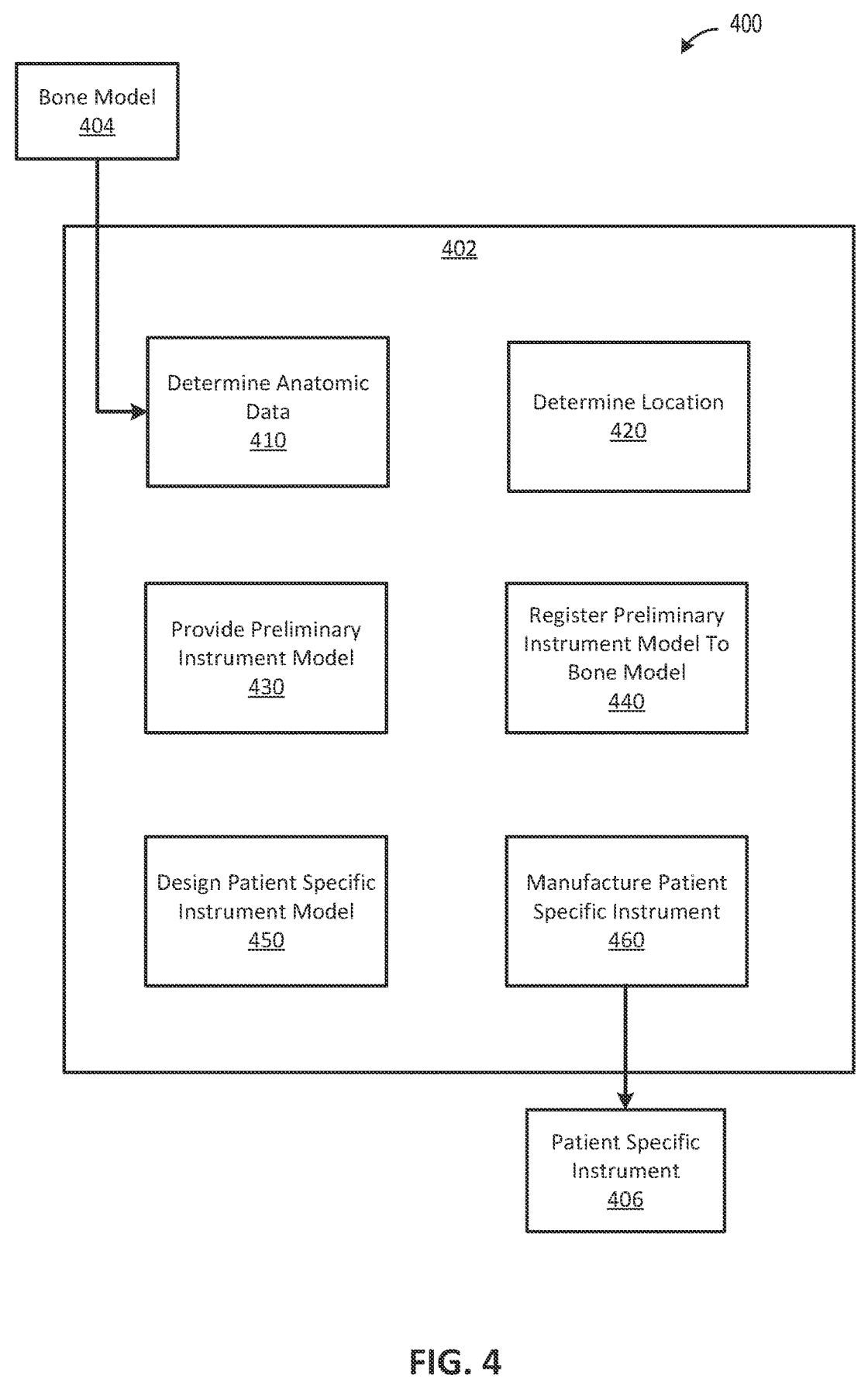

400

Bone Model
404

402

Determine Anatomic
Data
410

Determine Location
420

Provide Preliminary
Instrument Model
430

Register Preliminary
Instrument Model To
Bone Model
440

Design Patient Specific
Instrument Model
450

Manufacture Patient
Specific Instrument
460

Patient Specific
Instrument
406

FIG. 4

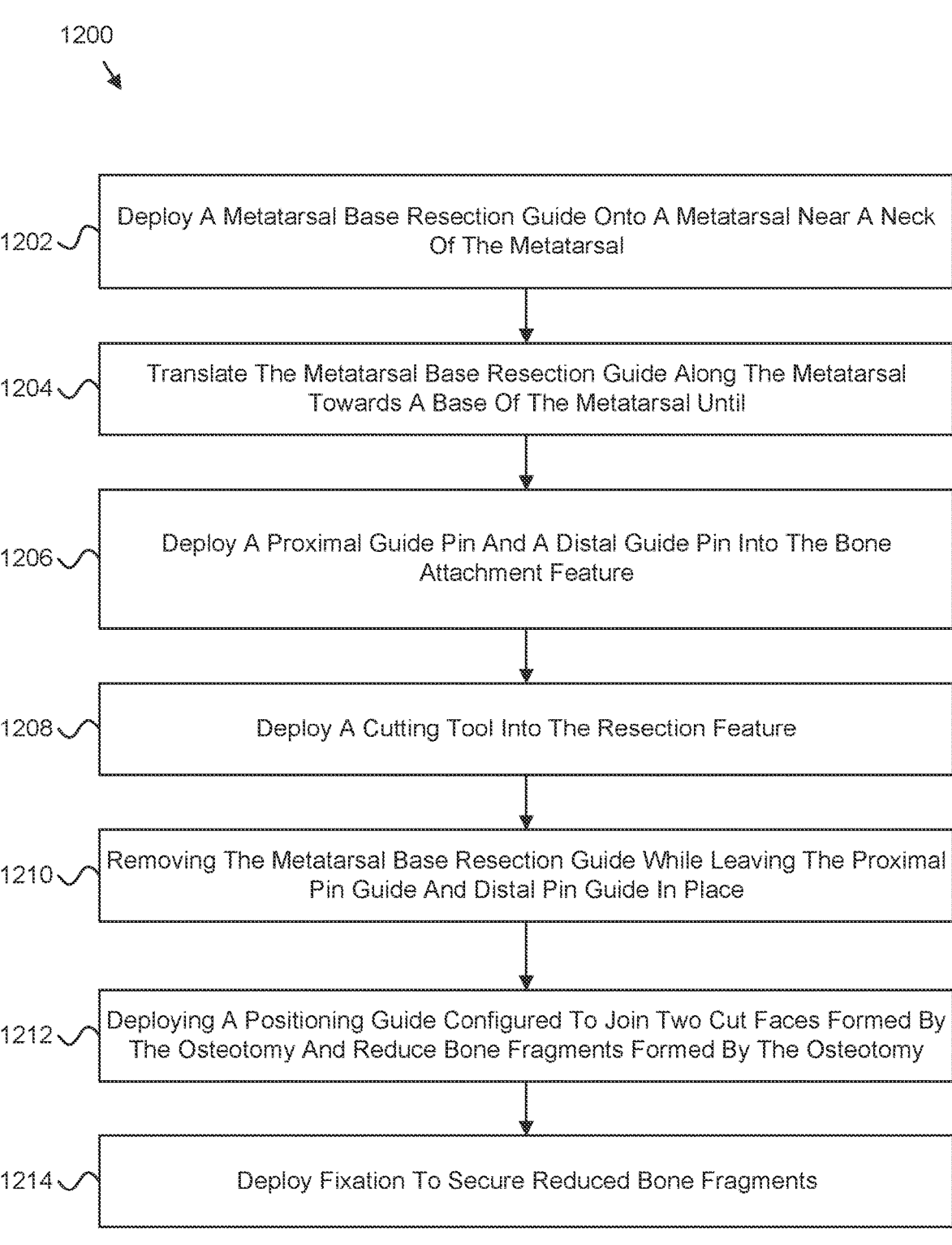

1200

1202 — Deploy A Metatarsal Base Resection Guide Onto A Metatarsal Near A Neck Of The Metatarsal 1204 — Translate The Metatarsal Base Resection Guide Along The Metatarsal Towards A Base Of The Metatarsal Until 1206 — Deploy A Proximal Guide Pin And A Distal Guide Pin Into The Bone Attachment Feature 1208 — Deploy A Cutting Tool Into The Resection Feature 1210 — Removing The Metatarsal Base Resection Guide While Leaving The Proximal Pin Guide And Distal Pin Guide In Place 1212 — Deploying A Positioning Guide Configured To Join Two Cut Faces Formed By The Osteotomy And Reduce Bone Fragments Formed By The Osteotomy 1214 — Deploy Fixation To Secure Reduced Bone Fragments

FIG. 12

APPARATUS, SYSTEM, AND METHOD FOR PATIENT-SPECIFIC METHODS AND INSTRUMENTATION

CROSS-REFERENCE TO RELATED APPLICATIONS

This application claims the benefit of U.S. Provisional Application No. 63/341,362, filed May 12, 2022, which is hereby incorporated by reference in its entirety.

TECHNICAL FIELD

The present disclosure relates to surgical devices, systems, instruments, and methods. More specifically, the present disclosure relates to patient-specific instruments, implants, instruments, and/or methods of designing and using the same.

BACKGROUND

Various bone conditions may be corrected using surgical procedures, in which one or more tendons, ligaments, and/or bones may be cut, replaced, repositioned, reoriented, reattached, fixated and/or fused. These surgical procedures require the surgeon to properly locate, position, and/or orient one or more osteotomy cuts, fixation guides, fixators, bone tunnels, points of attachment for ends of grafts or soft tissue and the like. Determining and locating an optimal location and trajectory for one or more steps of the surgical procedures and/or securing instruments that can guide or assist in steps of the surgical procedures such as performing osteotomies, deploying fixation, and the like, can be challenging, given conventional techniques and instruments. Furthermore, such surgical procedures can be extra challenging when working on anatomy such as bones of a patient's foot or hand which have much smaller bones that called for extra precision in comparison to larger bones such as a femur. What is needed is one or more instruments to facilitate locating, aligning, orienting, planning, preparing for, initiating, executing, and/or completing such surgical procedures. In addition, what is needed is methods, apparatus, implants and/or instrumentation that is customized to a specific patient. Existing solutions for guiding orthopedic surgical procedures are inadequate and error prone.

SUMMARY

The various apparatus, devices, systems, and/or methods of the present disclosure have been developed in response to the present state of the art, and in particular, in response to the problems and needs in the art that have not yet been fully solved by currently available technology.

One general aspect of the present disclosure may include an apparatus that may include a proximal end and a distal end. An apparatus that may furthermore include a body having a superior side, an inferior side, a medial side, a lateral side, a proximal side, and a distal side. An apparatus that may in addition include a resection feature between the proximal end and the distal end that guides resection of a metatarsal of a patient's foot.

An apparatus that may moreover include a bone attachment feature configured to couple the body to the metatarsal. An apparatus that may also include a bone engagement surface configured to register to the metatarsal based on medical imaging taken of the patient's foot.

Implementations may also include one or more of the following features. An apparatus where the bone engagement surface may include: a medial surface configured to contact a medial surface of the metatarsal; a lateral surface configured to contact a lateral surface of the metatarsal; and an intermediate surface between the medial surface and the lateral surface. The intermediate surface may be configured to contact a dorsal surface of the metatarsal. An apparatus where the body is configured to be pliable and the medial surface extends opposite the lateral surface such that deployment of the apparatus by driving the intermediate surface towards the dorsal surface causes the medial surface to slide along the metatarsal medial surface and the lateral surface to slide along the metatarsal lateral surface until the intermediate surface engages the metatarsal dorsal surface which results in the medial surface contacting the metatarsal medial surface and the lateral surface contacting the metatarsal lateral surface.

An apparatus where the bone engagement surface may include: a plantar surface configured to contact a plantar surface of the metatarsal; a dorsal surface configured to contact a dorsal surface of the metatarsal; and an intermediate surface between the plantar surface and the dorsal surface, the intermediate surface configured to contact a medial surface of the metatarsal. An apparatus where the bone engagement surface is configured to engage a metaphyseal diaphyseal junction (MDJ) of the metatarsal near a base of the metatarsal.

An apparatus where a configuration of the bone engagement surface is defined based on a prescription from a doctor.

An apparatus where the body may include a long axis and the resection feature may include: a proximal slot that extends from the superior side to the inferior side at a first angle relative to the long axis, the proximal slot having a first medial end and a first lateral end; a distal slot that extends from the superior side to the inferior side at a second angle relative to the long axis, the distal slot having a second medial end and a second lateral end; and where the first medial end and the second medial end are separated by a first distance and the first lateral end and the second lateral end are separated by a second distance. An apparatus where the first distance and the second distance are substantially the same. An apparatus where the first distance is shorter than the second distance. An apparatus where the first distance is substantially zero such that the proximal slot and distal slot connect at the first medial end and the second medial end and the proximal slot and distal slot are offset by a third angle measured within the transverse plane.

An apparatus where one of the first angle, the second angle, the third angle, the first distance, and the second distance are predetermined by a surgeon based on the medical imaging taken of the patient's foot. An apparatus where the first medial end of the proximal slot and the first medial end of the distal slot are offset by a third angle measured within the transverse plane and where at least one of the first angle, the second angle, the third angle, the first distance, and the second distance are defined for a correction having of a uniplanar correction, a biplanar correction, and a triplane correction.

An apparatus where the medial side of the body may include a medial inferior surface that meets the superior side at a medial edge, the medial inferior surface angled to connect the inferior side of the body and the medial edge such that the medial inferior surface provides clearance for a cutting tool inserted into the resection feature.

An apparatus where the bone attachment feature may include: a proximal hole that extends from the superior side to the inferior side of the body, the proximal hole configured to receive a proximal guide pin; a distal hole that extends from the superior side to the inferior side of the body, distal hole configured to receive a distal guide pin; and where the proximal hole extends into the body parallel and aligned with the distal hole. An apparatus where proximal hole and distal hole are configured to cooperate with the proximal guide pin and the distal guide pine to form anchor holes in the metatarsal for fixation deployed subsequent to use of the apparatus. An apparatus where the body may include a landmark registration feature that extends from the proximal side, the landmark registration feature having a probe configured to fit within a tarso-metatarsal (TMT) joint that includes the metatarsal.

An apparatus where the landmark registration feature may include a probe bone engagement surface configured to register to a part of a surface of the metatarsal between the TMT joint and a neck of the metatarsal.

One general aspect of the present disclosure may include a system that may include a metatarsal base resection guide having: a proximal end; a distal end; a body having a superior side, an inferior side, a medial side, a lateral side, a proximal side, and a distal side; a proximal slot that extends from the superior side to the inferior side at a first angle relative to a long axis of a metatarsal of a patient's foot, the proximal slot having a first medial end and a first lateral end, the proximal slot configured to guide resection of the metatarsal; a distal slot that extends from the superior side to the inferior side at a second angle relative to the long axis, the distal slot having a second medial end and a second lateral end, the distal slot configured to guide resection of the metatarsal; a landmark registration feature that extends from the proximal side of the body, the landmark registration feature having a probe bone engagement surface; a proximal hole that extends from the superior side to the inferior side of the body, the proximal hole configured to receive a proximal guide pin that cooperates with the proximal hole to secure the body to the metatarsal; a distal hole that extends from the superior side to the inferior side of the body, distal hole configured to receive a distal guide pin that cooperates with the distal hole to secure the body to the metatarsal; and a bone engagement opening that includes a bone engagement surface configured to register to a surface of the metatarsal based on medical imaging taken of the patient's foot.

A system that may also include a trajectory guide having: a body having: a head having: a proximal opening configured to receive the proximal guide pin deployed into the metatarsal; a distal opening configured to receive the distal guide pin deployed into the metatarsal. A system that may furthermore include a neck connected to the head. A system that may in addition include a base connected to the neck, the base having: at least one fastener opening configured to accept a fastener configured to secure a distal bone fragment on one side of an osteotomy formed using the metatarsal base resection guide to a proximal bone fragment on an opposite side of the osteotomy.

One general aspect of the present disclosure may include a method that may include deploying a metatarsal base resection guide onto a metatarsal near a neck or body of the metatarsal, the metatarsal base resection guide having: a body a proximal end and a distal end and having a superior side, an inferior side, a medial side, a lateral side, a proximal side, and a distal side; a resection feature between the proximal end and the distal end that guides resection of a metatarsal of a patient's foot; a bone attachment feature configured to couple the body to the metatarsal; and a bone engagement surface configured to register to the metatarsal based on medical imaging taken of the patient's foot.

A method that may also include translating the metatarsal base resection guide along the metatarsal towards a base of the metatarsal until a medial surface of the bone engagement surface engages a medial surface of the metatarsal, a lateral surface of the bone engagement surface engages a lateral surface of the metatarsal, and an intermediate surface of the bone engagement surface between the medial surface and the lateral surface form a friction fit between the medial surface, dorsal surface, and lateral surface of the metatarsal and the metatarsal base resection guide. A method that may furthermore include deploying a proximal guide pin and a distal pin guide into the bone attachment feature.

A method that may in addition include deploying a cutting tool into the resection feature of the metatarsal base resection guide to form an osteotomy of the metatarsal. A method that may moreover include removing the metatarsal base resection guide from the metatarsal while leaving proximal guide pin and distal guide pin in place. A method that may also include deploying a positioning guide configured to join two cut faces formed by the osteotomy and reduce bone fragments formed by the osteotomy. A method that may furthermore include deploying fixation to secure the reduced bone fragments of the osteotomy.

Implementations may also include one or more of the following features. A method where the metatarsal base resection guide may include a landmark registration feature and translating the metatarsal base resection guide along the metatarsal further may include translating the metatarsal base resection guide until a probe of the landmark registration feature seats within a tarso-metatarsal (TMT) joint that includes the metatarsal.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings.

FIG. 1A is a flowchart diagram depicting a method for remediating a condition, according to one embodiment.

FIG. 1B is a flowchart diagram depicting a method for remediating a condition, according to one embodiment.

FIG. 4 illustrates an exemplary system configured to generate one or more patient-specific instruments, according to one embodiment.

FIG. 12 is a flowchart diagram depicting a method for remediating a condition, according to one embodiment.

DETAILED DESCRIPTION

Figures 2A, 2B:
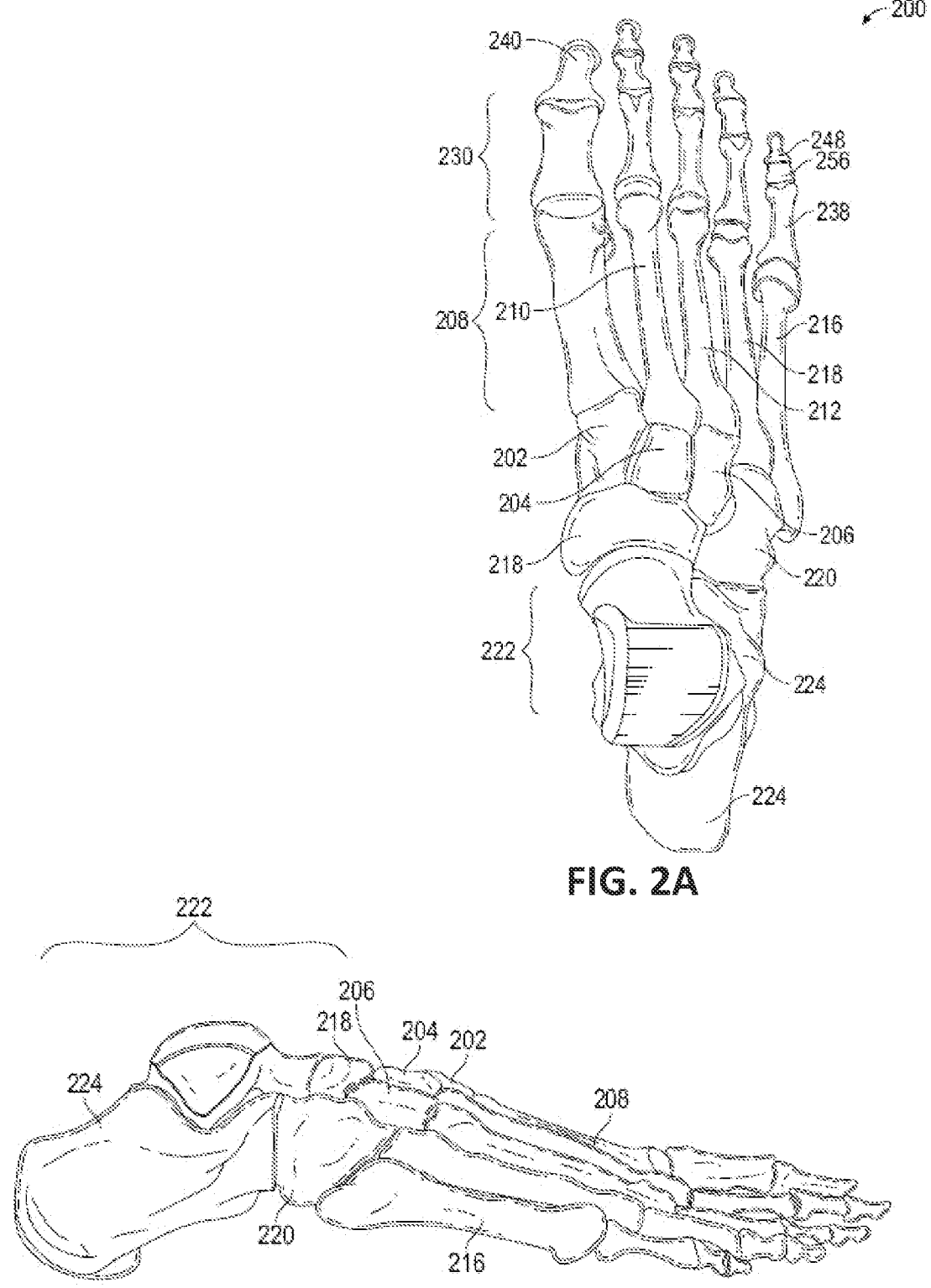
FIG. 2A is a dorsal perspective view of bones of a foot.
FIG. 2B is a lateral perspective view of bones of a foot.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

As used herein, "coupling", "coupling member", or "coupler" refers to a mechanical device, apparatus, member, component, system, assembly, or structure, that is organized, configured, designed, arranged, or engineered to connect, or facilitate the connection of, two or more parts, objects, or structures. In certain embodiments, a coupling can connect adjacent parts or objects at their ends. In certain embodiments, a coupling can be used to connect two shafts together at their ends for the purpose of transmitting power. In other embodiments, a coupling can be used to join two pieces of rotating equipment while permitting some degree of misalignment or end movement or both. In certain embodiments, couplings may not allow disconnection of the two parts, such as shafts during operation. (Search "coupling" on Wikipedia.com Jul. 26, 2021. CC-BY-SA 3.0 Modified. Accessed Jul. 27, 2021.) A coupler may be flexible, semiflexible, pliable, elastic, or rigid. A coupler may join two structures either directly by connecting directly to one structure and/or directly to the other or indirectly by connecting indirectly (by way of one or more intermediary structures) to one structure, to the other structure, or to both structures.

As used herein, a "marking" or "marker" refers to a symbol, letter, lettering, word, phrase, icon, design, color, diagram, indicator, figure, or combination of these designed, intended, structured, organized, configured, programmed, arranged, or engineered to communication information and/or a message to a user receiving, viewing, or encountering the marking. The marking can include one or more of a tactile signal, a visual signal or indication, an audible signal, and the like. In one embodiment, a marking may comprise a number or set letters, symbols, or words positioned on a surface, structure, color, color scheme, or device to convey a desired message or set of information.

"Patient specific" refers to a feature, an attribute, a characteristic, a structure, function, structure, device, guide, tool, instrument, apparatus, member, component, system, assembly, module, or subsystem or the like that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific attribute or feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, a trajectory for an instrument, implant, or anatomical part of a patient, a lateral offset, and/or other features.

"Patient-specific instrument" refers to an instrument, implant, or guide designed, engineered, and/or fabricated for use with a specific patient. In one aspect, a patient-specific instrument is unique to a patient and may include features unique to the patient such as a surface contour or other features.

"Patient-specific positioning guide" or "Patient-specific positioner" refers to an instrument, implant, positioner, structure, or guide designed, engineered, and/or fabricated for use as a positioner with a specific patient. In one aspect, a patient-specific positioning guide is unique to a patient and may include features unique to the patient such as patient-specific offsets, translation distances, openings, angles, orientations, anchor a surface contour or other features.

"Patient-specific cutting guide" refers to a cutting guide designed, engineered, and/or fabricated for use with a specific patient. In one aspect, a patient-specific cutting guide is unique to a patient and may include features unique to the patient such as a surface contour or other features.

"Patient-specific resection guide" refers to a guide designed, engineered, and/or fabricated for use in resection for a specific patient. In one aspect, a patient-specific resection guide is unique to a patient and may include features unique to the patient such as a surface contour or other features.

"Patient-specific trajectory guide" refers to a trajectory guide designed, engineered, and/or fabricated for use with a specific patient. In one aspect, a patient-specific trajectory guide is unique to a single patient and may include features unique to the patient such as a surface contour or other features.

"Patient specific instrument" (PSI) refers to a structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient. In certain aspects, one patient. In one aspect, a patient specific instrument is unique to a single patient and may include features unique to the patient such as a surface contour, component position, component orientation, and/or other features. In other aspects, one patient specific instrument may be useable with a number of patients having a particular class of characteristics.

As used herein, a "handle" or "knob" refers to a structure used to hold, control, or manipulate a device, apparatus, component, tool, or the like. A "handle" may be designed to be grasped and/or held using one or two hands of a user. In certain embodiments, a handle or knob may be an elongated structure. In one embodiment, a knob may be a shorter stubby structure.

As used herein, "implant" refers to a medical device manufactured to replace a missing biological structure, support a damaged biological structure, or enhance an existing biological structure. Often medical implants are man-made devices, but implants can also be natural occurring structures. The surface of implants that contact the body may be made of, or include a biomedical material such as titanium, cobalt chrome, stainless steel, carbon fiber, another metallic alloy, silicone, polymer, Synthetic polyvinyl alcohol (PVA) hydrogels, biomaterials, biocompatible polymers such as PolyEther Ether Ketone (PEEK) or a polylactide polymer (e.g. PLLA) and/or others, or apatite, or any combination of these depending on what is functional and/or economical. Implants can have a variety of configurations and can be wholly, partially, and/or include a number of components that are flexible, semiflexible, pliable, elastic, supple, semi-rigid, or rigid. In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants can be used to treat bone fractures, osteoarthritis, scoliosis, spinal stenosis, discomfort, and pain. Examples of orthopedic implants include, but are not limited to, a wide variety of pins, rods, screws, anchors, spacers, sutures, all-suture implants, ball all-suture implants, self-locking suture implants, cross-threaded suture implants, plates used to anchor fractured bones while the bones heal or fuse together, and the like. (Search "implant (medicine)" on Wikipedia.com May 26, 2021. CC-BY-SA 3.0 Modified. Accessed Jun. 30, 2021.)

As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

As used herein, "bone engagement surface" refers to a surface of an object, instrument, or apparatus, such as an implant that is oriented toward or faces one or more bones of a patient. In one aspect, the bone engagement surface may abut, touch, or contact a surface of a bone. In another aspect, the bone engagement surface or parts of the bone engagement surface may be close to, but not abut, touch, or contact a surface of the bone. In certain aspects, the bone engagement surface can be configured to engage with a surface of one or more bones. Such a bone engagement surface may include projections and recesses that correspond to and match projections and recesses of the one or more bone surfaces.

As used herein, "side" refers to a structure or part of a structure including, but not limited to: one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021. Web. 3 Aug. 2021. Modified.) A side can also refer to a geometric edge of a polygon (two-dimensional shape) and/ or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure. As used herein, the term "side" can include one or more modifiers that define and/or orient and/or distinguish the side of an object from others based on based on where and/or how the object is deployed within or in relation to a second object. For example, in the context of an implant for a patient, sides of the implant may be labeled based on where the sides are relative to the patient when the implant is deployed. As one example, an "anterior side" of an implant refers to a side that is anterior to other sides of the implant in relation to a patient when the implant is deployed in the patient. As another example, in the context of an instrument used with a patient, sides of the instrument may be labeled based on where the sides are when the instrument is being used for its purpose. As one example, a "front side" of an instrument refers to a side that is facing a user of the instrument when the instrument is in use.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, articulations of foot, and the like. (Search "joint" on Wikipedia.com Dec. 19, 2021. CC-BY-SA 3.0 Modified. Accessed Jan. 20, 2022.)

"Topographical" refers to the physical distribution of parts, structures, or features on the surface of, or within, an organ or other anatomical structure, or organism. (Search "define topographical" on google.com. Oxford Languages, Copyright 2022. Oxford University Press. Web., Modified. Accessed 15 Feb. 2022.)

"Landmark registration features" or "Landmark" refers to a structure configured to engage with a feature, aspect, attribute, or characteristic of a first object to orient and/or position a second object that includes the landmark registration feature with respect to the first object. A variety of structures can serve as a landmark registration feature. For example, a landmark registration feature may include a protrusion, a projection, a tuberosity, a cavity, a void, a divot, a tab, an extension, a hook, a curve, or the like. In the context of bones of a patient a landmark registration feature can include any protuberance, void, divot, concave section, sesamoid, bone spur or other feature on, or extending from, a bone of a patient.

"Probe bone engagement surface" refers to a bone engagement surface on one surface of a probe or part of a probe.

"Bone attachment feature" refers to a structure, feature, component, aspect configured to securely connect, couple, attach, and/or engage a structure, component, object, or body with a bone and/or a bone fragment. Examples of a bone attachment feature, include, but are not limited to, a pin, K-wire, screw, or other fastener alone, or in combination with, a hole, passage, and/or opening.

As used herein, "patient-specific osteotomy procedure" refers to an osteotomy procedure that has been adjusted, tailored, modified, or configured to specifically address the needs or desires or a particular patient. In certain aspects, one patient-specific osteotomy procedure may be useable in connection with only one patient. In other aspects, one patient-specific osteotomy procedure may be useable with a number of patients having a particular class of characteristics.

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like.

In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft.

In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like.

As used herein, an "anchor" refers to an apparatus, instrument, structure, member, part, device, component, system, or assembly structured, organized, configured, designed, arranged, or engineered to secure, retain, stop, and/or hold, an object to or at a fixed point, position, or location. Often, an anchor is coupled and/or connected to a flexible member such as a tether, chain, rope, wire, thread, suture, suture tape, or other like object. Alternatively, or in addition, an anchor may also be coupled, connected, and/or joined to a rigid object or structure. In certain embodiments, an anchor can be a fixation device. Said another way, a fixation device can function as an anchor. In certain embodiments, the term anchor may be used as an adjective that describes a function, feature, or purpose for the noun the adjective 'anchor' describes. For example, an anchor hole is a hole that serves as or can be used asn an anchor.

"Connector" refers to any structure configured, engineered, designed, adapted, and/or arranged to connect one structure, component, element, or apparatus to another structure, component, element, or apparatus. A connector can be rigid, pliable, elastic, flexible, and/or semiflexible. Examples of a connector include but are not limited any fastener.

"Clearance" refers to a space or opening that provides an unobstructed area to permit one object to move freely in relation to another object.

"Correction," in a medical context, refers to a process, procedure, device, instrument, apparatus, system, implant, or the like that is configured, designed, developed, fabricated, configured, and/or organized to adjust, translate, move, orient, rotate, or otherwise change an anatomical structure from an original position, location, and/or orientation to a new position, location, and/or orientation that provides a benefit to a patient. The benefit may be one of appearance, anatomical function, pain relieve, increased mobility, increased strength, and the like.

"Uniplanar correction" refers to a medical correction, which can include an osteo correction, in one plane (e.g., one of a sagittal plane, a transverse plane, and a coronal/frontal plane) of an anatomical structure such as a foot, hand, or body of a patient.

"Biplanar correction" refers to a medical correction, which can include an osteo correction, in two planes (e.g., two of a sagittal plane, a transverse plane, and a coronal/frontal plane) of an anatomical structure such as a foot, hand, or body of a patient.

"Triplane correction" refers to a medical correction, which can include an osteo correction, in three planes (e.g., all three planes of a sagittal plane, a transverse plane, and a coronal/frontal plane) of an anatomical structure such as a foot, hand, or body of a patient.

"Probe" refers to a medical instrument used to explore, identify, locate, or register to, wounds, organs, and/or anatomical structures including a joint or an articular surface. In certain embodiments, a probe can be thin and/or pointed. In one embodiment, a probe is connected, integrated with, and/or coupled to another structure or instrument. In such an embodiment, the probe may serve to facilitate proper positioning of the another structure or instrument. For example, the probe may be used to identify and/or locate a particular anatomical structure and the positioning of the probe may then cause the connected structure or instrument to also be positioned in a desired location relative to one or more anatomical structures.

As used herein, "manufacturing tool" or "fabrication tool" refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

"Friction fit" refers to a type of joint or connection that is created between two components by means of friction. A joint or connection that is formed using a friction fit may or may not include the use of additional fasteners such as screws, bolts, or adhesives. In a friction fit, the components are designed or configured to fit tightly together, creating enough friction between the surfaces to hold them securely in place, at least temporarily. The friction force is generated by the compressive force that experienced between the components, and can be strong enough to prevent components from separating under normal conditions. (© ChatGPT March 23 Version, Modified, accessed chat.openai.com/chat May 2, 2023).

As used herein, "osteotomy procedure" or "surgical osteotomy" or "osteotomy" refers to a surgical operation in which one or more bones are cut to shorten or lengthen them or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.) As used herein, "patient-specific osteotomy procedure" refers to an osteotomy procedure that has been adjusted, tailored, modified, or configured to specifically address the anatomy, physiology, condition, abnormalities, needs, or desires of a particular patient. In certain aspects, one patient-specific osteotomy procedure may be useable in connection with only one patient. In other aspects, one patient-specific osteotomy procedure may be useable with a number of patients having a particular class of characteristics. In certain aspects, a patient-specific osteotomy procedure may refer to a non-patient-specific osteotomy procedure that includes one or more patient-specific implants and/or instrumentation. In another aspects, a patient-specific osteotomy procedure may refer to a patient-specific osteotomy procedure that includes one or more patient-specific implants, patient-specific surgical steps, and/or patient-specific instrumentation.

"Wedge osteotomy" refers to an osteotomy procedure in which one or more wedges are used as part of the procedure. Generally, wedge osteotomies can be of one of two types, open wedge and closing wedge. The type of osteotomy refers to how the procedure changes the relation between two parts of a bone involved in the osteotomy. In an open wedge osteotomy a wedge of bone or graft or other material is inserted in between two parts of a bone. Consequently, a wedge shape is "opened" in the bone. In a close wedge osteotomy or closing wedge osteotomy a wedge of bone is removed from a bone. Consequently, a wedge shape formed in the bone is "closed."

"Metatarsal" is a bone of a foot of a human or animal. In a human, a foot typically includes five metatarsals which are identified by number starting from the most medial metatarsal, which is referred to as a first metatarsal and moving laterally the next metatarsal is the second metatarsal, and the naming continues in like manner for the third, fourth, and fifth metatarsal. The metatarsal bone includes three parts a base which is a part that is at a proximal end of the metatarsal, a head which is a part that is at a distal end of the metatarsal, and a shaft or neck connects the base to the head.

"Epiphyses" refers to the rounded end of a long bone, at long bone's joint with adjacent bone(s). Between the epiphysis and diaphysis (the long midsection of the long bone) lies the metaphysis, including the epiphyseal plate (growth plate). At the joint, the epiphysis is covered with articular cartilage; below that covering is a zone similar to the epiphyseal plate, known as subchondral bone. (Search 'epiphysis' on Wikipedia.com 17 Jun. 2022. Modified. Accessed Aug. 1, 2022.) "Metaphysis" refers to the neck portion of a long bone between the epiphysis and the diaphysis. The metaphysis contains the growth plate, the part of the bone that grows during childhood, and as the metaphysis grows the metaphysis ossifies near the diaphysis and the epiphyses. (Search 'metaphysis' on Wikipedia.com 17 Jun. 2022. Modified. Accessed Aug. 1, 2022.) "Diaphysis" refers to the main or midsection (shaft) of a long bone. The diaphysis is made up of cortical bone and usually contains bone marrow and adipose tissue (fat). The diaphysis is a middle tubular part composed of compact bone which surrounds a central marrow cavity which contains red or yellow marrow. In diaphysis, primary ossification occurs. (Search 'diaphysis' on Wikipedia.com 17 Jun. 2022. Modified. Accessed Aug. 1, 2022.)

"Metaphyseal Diaphyseal Junction" or "MDJ" refers to an area of a long bone between the Metaphysis and the Diaphysis. This area can also include or be referred to as the epiphyseal plate (growth) plate. For certain surgical procedures, performing an osteotomy at or near the metaphyseal diaphyseal junction may be advantageous and desirable to promote rapid fusion of two cut faces formed in the osteotomy and bone growth to close the osteotomy, and/or may mitigate the risk of a nonunion of the osteotomy.

As used herein, a "base" refers to a main or central structure, component, or part of a structure. A base is often a structure, component, or part upon which, or from which other structures extend into, out of, away from, are coupled to, or connect to. A base may have a variety of geometric shapes and configurations. A base may be rigid or pliable. A base may be solid or hollow. A base can have any number of sides. In one embodiment, a base may include a housing, frame, or framework for a larger system, component, structure, or device. In certain embodiments, a base can be a part at the bottom or underneath a structure designed to extend vertically when the structure is in a desired configuration or position. Certain bones such as a metatarsal bone can include a base as one structural component of the bone.

As used herein, "anatomic data" refers to data identified, used, collected, gathered, and/or generated in connection with an anatomy of a human or animal. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

A bone model or anatomic model of a patient's body or body part(s) may be generated by computing devices that analyze medical imaging images. Structures of a patient's body can be determined using a process called segmentation.

"Positioner" or "positioning guide" refers to any structure, apparatus, surface, device, system, feature, or aspect configured to position, move, translate, manipulate, or arrange one object in relation to another. In certain embodiments, a positioner can be used for one step in surgical procedure to position, arrange, orient, and/or reduce one bone or bone fragment relative to another. In such embodiments, the positioner may be referred to as a bone positioner. In certain embodiments, the term positioner or positioning guide may be preceded by an adjective that identifies the structure, implement, component, or instrument that may be used with, positioned by, and/or guided by with the positioner. For example, a "pin positioner" may be configured to accept a pin or wire such as a K-wire and serve to position or place the pin relative to another structure such as a bone.

"Reduction guide" or "reducer" refers to any structure, apparatus, surface, device, system, feature, or aspect configured, designed, engineered, or fabricated to reduce or aide a user in the reduction of one bone or bone fragment or implant in relation to another bone or bone fragment or implant.

"Rotation guide" or "rotator" refers to any structure, apparatus, surface, device, system, feature, or aspect configured, designed, engineered, or fabricated to rotate or aide a user in the rotation of one structure relative to another structure. In certain embodiments, a rotation guide or rotator may be used to help a surgeon rotate one or more bones, parts of bones, bone fragment, an implant, or other anatomical structure, either alone or in relation to another one or more bones, parts of bones, bone fragments, implants, or other anatomical structures.

"Trajectory guide" or "trajectory indicator" or "targeting guide" refers to any structure, apparatus, surface, device, system, feature, or aspect configured to indicate, identify, guide, place, position, or otherwise assist in marking or deploying a fastener or other structure along a desired trajectory for one or more subsequent steps in a procedure.

"Metatarsal base resection guide" refers to a resection guide designed, engineered, fabricated, or intended for use with, one, in, or about a base part, section, surface, portion, or aspect of a metatarsal for one or more steps of a medical procedure. The metatarsal base resection guide may be used to form an osteotomy, to resect a wedge for a closing wedge procedure, resect a bone wedge that preserves a cortical layer of bone opposite the resected bone wedge, form an osteotomy that uniplanar wedge, a biplanar wedge, or a triplane wedge. Various embodiments of a metatarsal base resection guide may be used on a medial surface, a dorsal surface, a lateral surface, or a plantar surface of a single metatarsal. Alternatively, or in addition, various embodiments of a metatarsal base resection guide can be used on two or more metatarsals.

As used herein, a "guard" refers to an apparatus, instrument, structure, member, device, component, system, or assembly structured, organized, configured, designed, arranged, or engineered to prevent, limit, impede, stop, or restrict motion, action, or movement and/or operation of the another object, member, structure, component, part, apparatus, system, or assembly beyond a certain parameter such as a boundary. Said another way, a "guard" refers to an apparatus, instrument, structure, member, device, component, system, or assembly structured, organized, configured, designed, arranged, or engineered to retain, maintain, hold, keep, or restrict motion, action, or movement and/or operation of the another object, member, structure, component, part, apparatus, system, or assembly within or at one or more parameters such as a boundary.

As used herein, "artificial intelligence" refers to intelligence demonstrated by machines, unlike the natural intelligence displayed by humans and animals, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.)

As used herein, "segmentation" or "image segmentation" refers the process of partitioning an image into different meaningful segments. These segments may correspond to different tissue classes, organs, pathologies, bones, or other biologically relevant structures. Medical image segmentation accommodates imaging ambiguities such as by low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while non-parametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. In certain embodiments bone imaging includes devices that scan and gather bone density anatomic data. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data.

DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo. These two technologies include the transformation of computational models to represent specific subjects/patients, thus paving the way for personalized computational models. Individualization of generic computational models through imaging can be realized in three complementary directions: definition of the subject-specific computational domain (anatomy) and related subdomains (tissue types); definition of boundary and initial conditions from (dynamic and/or functional) imaging; and characterization of structural and functional tissue properties. Medical imaging and medical image computing enable in the translation of models to the clinical setting with both diagnostic and therapeutic applications. (Id.) In certain embodiments, medical image computing can be used to generate a bone model, a patient-specific model, and/or a patent specific instrument from medical imaging and/or medical imaging data.

As used herein, "model" refers to an informative representation of an object, person or system. Representational models can be broadly divided into the concrete (e.g. physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.) As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as an implant together with the pores and/or lattices can be directly manufactured (without the need to generate molds, tool paths, perform any milling, and/or other manufacturing steps).

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

As used herein, a "sleeve" refers to structure that is narrow and longer longitudinally than the structure is wide. In certain embodiments, a sleeve serves to surround, enclose, wrap, and/or contain something else. In certain embodiments, a sleeve may surround, enclose, wrap, and/or contain a passage or void. (Search "sleeve" on wordhippo.com. Word Hippo, 2021. Web. Accessed 15 Nov. 2021. Modified.) In certain embodiments, the term sleeve may be preceded by an adjective that identifies the structure, implement, component or instrument that may be used with, inserted into or associated with the sleeve. For example, a "pin sleeve" may be configured to accept a pin or wire such as a K-wire, a "drive sleeve" may be configured to accept a drill or drill bit, a "fixation member sleeve" may be configured to accept a fastener or fixation member.

As used herein, "image registration" refers to a method, process, module, component, apparatus, and/or system that seeks to achieve precision in the alignment of two images. As used here, "image" may refer to either or both an image of a structure or object and another image or a model (e.g., a computer based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. There may be several considerations made when performing image registration: The transformation model. Common choices are rigid, affine, and deformable transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures.

Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed. (Search "medical image computing" on Wikipedia.com Jun. 24, 2021. CC-BY-SA 3.0 Modified. Accessed Jun. 25, 2021.)

"Register" or "Registration" refers to an act of aligning, mating, contacting, engaging, or coupling one or more parts and/or surfaces of one object in relation to one or more parts and/or surfaces of another object. Often, the one or more parts and/or surfaces one object include protrusions and/or depressions that are the inverse or mirror configuration of protrusions and/or depressions of one or more parts and/or surfaces of the other object.

As used herein, a "resection" refers to a method, procedure, or step that removes tissue from another anatomical structure or body. A resection is typically performed by a surgeon on a part of a body of a patient. A resection is one type of osteotomy. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is resected.

"Bone condition" refers to any of a variety of conditions of bones of a patient. Generally, a bone condition refers to an orientation, position, and/or alignment of one or more bones of the patient relative to other anatomical structures of the body of the patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). Alternatively, or in addition, "bone condition" can refer to the structural makeup and configuration of one or more bones of a patient. Thus bone condition may refer to a state or condition of regions, a thickness of a cortex, bone density, a thickness and/or porosity of internal regions (e.g. whether it is calcaneus or solid) of the bone or parts of the bone such as a head, a base, a shaft, a protuberance, a process, a lamina, a foramen, and the like of a bone, along the metaphyseal region, epiphysis region, and/or a diaphyseal region. "Malrotation" refers to a condition in which a part, typically a part of a patient's body has rotated from a normal position to an unnormal or uncommon position.

As used herein, a "guide" refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, a placement, deployment, or insertion guide that guides or directs the placement, positioning, orientation, deployment, installation, or insertion of a fastener and/or implant, a "cross fixation guide" that guides deployment of a fastener or fixation member, an "alignment guide" that guides the alignment of two or more objects or structures, a "resection guide" that serves to guide resection of soft or hard tissue, such as in an osteotomy, a "reduction guide" can serve to guide reduction of one or more bone segments or fragments, an "placement guide" that serves to identify how an object can be placed in relation to another object or structure, and the like. Furthermore, guides may include modifiers applied due to the procedure or location within a patient for which the guide is to be used. For example, where a guide is used at a joint, the guide may be referred to herein as an "arthrodesis guide".

As used herein, "feature" refers to a distinctive attribute or aspect of something. (Search "feature" on google.com. Oxford Languages, 2021. Web. 20 Apr. 2021.) A feature may include one or more apparatuses, structures, objects, systems, sub-systems, devices, or the like. A feature may include a modifier that identifies a particular function or operation and/or a particular structure relating to the feature. Examples of such modifiers applied to a feature, include, but are not limited to, "attachment feature," "securing feature," "placement feature," "protruding feature," "engagement feature," "disengagement feature," "resection feature", "guide feature", and the like.

Those of skill in the art will appreciate that a resection feature may take a variety of forms and may include a single feature or one or more features that together form the resection feature. In certain embodiments, the resection feature may take the form of one or more slots or cut channels. Alternatively, or in addition, a resection feature may be referenced using other names including, but not limited to, channel, cut channels, and the like.

"Cut channel" refers to a channel, slot, hole, or opening, configured to facilitate making a cut. In certain embodiments, a cut channel is one example of a resection feature, resection member, and/or resection guide. "Rotation slot" refers to a channel, slot, hole, or opening, configured to facilitate rotating one structure in relation to another structure.

As used herein, "slot" refers to a narrow opening or groove. (search "slot" on Merriam-Webster.com. Merriam-Webster, 2021. Web. 4 Aug. 2021. Modified.)

"Hole" refers to a gap, an opening, an aperture, a port, a portal, a space or recess in a structure, a void in a structure, or the like. In certain embodiments, a hole can refer to a structure configured specifically for receiving something and/or for allowing access. In certain embodiments, a hole can pass through a structure. In other embodiments, an opening can exist within a structure but not pass through the structure. A hole can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "hole" can include one or more modifiers that define specific types of "holes" based on the purpose, function, operation, position, or location of the "hole." As one example, a "fastener hole" refers to an "hole" adapted, configured, designed, or engineered to accept or accommodate a "fastener."

As used herein, an "opening" refers to a gap, a hole, an aperture, a port, a portal, a slit, a space or recess in a structure, a void in a structure, or the like. In certain embodiments, an opening can refer to a structure configured specifically for receiving something and/or for allowing access. In certain embodiments, an opening can pass through a structure. In such embodiments, the opening can be referred to as a window. In other embodiments, an opening can exist within a structure but not pass through the structure. In other embodiments, an opening can initiate on a surface or at an edge or at a side of a structure and extend into the structure for a distance, but not pass through or extend to another side or edge of the structure. In other embodiments, an opening can initiate on a surface or at an edge or at a side of a structure and extend into the structure until the opening extends through or extends to another side or edge of the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Cortical bone" refers to a type of bone tissue. Cortical bone is a type of bone tissue typically found between an external surface of a bone and an interior area of the bone. Cortical bone is more dense and typically stronger structurally than other types of bone tissue. "Cortical surface" refers to a surface of cortical bone.

"Cortex" refers to an area of bone that extends from an external surface of the bone towards a center part of the bone. The cortex is typically comprised of cortical bone.

"Capital fragment" refers to a distal end of a metatarsal or other long bone has been separated from the metatarsal or other long bone by an osteotomy. Typically, the capital fragment includes at least a portion of, or all of a head of the metatarsal or other long bone.

"Transosseous placement feature" refers to a placement feature that extends through one or more bones and that enables, or facilitates, placement of another device, apparatus, or instrument.

"Patient specific feature" refers to a feature, function, structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, and/or other features. "Medial resection guide" refers to a resection guide designed, engineered, fabricated, or intended for use with, one, in, or about a medial part, section, surface, portion, or aspect of an anatomical structure such as a bone, digit, limb, or other anatomical structure for one or more steps of a resection procedure. "Lateral resection guide" refers to a resection guide designed, engineered, fabricated, or intended for use with, one, in, or about a lateral part, section, surface, portion, or aspect of an anatomical structure such as a bone, digit, limb, or other anatomical structure for one or more steps of a resection procedure.

"Prescription" or "Prescribed" refers to a written order, as by a physician or nurse practitioner, for the administration of a medicine, preparation of an implant, preparation of an instrument, or other intervention. Prescription can also refer to the prescribed medicine or intervention. (Search "prescription" on wordhippo.com. WordHippo, 2023. Web. Accessed 3 May 2023. Modified.)

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

As used herein, "edge" refers to a structure, boundary, or line where an object, surface, or area begins or ends. An edge can also refer to a boundary or perimeter between two structures, objects, or surfaces. An edge can also refer to a narrow part adjacent to a border. (search "edge" on Merriam-Webster.com. Merriam-Webster, 2021. Web. 3 Aug. 2021. Modified.) In certain embodiments, an edge can be a one dimensional or a two dimensional structure that joins two adjacent structures or surfaces. Furthermore, an edge may be at a perimeter of an object or within a perimeter or boundary of an object.

"Bone fragment" refers to a part of a bone that is normally part of another bone of a patient. A bone fragment may be separate from another bone of a patient due to a deformity or trauma. In one aspect, the bone the bone fragment is normally connected or joined with is referred to as a parent bone.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, ankle joints, articulations of foot, and the like. (Search "joint" on Wikipedia.com Dec. 19, 2021. CC-BY-SA 3.0 Modified. Accessed Jan. 20, 2022.)

"Tarso-metatarsal joint" or "TMT joint" refers to a joint of a patient between a metatarsal bone and one or more cuneiform/tarsal/cuboid bones. The TMT joint may also be referred to as a "Lis Franc" or "Lisfranc" joint after a French surgeon Lisfranc.

"Cut surface" refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface(s) are planar.

"Orientation" refers to a direction, angle, position, condition, state, or configuration of a first object, component, part, apparatus, system, or assembly relative to another object, component, part, apparatus, system, assembly, reference point, reference axis, or reference plane.

"Longitudinal axis" or "Long axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point.

"Cutting tool" refers to any tool that can be used to cut or resect another object. In particular, a cutting tool can refer to a manual or power tool for cutting or resecting tissue of a patient. Examples, of cutting tools include, but are not limited to, a burr, an oscillating saw, a reciprocating saw, a grater saw, a drill, a mill, a side-cutting burr, or the like.

The present disclosure discloses surgical systems and methods by which a bone condition, that can include a deformity, may be corrected or otherwise addressed. Known methods of addressing bone conditions are often limited to a finite range of discretely sized instruments. A patient with an unusual condition, or anatomy that falls between instrument sizes, may not be readily treated with such systems.

Furthermore, patient-specific instruments may be used for various other procedures on the foot, or on other bones of the musculoskeletal system. For example, patient-specific instruments and/or other instruments may be used for various procedures including resection and translation of a head of a long bone, determining where to perform an osteotomy on one or more joints or part of one or more bones, determining ligament or tendon attachment or anchoring points, determining where to form bone tunnels or position anchors, tendon or graft deployment, and the like.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may include capturing a scan of only the particular bone(s) to be treated, or may include capture of additional anatomic information, such as the surrounding tissues. Additionally or alternatively, the step 102 may include receiving a previously captured image, for example, at a design and/or fabrication facility. Performance of the step 102 may result in possession of a three-dimensional model of the patient's anatomy, or three-dimensional surface points that can be used to construct such a three-dimensional model.

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis system, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan, and generate one or more instruments that are matched specifically to the size and/or shape of the patient's bone(s). In some embodiments, such instrumentation may include a targeting guide, trajectory guide, drill guide, cutting guide, tendon trajectory guide, capital fragment positioning guide, or similar guide that can be attached to one or more bones, with one or more features that facilitate work on the one or more bones pursuant to a procedure such as arthroplasty or arthrodesis. In some embodiments, performance of the step 106 may include modelling an instrument with a bone engagement surface that is shaped to match the contour of a surface of the bone, such that the bone engagement surface can lie directly on the corresponding contour.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a targeting guide, trajectory guide, drill guide, cutting guide, positioner, positioning guide, tendon trajectory guide, or the like.

In addition to, or in the alternative to the step 108, the model(s) may be used to select from available sizes of implants and/or instruments or instruments having various attributes and advise the surgeon accordingly. For example, where a range of guides are available for a given procedure, analysis of the CAD data may facilitate pre-operative selection of the optimal guide and/or optimal placement of the guide on the bone. Similarly, if a range of implants and/or instruments may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument(s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may include placing the modelled bone engagement surface against the corresponding contour of the bone used to obtain its shape, and then using the resection feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One example of the method 100 will be shown and described in connection with FIG. 1B, for correction of a bunion deformity of the foot.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, advanced computer analysis system, machine learning and automated/artificial intelligence may be used to generate a CAD model and/or one or more patient-specific instruments and/or operation plans. For example, a patient-specific instrument may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g. one or more bones of a patient's foot). Next, the patient-specific instrument and the patient-specific synthetic cadaver can be provided to a surgeon who can then rehearse an operation procedure in part or in full before going into an operating room with the patient.

In certain embodiments, the patient-specific instrument or instrument can be used to preposition and/or facilitate pre-drilling holes for a plate system for fixation purposes. Such plate systems may be optimally placed, per a CT scan, after a correction procedure for optimal fixation outcome. In another embodiment, the CAD model and/or automated process such as advanced computer analysis, machine learning and automated/artificial intelligence may be used to measure a depth of the a through a patient-specific resection guide for use with robotics apparatus and/or systems which would control the depth of each cut within the guide to protect vital structures below or adjacent to a bone being cut. In another embodiment, the CAD model and/or automated process such as advanced computer analysis, machine learning and automated/artificial intelligence may be used to define desired fastener (e.g. bone screw) length and/or trajectories through a patient-specific instrument and/or implant. The details for such lengths, trajectories, and components can be detailed in a report provided to the surgeon preparing to perform a procedure.

FIG. 1B is a flowchart diagram depicting a method 120 for correcting or remediating a bone condition, according to one embodiment. The method 120 may be used to prepare for an orthopedic procedure which corrects or remediates a bone, muscle, and/or tendon condition of a patient.

As shown, the method 120 may begin with a step 122 in which a CT scan (or another three-dimensional image) of the patient's foot is obtained. The step 122 may include capturing a scan of select bones of a patient or may include capturing additional anatomic information, such as the entire foot. Additionally or alternatively, the step 122 may include receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct or remediate a bone condition. Such instrumentation may include a guide. In one example, the guide can seat or abut or contact a surface of a bone and including an opening that guides a trajectory for a fastener for a procedure. In some embodiments, performance of the step 126 may include modelling the guide with a bone engagement surface that is shaped to match contours of the surfaces of the bone, such that the bone engagement surface can lie directly on the corresponding contours of the bone.

In a step 128, the model(s) may be used to manufacture patient-specific instrumentation and/or instruments. This may include manufacturing an instrument with the bone engagement surface and/or other features as described above. As in the step 108, the step 128 may additionally or alternatively involve provision of one or more instruments and/or implants from among a plurality of predetermined configurations or sizes. Further, the step 128 may additionally, or alternatively, involve provision of instructions for placement and/or anchorage of one or more instruments and/or instruments to carry out the procedure.

In a step 130, the manufactured instrument may be used in surgery to facilitate treatment of the condition. In certain embodiments, a bone engagement surface of the instrument may be placed against the corresponding contours of the bone. The instrument may include an opening and/or trajectory guide to guide insertion of a trajectory guide such as a temporary fastener such as a K-wire. The instrument may then be removed, and the remaining steps of a surgical procedure performed.

Method 100 and method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with the present disclosure. Those of skill in the art will recognize that the method 120 may be used in connection with different instruments; likewise, the instruments of the present disclosure may be used in connection with methods different from the method 100 and the method 120.

FIG. 2A is a perspective dorsal view of a foot 200. The foot 200 may have a medial cuneiform 202, an intermediate cuneiform 204, lateral cuneiform 206, a first metatarsal 208, a second metatarsal 210, third metatarsal 212, fourth metatarsal 214, fifth metatarsal 216, navicular 218, cuboid 220, talus 222, and calcaneus 224, among others. The medial cuneiform 202 and the intermediate cuneiform 204 may be joined together at a first metatarsocuneiform joint, and the first metatarsal 208 and the second metatarsal 210 may be joined together at a second metatarsocuneiform joint. The foot 200 includes a set of proximal phalanges numbered first through fifth (230, 232, 234, 236, 238) and a set of distal phalanges numbered first through fifth (240, 242, 244, 246, 248) and a set of middle phalanges numbered second through fifth (250, 252, 254, 256).

FIG. 2B is a perspective lateral view of a foot 200, with bones of the foot labeled.

Figure 2C:
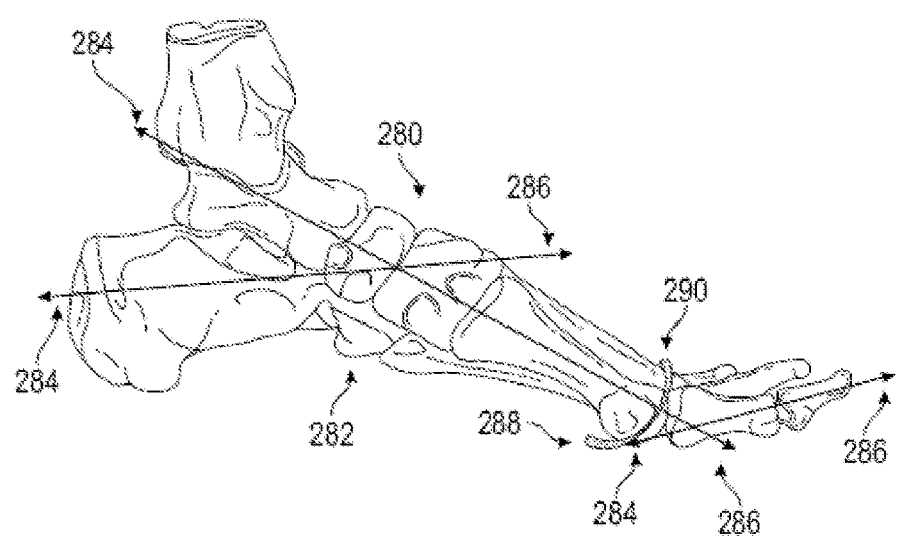
FIG. 2C is a medial perspective view of bones of a foot.
Figure 2D:
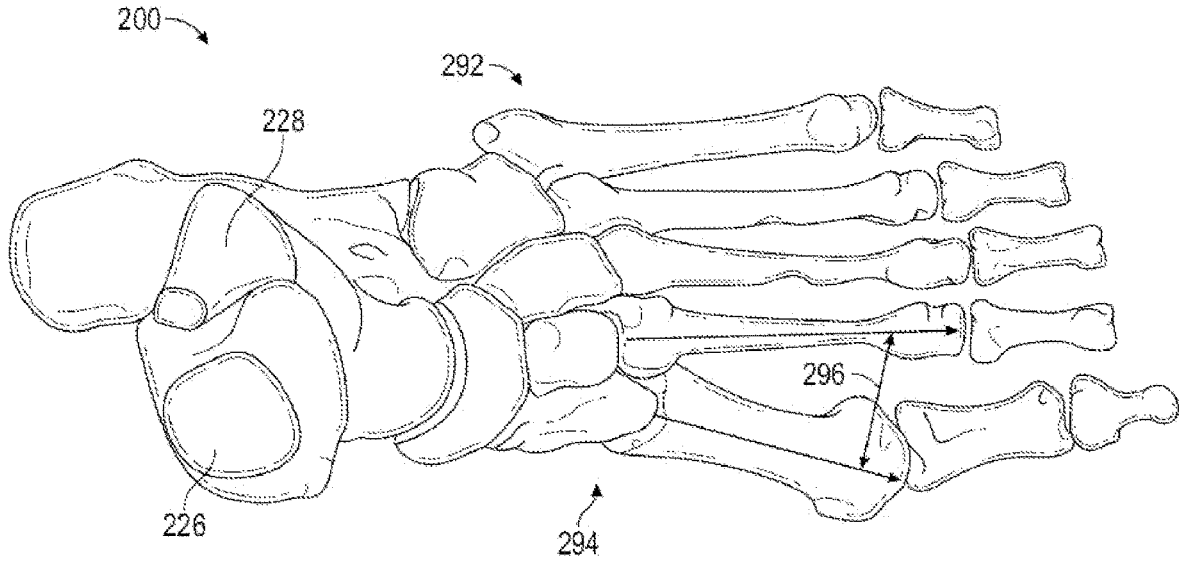
FIG. 2D is a dorsal perspective view of bones of a foot.

FIG. 2C is a perspective medial view of a foot illustrating a dorsal side 280 and a plantar side 282. The foot 200, as illustrated, may have a tibia 226 and a fibula 228, among others. Dorsal refers to the top of the foot. Plantar refers to the bottom of the foot. Proximal 284 is defined as "closer to the primary attachment point". Distal 286 is defined as "further away from the attachment point". Plantarflex or plantarflexion 288 means movement toward the plantar side 282 of a foot or hand, toward the sole or palm. Dorsiflex or dorsiflexion 290 means movement toward the dorsal side 280 of a foot or hand, toward the top. FIG. 2D is a perspective dorsal view of the foot 200. A transverse plane is the plane that shows the top of the foot. A lateral side 292 means a side furthest away from the midline of a body, or away from a plane of bilateral symmetry of the body. A medial side 294 means a side closest to the midline of a body, or toward a plane of bilateral symmetry of the body. For a Lapidus procedure, the intermetatarsal (IM) angle 296 is the angle to be corrected to remove the hallux valgus (bunion) deformity.

Figure 2E:
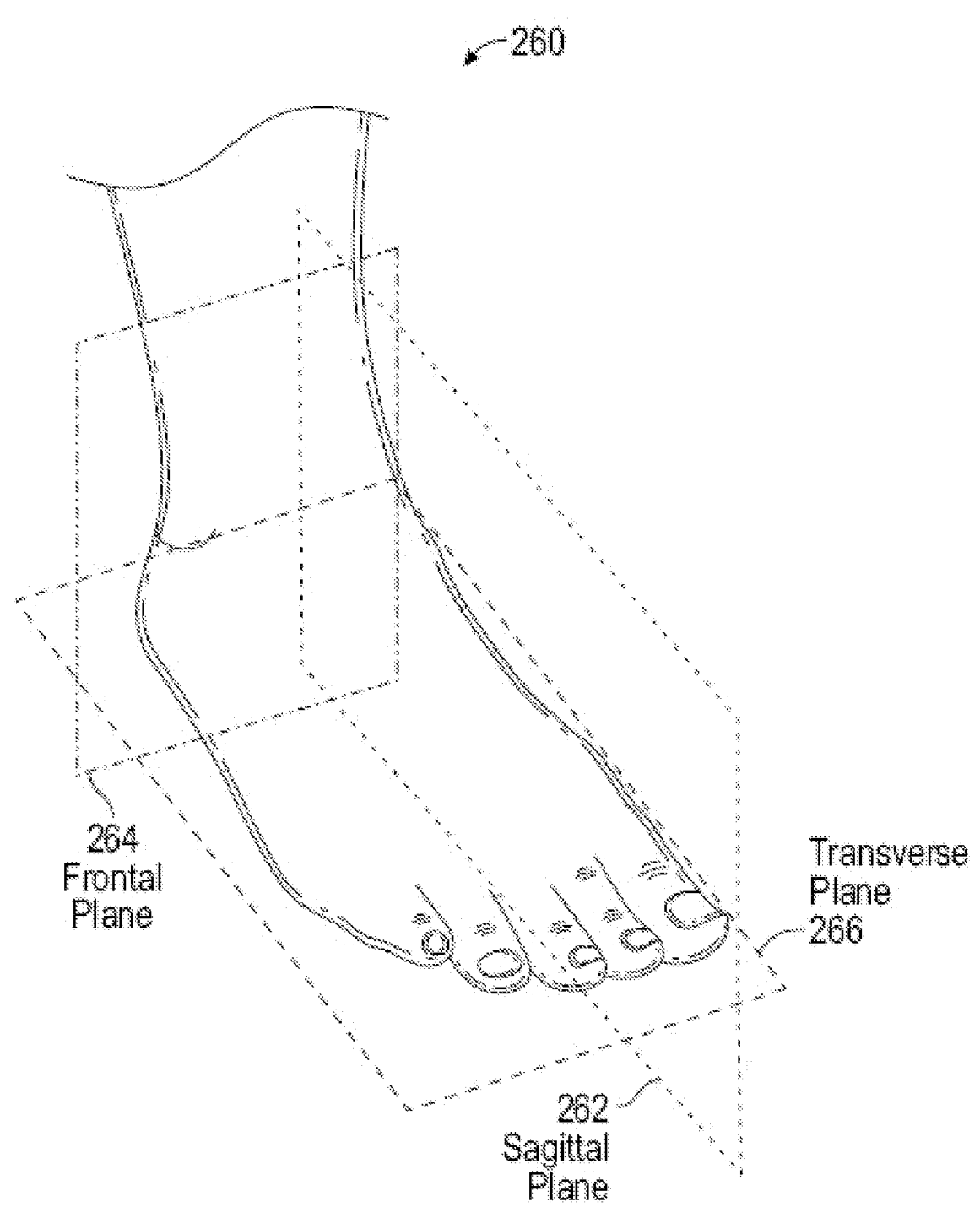
FIG. 2E is a view of a foot illustrating common planes of reference for a human foot.

FIG. 2E is a view of a foot illustrating common planes 260 of reference for a human foot. FIG. 2E illustrates a sagittal plane 262 that divides the foot into a right section and a left section half. The sagittal plane 262 is perpendicular to frontal or coronal plane 264 and the transverse plane 266. In the foot, the frontal plane 264 generally runs vertically through the ankle and the transverse plane 266 generally runs horizontally through the midfoot and toes of the foot.

Every patient and/or condition is different; accordingly, the degree of angular adjustment needed in each direction may be different for every patient. Use of a patient-specific instrument may help the surgeon obtain an optimal realignment, target, or position a bone tunnel, position one or more resections and/or fasteners and the like. Thus, providing patient-specific instruments, jigs, and/or instrumentation may provide unique benefits.

The present patient-specific instrumentation may be used to correct a wide variety of conditions. Such conditions include, but are not limited to, angular deformities of one bone in either the lower or upper extremities (for example, tibial deformities, calcaneal deformities, femoral deformities, and radial deformities). The present disclosure may also be used to treat an interface between two bones (for example, the ankle joint, metatarsal cuneiform joint, lisfranc's joint, complex Charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cuboid or subtalar joint or at the ankle between the tibia and talar junction. Additionally, patient-specific instruments could be used in the proximal leg between two bone segments or in the upper extremity such as found at the wrist or metacarpal levels.

Figure 3:
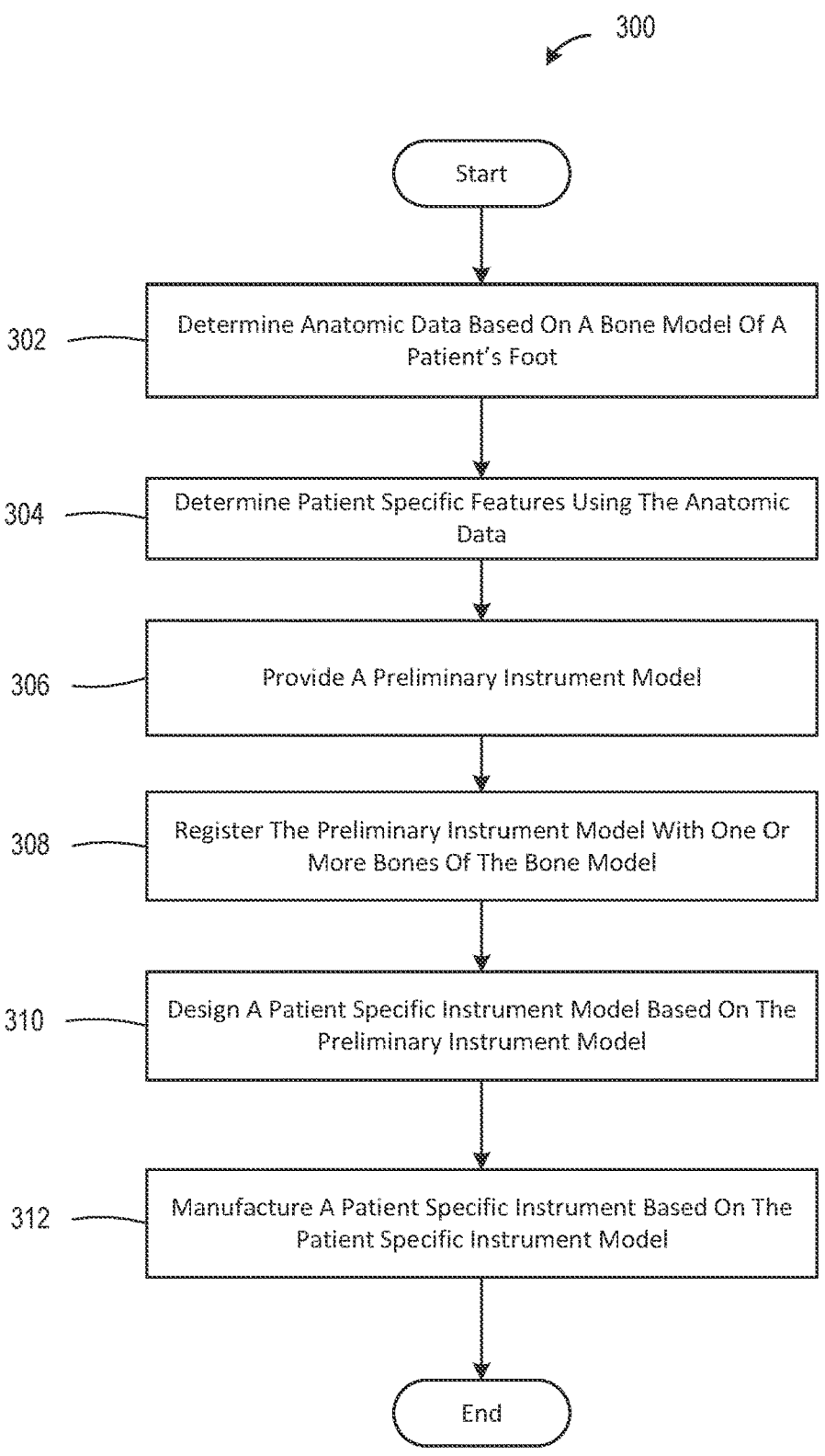
FIG. 3 is a flowchart diagram depicting a method for generating one or more patient-specific instruments, according to one embodiment.

FIG. 3 illustrates a flowchart diagram depicting a method 300 for generating one or more instruments (which may or may not be patient-specific) configured to correct or address a bone or foot condition, according to one embodiment. Prior to steps of the method 300, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve, or be a part of, anatomic data for a patient.

In one embodiment, the method 300 begins after a bone model of a patient's body or body part(s) is generated. In a first step 302, the method 300 may review the bone model and data associated with the bone model to determine anatomic data of a patient's foot.

After step 302, the method 300 may determine 304 one or more angles (e.g., trajectory angle) and/or patient-specific features for a procedure using the anatomic data. "Trajectory angle" refers to a recommended angle for deployment of an instrument, graft, body part, or resection feature angle relative to a bone of a patient for a procedure. In certain embodiments, determining steps, instruments, and/or implants for a corrective procedure may employ advanced computer analysis system, expert systems, machine learning, and/or automated/artificial intelligence.

Next, the method 300 may proceed and a preliminary instrument model is provided 306 from a repository of template models. A preliminary instrument model is a model of a preliminary instrument.

As used herein, "preliminary instrument" refers to a instrument configured, designed, and/or engineered to serve as a template, prototype, archetype, or starting point for creating, generating, or fabricating a patient-specific instrument. In one aspect, the preliminary instrument may be used, as-is, without any further changes, modifications, or adjustments and thus become a patient-specific instrument. In another aspect, the preliminary instrument may be modified, adjusted, or configured to more specifically address the goals, objectives, or needs of a patient or a surgeon and by way of the modifications become a patient-specific instrument. The patient-specific instrument can be used by a user, such as a surgeon, to guide steps in a surgical procedure, such as an osteotomy, graft harvest (e.g., autograft, allograft, or xenograft), minimally invasive surgical (MIS) procedure, and/or a tendon transfer procedure. Accordingly, a preliminary instrument model can be used to generate a patient-specific instrument. The patient-specific instrument model may be used in a surgical procedure to facilitate one or more steps of the procedure, and may be used to generate a patient-specific instrument that can be used in a surgical procedure for the patient.

In certain embodiments, the preliminary instrument model may be generated based on anatomic data and/or a bone model or a combination of these, and no model or predesigned structure, template, or prototype. Alternatively, or in addition, the preliminary instrument model may be, or may originate from, a template instrument model selected from a set of template instrument models. Each model in the set of template instrument models may be configured to fit for an average patient's foot. The template instrument model may subsequently be modified or revised by an automated process or manual process to generate the preliminary instrument model used in this disclosure.

As used herein, "template instrument" refers to an instrument configured, designed, and/or engineered to serve as a template for creating, generating, or fabricating a patient-specific instrument. In one aspect, the template instrument may be used, as-is, without any further changes, modifications, or adjustments and thus become a patient-specific instrument. In another aspect, the template instrument may be modified, adjusted, or configured to more specifically address the goals, objectives, or needs of a patient or a surgeon and by way of the modifications become a patient-specific instrument. The patient-specific instrument can be used by a user, such as a surgeon, to guide making one or more resections of a structure, such as a bone for a procedure. Accordingly, a template instrument model can be used to generate a patient-specific instrument model. The patient-specific instrument model may be used in a surgical procedure to address, correct, or mitigate effects of the identified deformity and may be used to generate a patient-specific instrument that can be used in a surgical procedure for the patient.

Next, the method 300 may register 308 the preliminary instrument model with one or more bones of the bone model. This step 308 facilitates customization and modification of the preliminary instrument model to generate a patient-specific instrument model from which a patient-specific instrument can be generated. The registration step 308 may combine two models and/or patient imaging data and positions both models for use in one system and/or in one model.

Next, the method 300 may design 310 a patient-specific instrument and/or procedure model based on the preliminary instrument model. The design step 310 may be completely automated or may optionally permit a user to make changes to a preliminary instrument model or partially completed patient-specific instrument model before the patient-specific instrument model is complete. A preliminary instrument model and patient-specific instrument model are two examples of an instrument model. As used herein, "instrument model" refers to a model, either physical or digital, that represents an instrument, tool, apparatus, or device. Examples, of an instrument model can include a cutting instrument model, a resection instrument model, an alignment instrument model, a reduction instrument model, a patient-specific tendon trajectory instrument model, graft harvesting instrument model, minimally invasive surgical (MIS) positioner model, or the like. In one embodiment, a patient-specific instrument and a patient-specific instrument model may be unique to a particular patient and that patient's anatomy and/or condition.

The method 300 may conclude by a step 312 in which patient-specific instrument may be manufactured based on the patient-specific instrument model. Various manufacturing tools, devices, systems, and/or techniques can be used to manufacture the patient-specific instrument.

FIG. 4 illustrates an exemplary system 400 configured to generate one or more patient-specific instruments configured to facilitate surgical procedures, according to one embodiment. The system 400 may include an apparatus 402 configured to accept, review, receive or reference a bone model 404 and provide a patient-specific instrument 406. In one embodiment, the apparatus 402 is a computing device. In another embodiment, the apparatus 402 may be a combination of computing devices and/or software components or a single software component such as a software application.

The apparatus 402 may include a determination module 410, a location module 420, a provision module 430, a registration module 440, a design module 450, and a manufacturing module 460. Each of which may be implemented in one or more of software, hardware, or a combination of hardware and software.

The determination module 410 determines anatomic data 412 from a bone model 404. In certain embodiments, the system 400 may not include a determination module 410 if the anatomic data is available directly from the bone model 404. In certain embodiments, the anatomic data for a bone model 404 may include data that identifies each anatomic structure within the bone model 404 and attributes about the anatomic structure. For example, the anatomic data may include measurements of the length, width, height, and density of each bone in the bone model. Furthermore, the anatomic data may include position information that identifies where each structure, such as a bone is in the bone model 404 relative to other structures, including bones. The anatomic data may be in any suitable format and may be stored separately or together with data that defines the bone model 404.

In one embodiment, the determination module 410 may use advanced computer analysis system such as image segmentation to determine the anatomic data. The determination module 410 may determine anatomic data from one more sources of medical imaging data, images, files, or the like. Alternatively, or in addition the determination module 410 may use software and/or systems that implement one or more artificial intelligence methods (e.g., machine learning and/or neural networks) for deriving, determining, or extrapolating, anatomic data from medical imaging or the bone model. In one embodiment, the determination module 410 may perform an anatomic mapping of the bone model 404 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

In one embodiment, the determination module 410 may use advanced computer analysis system such as image segmentation to determine the anatomic data. The determination module 410 may determine anatomic data from one more sources of medical imaging data, images, files, or the like. The determination module 410 may perform the image segmentation using 3D modeling systems and/or artificial intelligence (AI) segmentation tools. In certain embodiments, the determination module 410 is configured to identify and classify portions of bone based on a condition of the bone, based on the bone condition. Such classifications may include identifying bone stability, bone density, bone structure, bone deformity, bone structure, bone structure integrity, and the like. Accordingly, the determination module 410 may identify portions or sections or one or more bones based on a quality metric for the bone. Advantageously, that determination module 410 can identify high quality bone having a viable structure, integrity, and/or density versus lower quality bone having a nonviable structure, integrity, and/or density and a plurality of bone quality levels in between.

Accordingly, the determination module 410 can guide a surgeon to determine which areas of one or more bones of a patient are within a "soft tissue envelope" (bone of undesirable quality) as that bone relates to a particular deformity or pathology. Identifying the quality of one or more bones of the patient can aid a surgeon in determining what type of correction or adjustment is needed. For example, an ulceration that occurs due to a boney deformity can be mapped using the determination module 410 in a way that a correction can be performed to correct the deformity and reduce pressure to an area and address the structures that were causing the pressure ulceration/skin breakdown.

In addition, the determination module 410 and/or another component of the apparatus 402 can be used to perform anatomic mapping which may include advanced medical imaging, such as the use of CT scan, ultrasound, MRI, X-ray, and bone density scans can be combined to effectively create an anatomic map that determines the structural integrity of the underlying bone.

Identifying the structural integrity of the underlying bone can help in determining where bone resections (e.g., osteotomies) can be performed to preserve the densest bone in relation to conditions such as Charcot neuropathic, arthropathy where lesser dense bone can fail and collapse. It is well documented in the literature that failure to address and remove such lesser dense bone can ultimately lead to failure of a reconstruction and associated hardware.

The present disclosure provides, by way of at least the exemplary system 400, an anatomic map that can be part of anatomic data. The anatomic map can combine structural, deformity, and bone density information and can be utilized to determine the effective density of bone and help to determine where bone should be resected in order to remove the lesser dense bone while maintaining more viable bone to aid in the planning of the osteotomy/bone resection placement.

The location module 420 determines or identifies one or more recommended locations and/or trajectory angles for deployment of an instrument and/or soft tissue based on the anatomic data 412 and/or the bone model 404. In one embodiment, the location module 420 may compare the anatomic data 412 to a general model that is representative of most patient's anatomies and may be free from deformities or anomalies. The location module 420 can operate autonomously and/or may facilitate input and/or revisions from a user. The location module 420 may be completely automated, partially automated, or completely manual. A user may control how automated or manual the determining of the location and/or trajectory angles is.

The provision module 430 is configured to provide a preliminary instrument model 438. The provision module 430 may use a variety of methods to provide the preliminary instrument model. In one embodiment, the provision module 430 may generate a preliminary instrument model. In the same, or an alternative embodiment, the provision module 430 may select a template instrument model for a tendon (or tendon substitute) deployment procedure configured to enable locating the position and/or providing the trajectory provided by the location module 420. In one embodiment, the provision module 430 may select a template instrument model for a minimally invasive surgical (MIS) bunion correction procedure configured to enable locating the position and/or providing the trajectory for the fixation deployment. In one embodiment, the provision module 430 may select a template instrument model from a set of template instrument models (e.g., a library, set, or repository of template instrument models).

The registration module 440 registers the preliminary instrument model with one or more bones or other anatomical structures of the bone model 404. As explained above, registration is a process of combining medical imaging data, patient imaging data, and/or one or more models such that the preliminary instrument model can be used with the bone model 404.

The design module 450 designs a patient-specific instrument (or patient-specific instrument model) based on the preliminary instrument model. The design operation of the design module 450 may be completely automated, partially automated, or completely manual. A user may control how automated or manual the designing of the patient-specific instrument (or patient-specific instrument model) is.

The manufacturing module 460 may manufacture a patient-specific instrument 406 using the preliminary instrument model. The manufacturing module 460 may use a patient-specific instrument model generated from the preliminary instrument model. The manufacturing module 460 may provide the patient-specific instrument model to one or more manufacturing tools and/or fabrication tool (e.g., additive and/or subtractive). The patient-specific instrument model may be sent to the tools in any format such as an STL file or any other CAD modeling or CAM file or method for data exchange. In one embodiment, a user can adjust default parameters for the patient-specific instrument such as types and/or thicknesses of materials, dimensions, and the like before the manufacturing module 460 provides the patient-specific instrument model to a manufacturing tool.

Effective connection of the guide to one or more bones can ensure that surgical steps are performed in desired locations and/or with desired orientations and mitigate undesired surgical outcomes.

Figure 5:
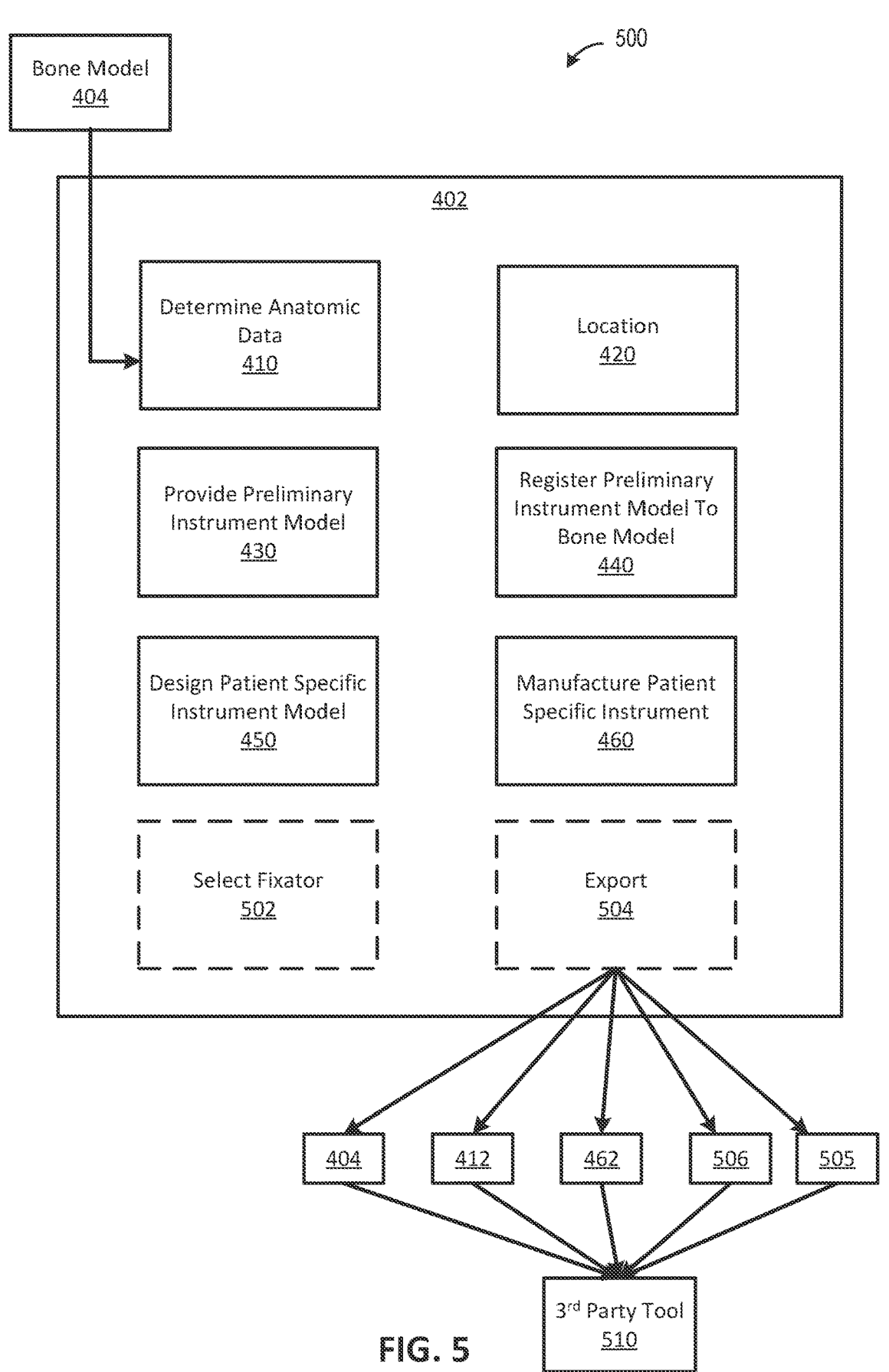
FIG. 5 illustrates an exemplary system configured to generate one or more patient-specific instruments, according to one embodiment.

FIG. 5 illustrates an exemplary system 500 configured to generate one or more patient-specific instruments configured to correct a bone condition, according to one embodiment. The system 500 may include similar components or modules to those described in relation to FIG. 4. In addition, the system 500 may include a fixator selector 502 and/or an export module 504.

The fixator selector 502 enables a user to determine which fixator(s) to use for a MIS bunion correction procedure planned for a patient. In one embodiment, the fixator selector 502 may recommend one or more fixators based on the bone model 404, the location, the trajectory, or input from a user or a history of prior MIS bunion correction procedures performed. The fixator selector 502 may select a fixator model from a set of predefined fixator models or select a physical fixator from a set of fixators. The fixators may include a plate and associated accessories such as screws, anchors, and the like.

In one embodiment, the fixator selector 502 includes an artificial intelligence or machine learning module. The artificial intelligence or machine learning module is configured to implement one or more of a variety of artificial intelligence modules that may be trained for selecting fixator(s) based on anatomic data 412 and/or other input parameters. In one embodiment, the artificial intelligence or machine learning module may be trained using a large data set of anatomic data 412 for suitable fixator(s) identified and labeled in the dataset by professionals for use to treat a particular condition. The artificial intelligence or machine learning module may implement, or use, a neural network configured according to the training such that as the artificial intelligence or machine learning module is able to select or recommend suitable fixator(s).

The export module 504 is configured to enable exporting of a patient-specific instrument model 462 for a variety of purposes including, but not limited to, fabrication/manufacture of a patient-specific instrument 406 and/or fixator(s), generation of a preoperative plan, generation of a physical bone model matching the bone model 404, and the like. In one embodiment, the export module 504 is configured to export the bone model 404, anatomic data 412, a patient-specific instrument model 462, a preoperative plan 506, a fixator model 508, or the like. In this manner the custom instrumentation and/or procedural steps for a procedure (e.g., a graft harvesting procedure, minimally invasive surgical (MIS) procedure, or the like) can be used in other tools. The preoperative plan 506 may include a set of step by step instructions or recommendation for a surgeon or other staff in performing a procedure (e.g., a graft harvesting procedure, minimally invasive surgical (MIS) procedure, or the like). The preoperative plan 506 may include images and text instructions and may include identification of instrumentation to be used for different steps of the procedure (e.g., a graft harvesting procedure, minimally invasive surgical (MIS) procedure, or the like). The instrumentation may include the patient-specific instrument 406 and/or one or more fixators/fasteners. In one embodiment, the export module 504 may provide a fixator model which can be used to fabricate a fixator for the procedure.

The exports (404, 412, 462, 506, and 508) may be inputs for a variety of 3rd party tools 510 including a manufacturing tool, a simulation tool, a virtual reality tool, an augmented reality tool, an operative procedure simulation tool, a robotic assistance tool, and the like. A surgeon can then use these tools when performing a procedure or for rehearsals and preparation for the procedure. For example, a physical model of the bones, patient-specific instrument 406, and/or fixators can be fabricated, and these can be used for a rehearsal operative procedure. Alternatively, a surgeon can use the bone model 404, preliminary instrument model 438, and/or a fixator model to perform a simulated procedure using an operative procedure simulation tool.

Figure 6:
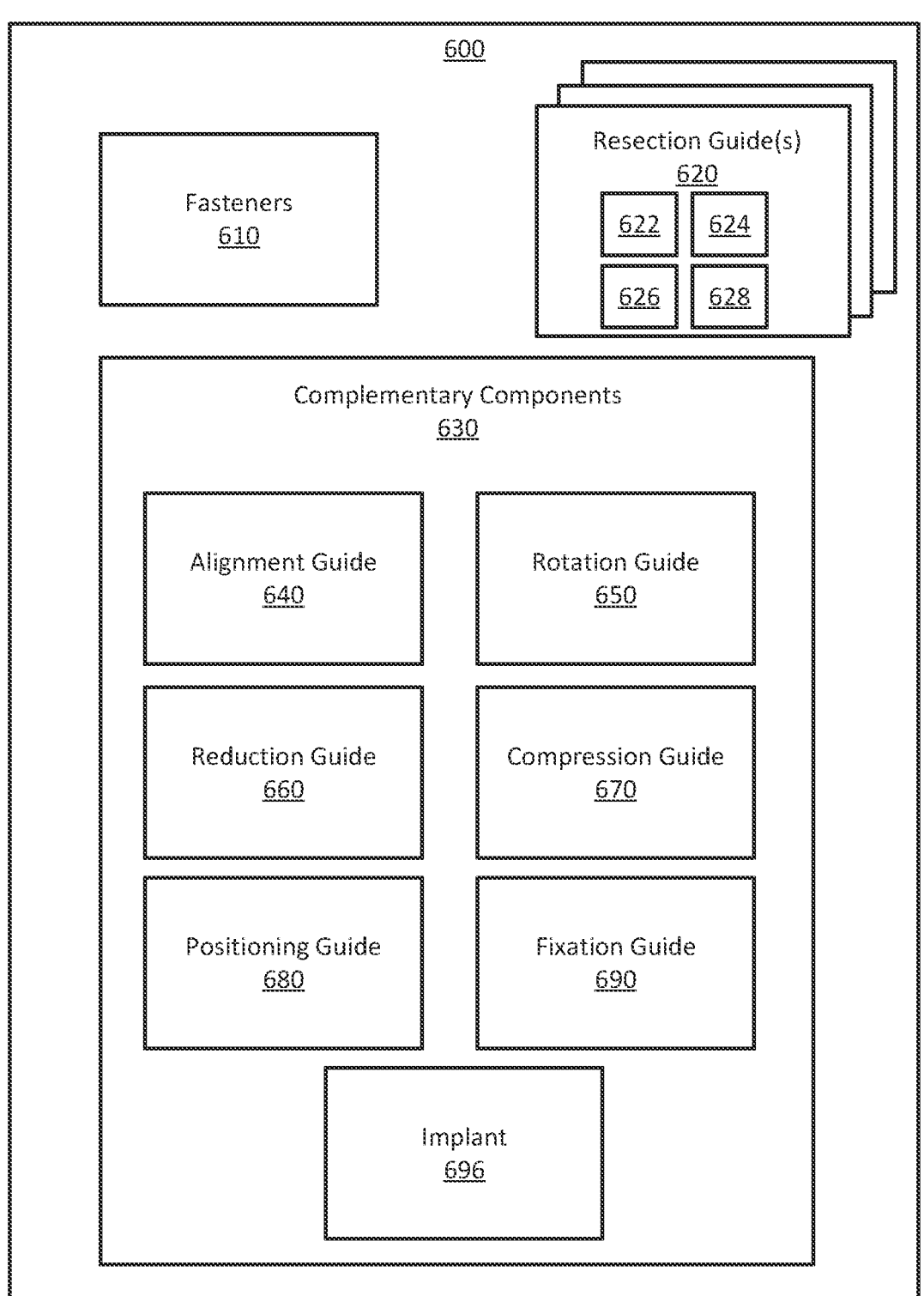
FIG. 6 illustrates an exemplary system for remediating a condition present in a patient's foot, according to one embodiment.

FIG. 6 illustrates an exemplary system 600, according to one embodiment. The system 600 can include one or more fasteners 610, one or more resection guides 620, and one or more complementary components 630. While a system 600 can be used for a variety of procedures, one or more features, components, and/or aspects of the system 600 may be particularly suited for one or more osteotomies on one or more bones of a structure such as a patient's foot, ankle, wrist, hand, shoulder, or the like.

In certain embodiments, the one or more fasteners 610 can include one or more permanent fasteners and/or one or more temporary fasteners. Typically, the fasteners 610 may be used during a variety of different steps of a procedure. Temporary fasteners are often used because they can securely hold bone or parts/fragments of bones while steps of the procedure are conducted. A common temporary fastener that can be used with system 600 is a K-wire, also referred to as a pin, guide pin, and/or anchor pin. Permanent fasteners 610 such as bone screws, bone staples, sutures, tethers or the like may also be used in a surgical procedure.

The one or more resection guides 620 assist a surgeon in performing different resection or dissection steps for an osteotomy or other procedure. In certain embodiments, a resection guide 620 includes one or more resection features 622 and one or more bone attachment features 624. The resection features 622 can take a variety of forms and/or embodiments. In one embodiment, the resection features 622 take the form of a cut channel or slot or other opening.

The resection features 622 provide a guide for a surgeon using a cutting tool to resect a bone, one or more bones, or other tissues of a patient. In certain embodiments, the resection features 622 may guide a surgeon in performing a resection, and osteotomy, and/or a dissection.

Similarly, the bone attachment features 624 can take a variety of forms and/or embodiments. The bone attachment features 624 may serve to secure the resection guide 620 and/or other instrumentation to one or more bones and/or one or more other structures. Often, a bone attachment feature 624 can take the form of a hole in and/or through the resection guide 620 together with a temporary fastener such as a K-wire, pin, or guide pin.

The bone attachment features 624 facilitate attachment (at least temporarily) of a resection guide 620 to one or more bones, or bone fragments, of a patient. The bone attachment features 624 may include any of a wide variety of fasteners or structures including, but not limited to, holes, spikes, prongs, screws, fastening devices, and/or the like. Effective connection of the resection guide 620 to one or more bones across a joint and/or to one or more bones can ensure that cut surfaces are formed in desired locations and orientations and mitigate removal of hard tissue and/or soft tissue in undesired locations and/or orientations.

In certain embodiments, a resection guide 620 may include one or more bone engagement surfaces 626 and/or one or more landmark registration features 628. In certain embodiments, a landmark registration feature 628 may extend from one or more sides or ends of a resection guide 620 and engage with one or more landmarks of a bone or joint or anatomical structure of a patient. Registration of the landmark registration feature 628 to a landmark of a bone or joint can serve to confirm and/or ensure that a surgeon has located a desired placement and/or orientation for a resection guide 620.

In certain embodiments, the bone engagement surfaces 626 are patient-specific: contoured to match a surface of: one or more bones and/or bone surfaces the resection guide 620 contacts during the procedure or one or more joints proximal to the resection guide 620 during the procedure. Alternatively, or in addition, the bone engagement surface 626 may not be patient-specific, and may, or may not, contact a bone surface during use of the resection guide 620. In one embodiment, a skin contact surface may be used in addition to, or in place of, a bone engagement surface. Those of skill in the art appreciate that one or more sides of any of the members of the system 600 may include one or more bone engagement surfaces 626. Consequently, one or more sides of the fasteners 610, the resection guide(s) 620, the complementary components 630, and/or the implants 696 may include one or more bone engagement surfaces 626.

In certain embodiments, the resection guide s 620 and/or aspects of the resection guide s 620 may be integrated into other components and/or instruments, such as a pin guide, a trajectory guide, an alignment guide, or the like.

The complementary components 630 serve to assist a surgeon during one or more steps of a procedure. Those of skill in the art appreciate that a number of components can serve as complementary components 630. One or more of the features, functions, or aspects of the complementary components 630 can include patient-specific features.

Examples of complementary components 630 include, but are not limited to, an alignment guide 640, a rotation guide 650, a reduction guide 660, a compression guide 670, a positioning guide 680, a fixation guide 690, and/or one or more implants 696. In general, the complementary components 630 serve to assist a surgeon in performing the function included in the name of the complementary component 630. Thus, an alignment guide 640 can help a surgeon align bones, parts of bones, or other parts of a patient as part of a procedure. A rotation guide 650 can help a surgeon rotate one or more bones, parts of bones, or other parts of a patient as part of a procedure. In one embodiment, a rotation guide 650 may hold one bone fragment stable while another bone fragment is rotated into a desired position.

A reduction guide 660 can help a surgeon position and/or orient one or more bones, parts of bones, or other parts of a patient as part of a procedure in order to reduce the bone, bones, bone parts, or other parts and/or in order to position and/or orient the bone, bones, bone parts, or other parts to a desired position and/or orientation. In certain embodiments, aspects and/or features of a reduction guide 660 can be integrated into one or more other components of an osteotomy system 600, such as components of the complementary components 630. A compression guide 670 can help a surgeon compress one or more bones, parts of bones, or other parts of a patient together or against an implant as part of a procedure. In certain embodiments, compression guide 670 can be a separate instrument such as a compressor and/or a combined compressor/distractor. The compressor/distractor can be used to compress two or more cut faces formed by an osteotomy until fixation is deployed or distract bones or parts of bones involved in a procedure. In certain embodiments, a compression guide 670 may serve a dual purpose as both a compression guide 670 and as a positioning guide 680. The same instrument may be used to both translate and/or rotate bones or bone fragments and compress two or more cut faces formed by an osteotomy until fixation can be deployed.

A positioning guide 680 (also referred to as a positioner) can help a surgeon position one or more bones, parts of bones, or other parts of a patient as part of a procedure. For example, a positioning guide 680 may hold one bone or bone fragment stable and hold one or more other bone fragments in a desired position while permanent or temporary fixation is deployed. In certain embodiments, the positioning guide 680 may hold bone fragments in a reduced position, and thus may function as both a positioning guide 680 and/or a reduction guide 660.

In certain embodiments, the positioning guide 680 may be designed and fabricated to be patient-specific. The patient-specific aspects can include a patient-specific bone engagement surface, a predefined angle for reorienting one or more bone or bone parts within one or more planes, a predefined position for bone attachment features 624 or fasteners 610, a predefined or patient-specific offset or amount of translation that is provided, or the like. Alternatively, or in addition, the positioning guide 680 may be selected from a kit, collection, or repository of a number of positioning guides 680: each having a different configuration for one or more aspects/attributes of the positioning guide 680. For example, each member of the repository/kit may include a different positioning angle (repositioning or correction angle), the angles may differ by 2 degrees for example. In such an embodiment, each positioning guide 680 may not be patient-specific to a particular patient but may provide the desired amount of positioning to meet the goals of the surgeon. In certain embodiments, a preoperative plan generated based on the present disclosure may include a recommendation for the positioning guide 680 to be used, even if the recommended positioning guide 680 is not patient-specific to the particular patient.

A fixation guide 690 can help a surgeon in completing one or more temporary or permanent fixation steps for one or more bones, parts of bones, or other parts of a patient as part of a procedure. The fixation guide 690 may include and/or may use one or more components of a fastener or fixation system including implant hardware of the fastener or fixation system.

Those of skill in the art will appreciate that the other complementary components 630 may each have functions, purposes, and/or advantages with respect to one or more anatomical parts of the patient. Alternatively, or in addition, the other complementary components 630 may each have functions, purposes, and/or advantages with respect to one or more instruments and/or one or more anatomical parts of the patient. For example, a trajectory guide may be a type of alignment guide 640 in that the trajectory guide facilitates alignment of fixation with the desired location and/or trajectory/orientation with respect to one or more anatomical parts of the patient. Alternatively, or in addition, a trajectory guide may also be considered a type of fixation guide 690 because the trajectory guide facilitates deployment of one or more fasteners 610.

Advantageously, the system 600 can help a surgeon overcome one or more of the challenges in performing an osteotomy procedure, particularly on bones of a hand or of a foot of a patient, such as on the forefoot, midfoot, or hindfoot. One challenge during an osteotomy procedure can be maintaining control of, and/or position, and/or orientation of a bone, one or more bones, and/or bone pieces/fragments, particularly once a resection or dissection is performed. Advantageously, the fasteners 610, resection guide(s) 620, and/or complementary components 630 can be configured to assist in overcoming this challenge.

Advantageously, system 600 can help a surgeon in positioning, placing, and/or orienting a resection guide accurately. Modern techniques may include preoperative planning, simulation, or even practice using computer models, 3D printed models, virtual reality systems, augmented reality systems or the like. However, simulations and models are still different from actually positioning a resection guide on a patient's bone, joint, or body part during the procedure. System 600 can include a number of features, including patient-specific features, to assist the surgeon with the positioning. In one embodiment, the resection guide 620 can include one or more landmark registration features 628.

Advantageously, the system 600 can help a surgeon in securing guides of the osteotomy system 600, such as a resection guide, as well as how to readily remove the guide (e.g., resection guide) without disturbing a reduction, shifting, reorienting, or repositioning one or more bones or parts of bones while removing the guide. In certain embodiments, the system 600 is configured to permit removal of a guide while keeping temporary fasteners in place for use in subsequent steps of an osteotomy procedure. Alternatively, or in addition, system 600 may facilitate positioning of temporary fasteners during one step of a wedge osteotomy procedure for use in a subsequent step of the wedge osteotomy procedure. Removal of a guide during an osteotomy procedure can be particularly challenging where translation and/or rotation of the bones involved in the osteotomy procedure is required for the success of the osteotomy procedure. Advantageously, system 600 accommodates translation and/or rotation of the bones during the osteotomy procedure while facilitating a successful outcome for the osteotomy procedure.

Advantageously, the components of the system 600 can be specifically designed for a particular patient. Alternatively, or in addition, the components of the system 600 can be specifically designed for a class of patients. Each of the components of system 600 can be designed, adapted, engineered and/or manufactured such that each feature, attribute, or aspect of the component is specifically designed to address one or more specific indications present in a patient. Advantageously, the cuts made for the osteotomy procedure can be of a size, position, orientation, and/or angle that provides for an optimal osteotomy with minimal risk of undesirable resection. In one embodiment, the components of system 600 can be configured such that an osteotomy is performed that enables a correction in more than one plane in relation to the parts of the body of the patient. For example, cut channels or resection features 622 in a resection guide 620 can be oriented and configured such that when the bones are fused/fixated the correction results from translation, rotation, and/or movement of bones or bone parts in two or more planes (e.g., sagittal and transverse) once the fragments or bones are reduced.

In certain embodiments, the exemplary system 600 may include a plurality of fasteners 610, resection guides 620, and/or complementary components 630. For example, a surgeon may plan to resect a plurality of osteotomies from the bone(s) in order to accomplish a desired correction. In one example, one or more wedge segments may be resected from a medial side of a patient's foot and another one or more wedge segments may be resected from a lateral side of the patient's foot. These wedge segments may extend part way into the foot, or through from one side of the foot to the other. Of course, multiple wedge segments may be formed on one side of the foot as well.

Additionally, a surgeon may use one or more components in an exemplary system 600 to make multiple cuts in the bone(s). The multiple cuts may be centered over or around an apex of a deformity or positioned at other locations within the foot such that when the multiple cuts are made, any resected segments removed, or added bone void fillers introduced, and/or bones and/or bone fragments translated and/or rotated the combined angles, surfaces, removed segments, and/or added portions cooperate to provide a desired correction. Each of the components of the exemplary system 600 can be identified, defined, and reviewed using the apparatuses, systems, and/or methods of the present disclosure.

In certain embodiments, the components of system 600 may be made as small as possible to minimize the amount of soft tissue that is opened in the patient for the osteotomy procedure. Alternatively, or in addition, walls and/or sides of the components may be beveled and/or angled to avoid contact with other hard tissue or soft tissues in the operating field for the osteotomy procedure.

Those of skill in the art will appreciate that for certain osteotomy procedures a complementary component 630 may not be needed or a given complementary component 630 may be optional for use in the osteotomy procedure. Similarly, those of skill in the art will appreciate that certain features of the fasteners 610, resection guides 620, and/or complementary components 630 can be combined into one or more of apparatus or devices or may be provided using a plurality of separate devices.

Figure 7:
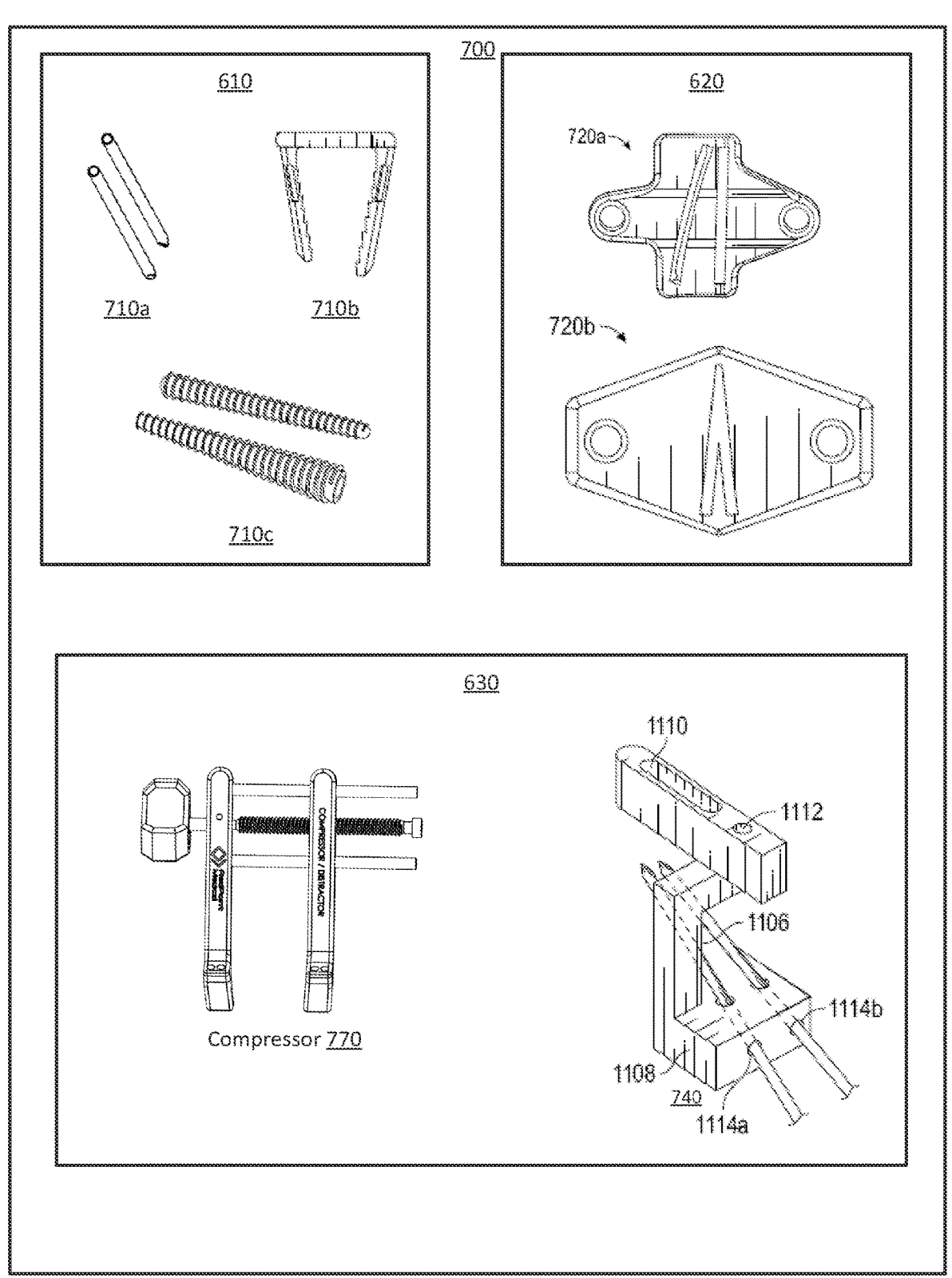
FIG. 7 illustrates an exemplary system for an osteotomy near a base of a metatarsal, according to one embodiment.

FIG. 7 is a side perspective view of a resection guide 700 (also referred to as a cutting guide 700 according to one embodiment) shown secured to a bone. In this example, the resection guide 700 is secured to a medial side of a first metatarsal 208. The first metatarsal 208 includes two sesamoids 258. Of course, the resection guide 700 can be secured to other bones of a patient to guide a surgeon in making cuts or performing one or more osteotomies in one or more bones. The resection guide 700 may also be referred to as an oscillating blade cut jig based on the type of cutting tool the resection guide 700 is designed to accept.

FIG. 7 illustrates an exemplary system 700 for an osteotomy at or near a base of a metatarsal, according to one embodiment. Those of skill in the art will appreciate that embodiments of the present disclosure may be used for a through cut osteotomy, a wedge osteotomy, or the like. An osteotomy at or near a base of a metatarsal can be an advantageous intervention for a patient because such an osteotomy can preserve the TMT joint proximal to the base. Preservation of the TMT joint can help a patient maintain increased mobility. In certain instances, a patient may have already received an arthrodesis of the TMT joint however the recovery may have resulted in healing of the bones of the TMT such that the metatarsal is dorsiflexed more than desired. An osteotomy using the exemplary system 700 can enable reorientation of the metatarsal to a more desired configuration, in some instances, without disturbing the prior arthrodesis.

The system 700 may include one or more fasteners 710, a resection guide (two embodiments shown resection guide 720a and resection guide 720b), and one or more other complementary components 630, such as a compressor 770 (a type of compression guide 670) and/or a trajectory guide 740 (a type of alignment guide 640). Advantageously, the apparatus, system, and/or methods of the present disclosure enable the surgeon and/or patient to preplan each aspect of the surgical procedure. For example, which fasteners 710, which style and configuration of metatarsal base resection guide 720, which compressor 770, and/or which trajectory guide 740 will be used can all be decided before the surgical procedure is scheduled.

In the illustrated embodiment, system 700 includes one or more guide pins, pins, or k-wires 710a, one or more staples 710b, and one or more bone screws 710c. Certain fasteners 710 may be used for temporary fixation while others may be used for permanent fixation. In one embodiment, the fasteners 710 are configured to single use. The compressor 770 and/or trajectory guide 740 may be provided in a surgical kit and may be reused with a number of patients for a number of surgical procedures.

In the illustrated embodiment, the resection guide 620 may be a custom patient-specific resection guide made for a particular patient and/or for a particular surgical procedure. In the illustrated embodiment, the resection guide 620 is for an osteotomy of a metatarsal at, or near (e.g. at a MDJ junction), a base of the metatarsal. Consequently, the resection guide 620 may be referred to as a metatarsal base resection guide 720. While a metatarsal base resection guide 720 is unique to a particular patient, the system 700 illustrates two alternative embodiments to show that each resection guide 620 can be custom designed based on the needs of the patient, the type of surgical procedure, and/or the preferences of the surgeon. Advantageously, in certain embodiments, practically every aspect of the features, aspects, and/or attributes of the resection guide 620 can be specified and/or ordered.

Different aspects and/or embodiments of the components of the system 700 are described in more detail herein. In one embodiment, the system 700 includes a metatarsal base resection guide 720 that may be made up of a body, a proximal slot and a distal slot as in resection guide 720a or a single resection feature as in resection guide 720b, a landmark registration feature including a probe bone engagement surface, a proximal hole and a distal hole that each accept a guide pin, and a bone engagement surface. The system 700 may also include a trajectory guide 740 having a body with a head connected to a base by a neck. The trajectory guide 740 may serve to guide temporary and/or permanent fixation using one or more fasteners such as guide pins 710a and/or bone screws 710c.

FIGS. 8A-8F are a top perspective, top or superior, bottom or inferior, left side or proximal, right side or distal, front or medial, back or lateral, views respectively of an example resection guide 800. In these figures, the metatarsal base resection guide 800 is similar in style and configuration to the resection guide 720a model.

The resection guide 800 provides an accurate and precise guide for performing one or more osteotomies on a bone of a patient. In particular, the resection guide 800 is specifically designed and engineered for one or more osteotomies at or near the base of a metatarsal bone of the patient. the resection guide 800 includes a proximal end 802, a distal end 804, and a body 806. The body 806 includes a superior side 808, an inferior side 810, a medial side 812, a lateral side 814, a proximal side 816, and a distal side 818. The body 806 can be made of a variety of materials including metal, ceramic, PEEK, Nylon-12, and the like. In one embodiment, the body 806 is pliable such that the medial side 812 and/or lateral side 814 can bend along a long axis 820 of the resection guide 800. The medial side 812, lateral side 814, proximal side 816, and distal side 818 of the body 806 are named to correspond to where the sides are when the resection guide 800 is deployed for use on a patient and correlate to such directions for anatomy of the patient.

FIGS. 8A, 8B, 8C, 8E, and 8F illustrate that the resection guide 800 includes a resection feature 822. Resection feature 822 provides a sure guide for a cutting tool used together with the resection feature 822. By placing and operating the cutting tool together with the resection feature 822 a surgeon can be assured that the cuts for an osteotomy will be made in the hard and/or soft tissue of a patient precisely where the resection was intended and/or planned. The stability and accuracy of the resection feature 822 enables a surgeon to perform their duties with less stress and anxiety once the resection guide 800 is positioned in the desired location.

A resection feature 822 can take a variety of forms. Often the resection feature 822 includes one or more openings that are sized to receive the cutting tool and provide clearance and/or allowance for the cutting tool to cut tissue of the patient. In the illustrated embodiment, the resection feature 822 is positioned between the proximal end 802 and the distal end 804 and may include proximal slot 824 and a distal slot 826. In one embodiment, the resection feature 822 guides resection of a metatarsal of a patient's foot. A user, such as a surgeon, can insert the cutting tool into one, or each, of the proximal slot 824 and the distal slot 826, through the slot and into the tissue of the patient. The slots may extend from the superior side 808 through the body 806 and out the inferior side 810. In one embodiment, the length of the slot though the body 806 may function as a stop to control a depth for a cutting tool into tissue near the inferior side 810.

The proximal slot 824 and/or distal slot 826 can be sized, angled, and/or oriented to ensure that movement of the cutting tool within the respective slot creates the desired osteotomy. Advantageously, each of the configuration aspects of resection feature 822 can be predetermined and/or defined by a surgeon in preparing for the surgical procedure and/or customized (e.g. patient-specific) for a particular patient.

The resection guide 800 also includes a bone attachment feature 830 that serves to securely connect the resection guide 800 to one or more bones of a patient. In particular, the bone attachment feature 830 couples the body 806 to a metatarsal of the patient. The bone attachment feature 830 can take many forms. In one embodiment, the bone attachment feature 830 includes at least one proximal hole 832 and at least one distal hole 834. Alternatively, the bone attachment feature 830 may include spikes or prongs that extend from inferior side 810 that are configured to engage with cortical bone of a patient.

The proximal hole 832 may extend from the superior side 808 through to the inferior side 810 of the body 806. The distal hole 834 may extend from the superior side 808 through to the inferior side 810 of the body 806. In certain embodiments, the proximal hole 832 may be configured to receive a proximal guide pin 836 and the distal hole 834 may be configured to receive a distal guide pin 838. In certain embodiments, the proximal guide pin 836 and/or distal guide pin 838 may be K-wires sized to fit through the proximal hole 832 and/or distal hole 834. The proximal hole 832 and proximal guide pin 836 and the distal hole 834 and distal guide pin 838 may be configured to cooperate with each other to secure the body 806 to the bone, to the metatarsal of a patient.

Figures 8A, 8B, 8C, 8D, 8E, 8F:
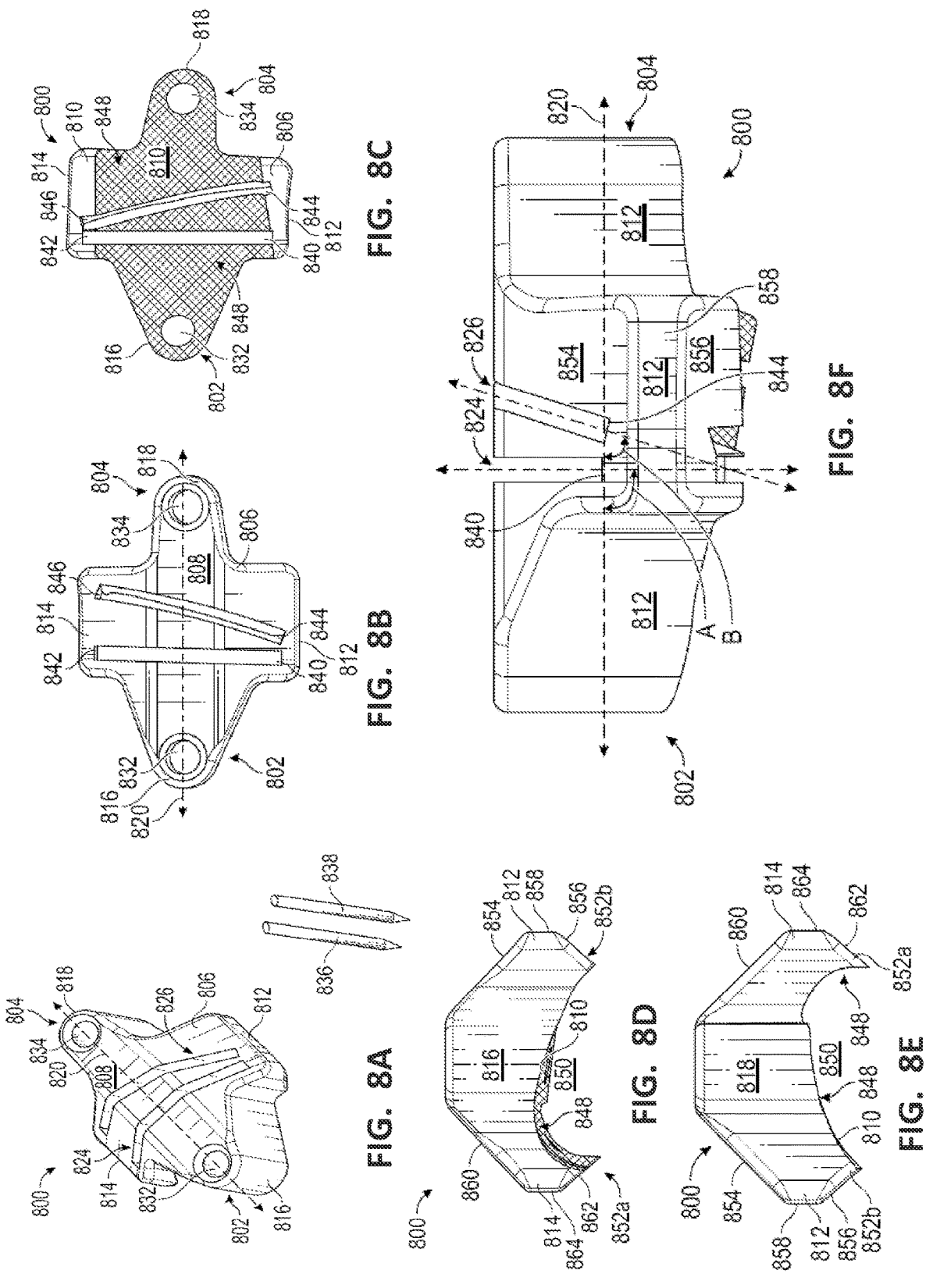
FIGS. 8A-8G are a top perspective, top or superior, bottom or inferior, left side or proximal, right side or distal, front or medial, back or lateral, views respectively of an example resection guide.

Referring now to FIG. 8B, the configuration and/or orientation of the proximal slot 824 and distal slot 826 are illustrated. In one embodiment, the proximal slot 824 includes a first medial end 840 and a first lateral end 842. The distal slot 826 includes a second medial end 844 and a second lateral end 846. In the illustrated embodiment, the first medial end 840, first lateral end 842, second medial end 844, and second lateral end 846 are closed meaning that the ends terminate within the body 806. those of skill in the art will appreciate that one or more of the first medial end 840, first lateral end 842, second medial end 844, and second lateral end 846 may be open meaning that the end extends beyond the body 806 and does not terminate within the body 806. Whether or not one or more ends terminates within the body 806 may depend on anatomy of a patient, the surgical procedure to be performed, and/or preferences of a surgeon. Advantageously, each of these aspects can be predetermined and defined before the resection guide 800 is fabricated.

FIG. 8C illustrates an inferior side 810 of the resection guide 800. In the illustrated embodiment, the resection guide 800 includes a bone engagement surface 848 configured to register to a metatarsal based on medical imaging taken of the patient's foot. In certain embodiments, the bone engagement surface 848 is configured to register to one or more surfaces of a metatarsal of a patient. Advantageously, the bone engagement surface 848 is formed with precision to closely and/or substantially match the contours of one or more surfaces of the bone, such as a metatarsal (and in certain embodiments surfaces of a metatarsal near a base of the metatarsal).

FIG. 8D illustrates a side view towards the proximal side 816 of the resection guide 800. The resection guide 800 includes a bone engagement opening 850 formed on the inferior side 810 of the body 806. The bone engagement opening 850 is an opening in a side of the body 806 configured to match a size, contour, and/or configuration of a bone. Advantageously, the length, width, and/or depth of the bone engagement opening 850 are configured to match the shape of the bone that fills the bone engagement opening 850 when the resection guide 800 is deployed and used. Consequently, a resection guide 800 can be slid or translated along a surface of a bone until the bone engagement opening 850 seats with, mates with, engages and/or fills the bone engagement opening 850. Once a contour and/or surface of a bone fills the bone engagement opening 850 a surgeon can be assured that the resection guide 800 is in a desired location relative to the bone.

The bone engagement opening 850 is the opening near the inferior side 810 and may be bordered by a part of the inferior side 810 opposite the superior side 808, part of the inferior side 810 opposite the lateral side 814, and/or part of the inferior side 810 opposite the medial side 812. In certain embodiments, the lateral side 814 and/or inferior side 810 may extend in an inferior direction as shown. In another embodiment, the lateral side 814 and/or inferior side 810 may extend in an inferior direction until the lateral side 814 is opposite the medial side 812 and the bone engagement opening 850, formed by the extension of the medial side 812 and lateral side 814, receives about half of a circumference of the bone, of a metatarsal.

In certain embodiments, the bone engagement opening 850 includes the bone engagement surface 848. Where the bone engagement opening 850 includes the bone engagement surface 848 the matching of the bone engagement surface 848 to one or more surface of the bone can provide a further assurance to a surgeon that the resection guide 800 is precisely positioned in a position desired. In another embodiment, the bone engagement opening 850 may not include a bone engagement surface 848 and instead the bone engagement opening 850 may include a recess, cavity, depression, or the like and a smooth surface on an inferior side 810 of the body 806.

FIG. 8E illustrates a side view towards the distal side 818 of the resection guide 800. FIG. 8E also illustrates the bone engagement opening 850. Those of skill in the art will appreciate that the length, width and/or height of the bone engagement opening 850 can changes as one measures from the proximal side 816 towards the distal side 818.

FIGS. 8D and 8E also illustrate that in certain embodiments, the resection guide 800 may include one or more landmark registration features 852. A landmark registration feature 852 is a structure that serves to engage with one or more landmarks on anatomy of a patient and can be used by a surgeon to ensure that the resection guide 800 is positioned in a desired position before beginning an osteotomy. In the illustrated embodiment, the resection guide 800 includes a lateral landmark registration features 852a and a medial landmark registration features 852b. In certain embodiments, the landmark registration features 852 may resemble and/or function as a hook or a probe. In the illustrated embodiment, the landmark registration features 852 extend from the inferior side of the medial side 812 and/or lateral side 814. Alternatively, or in addition, a resection guide 800 may include a landmark registration feature 852 that extends from one or more the proximal side 816 of the body 806 and/or the distal side 818 of the body 806. In certain embodiments, a landmark registration features 852 may include a bone engagement surface or a probe bone engagement surface.

FIGS. 8D and 8E also illustrate that in certain embodiments, the medial side 812 and/or lateral side 814 include features that facilitate use of the resection guide 800 while avoiding certain soft tissue in the vicinity of a bone and/or provide clearance for movement of a cutting tool within the resection feature 822. For example, the medial side 812 may include a medial superior surface 854 and a medial inferior surface 856 that meet at a medial edge 858. Advantageously, the medial inferior surface 856 may extend from inferior side 810 to the medial edge 858 at an angle such that the medial inferior surface 856 provides clearance for a cutting tool inserted into and moved within proximal slot 824 and/or distal slot 826 or another resection feature 822 and may mitigate impingement of soft tissue near the bone (e.g., near a medial side 812 of the bone). In certain embodiments, the angle may range between about 80 and about 170 degrees.

Of course, the medial superior surface 854 may extend from the superior side 808 to the medial edge 858 at an angle. The angle of the medial superior surface 854 may enable use of the cutting guide 800 in tighter openings and thus minimize the size of incisions used for a procedure.

In another example, the lateral side 814 may include a lateral superior surface 860 and a lateral inferior surface 862 that meet at a lateral edge 864. Advantageously, the lateral inferior surface 862 may extend from inferior side 810 to the lateral edge 864 at an angle such that the lateral inferior surface 862 provides clearance for a cutting tool inserted into and moved within proximal slot 824 and/or distal slot 826 or another resection feature 822 and may mitigate impingement of impinge soft tissue near the bone (e.g., near a lateral side 814 of the bone). In certain embodiments, the angle may range between about 80 and about 170 degrees. Of course, the lateral superior surface 860 may extend from the superior side 808 to the lateral edge 864 at an angle. The angle of the lateral superior surface 860 may enable use of the cutting guide 800 in tighter openings and thus minimize the size of incisions used for a procedure.

FIG. 8F illustrates a side view facing a medial side 812 of the resection guide 800. FIG. 8F illustrates that the proximal slot 824 and distal slot 826 can extend through the resection guide 800 at various angles with respect to a long axis 820 of the resection guide 800. In one embodiment, the proximal slot 824 may extend at a first angle relative to the long axis 820. In the illustrated embodiment, the proximal slot 824 extends at an angle A (e.g., first angle) of about a 90 degree angle relative to the long axis 820 and the distal slot 826 may extend at an angle B (e.g., second angle) of about a 71 degree angle measured from the long axis 820 in the plantar or inferior direction.

Figures 8G, 8H, 8I:
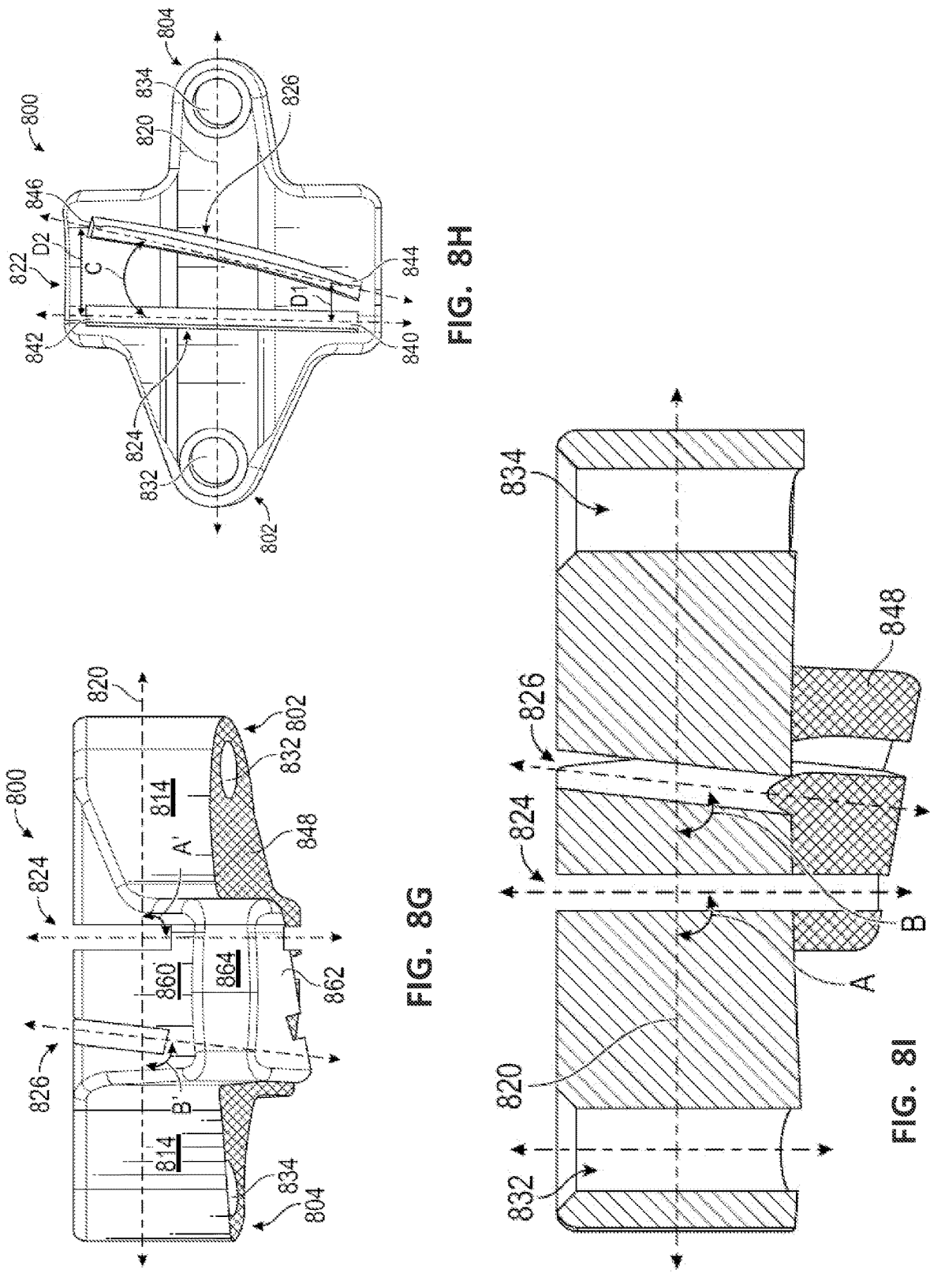
FIG. 8H is a top view of the example resection guide of FIGS. 8A-8G.
FIG. 8I is a cross-section view of the example resection guide of FIGS. 8A-8G.

FIG. 8G illustrates a side view facing a lateral side 814 of the resection guide 800. FIG. 8G illustrates that the proximal slot 824 and distal slot 826 can extend through the resection guide 800 at various angles with respect to a long axis 820 of the resection guide 800. In the illustrated embodiment, the proximal slot 824 extends at angle A' of about a 90 degree angle relative to the long axis 820 and the distal slot 826 may extend at angle B' of about an 83 degree angle measured from the long axis 820 in the plantar or inferior direction. In certain embodiments, one may desire that one of angle A and angle B be at about 90 degrees relative to the long axis 820 and remains the same angle from a medial end to a lateral end along one of the slots. This may be desirable because 90 degree angled osteotomies are often easier to perform and having one of the new cut faces perpendicular to the long axis 820 can serve as a favorable reference plane for subsequent steps in a surgical procedure.

FIG. 8H is a top view of the example resection guide of FIGS. 8A-8G. FIG. 8H illustrates that the resection feature 822 can be positioned at different locations between the proximal end 802 and the distal end 804. In addition, the first medial end 840 and second medial end 844 can be separated by a first distance D1 and the first lateral end 842 and second lateral end 846 can be separated by a second distance D2. Alternatively, or in addition, the distances D1 and D2 can impact an angle C that indicates a number of degrees that proximal slot 824 is offset from distal slot 826. In certain embodiments, angle C can range between about 0 degrees to about 55 degrees. Angle C may represent a third angle that can be used to describe and/or configure the proximal slot 824 and distal slot 826 and may be an angle measured within the transverse plane 266.

Those of skill in the art will appreciate that the lengths of D1 and D2 in relation to each other has a direct relationship to what size and shape of bone fragment an osteotomy using the resection feature 822 will resect from the bone or even if a wedge will be resected or if the osteotomy simply separates the bone. Those of skill in the art will appreciate that the position and orientation of the proximal slot 824 and distal slot 826 and the corresponding cut surface a surgeon can form using the resection feature 822 can vary depending on the anatomical structures of the patient, the osteotomy procedure being performed, preferences of the surgeon, the nature of the condition, and the like.

For example in the illustrated embodiment of FIG. 8H, the first medial end 840 of proximal slot 824 is closer to second medial end 844 of distal slot 826 (D1) than first lateral end 842 is in relation to second lateral end 846 (D2, D1 is shorter than D2). Such a configuration may be desirable to form a lateral closing wedge osteotomy, also referred to as a lateral base closing wedge osteotomy, when the resection guide 800 sits on the dorsal surface of the metatarsal.

In another embodiment, the first lateral end 842 may be closer to second lateral end 846 (D2) than the first medial end 840 is in relation to the second medial end 844 (D1, D2 is shorter than D1). Such a configuration may be desirable to form a medial closing wedge osteotomy, also referred to as a medial base closing wedge osteotomy, when the resection guide 800 sits on the dorsal surface of the metatarsal.

Of course in another embodiment, the proximal slot 824 and distal slot 826 may be configured such that D1 is substantially the same as D2. Such a configuration may be desirable to form a dorsal closing wedge osteotomy, also referred to as a dorsal base closing wedge osteotomy, when the resection guide 800 sits on the dorsal surface of the metatarsal. Such an osteotomy is one example of a uniplanar correction since reduction after the osteotomy will result in a dorsiflexion of the metatarsal.

In yet another embodiment, a first distance D1 may be substantially zero such that the proximal slot 824 and the distal slot 826 connect at the first medial end 840 and the second medial end 844. Such a configuration is similar to the embodiment illustrated in resection guide 720*b* introduced earlier. Such a configuration may be desirable to resect a lateral wedge from the metatarsal that reorients the metatarsal more laterally after reduction. In such a configuration the proximal slot 824 and distal slot 826 may be positioned such that an osteotomy using each slot resects a wedge while leaving the medial cortex adjacent to the osteotomy intact. The remaining medial cortex may serve to keep two parts of the metatarsal connect and may serve as a living hinge when the two bone fragments are reduced, and the two cut faces are joined.

Alternatively, or in addition, the first medial end 840 and second medial end 844 may come together in a way that extends beyond the medial cortex such that the osteotomy forms two bone segments that can be reduced. An osteotomy that extends through the medial cortex may be desirable where the correction is designed to cause translation and/or rotation of one bone fragment relative to the other bone fragment in two or more planes of the foot.

FIG. 8I is a cross-section view of the example resection guide of FIGS. 8A-8G. The cross-section in FIG. 8I is taken in a superior to inferior direction at the long axis 820. FIG. 8I illustrates that the angles (angle A, angle A', angle B, angle B') of the slots 824, 826 are the same when measured at the center of the body 806. However, since the slots 824, 826 can be offset from each other by the same, or different, distances (e.g., D1, D2) at the ends and/or at various angles such as angle C within a horizontal plane such as the transverse plane 266, angle A measured near the medial side

812 may be different from angle A' measured near the lateral side 814 and angle B measured near the medial side 812 may be different from angle B' measured near the lateral side 814.

Advantageously, the variability and flexibility provided for the design of the resection guide 800 with the angles A, A', B, B', C, and distances D1 and D2 enable an innumerable set of resection guides 800 that can be fabricated. In particular, a unique resection guide 800 can be designed, developed and fabricated for each patient (e.g. patient-specific). The ability of a surgeon and/or technician to predetermine where, and how to orient the proximal slot 824 and/or distal slot 826 provides for an infinite number of different combinations for making a variety of different osteotomies in the bone. Consequently, a surgeon can predetermine which of a first angle (e.g., angle A), a second angle (e.g., angle B), a third angle (e.g., angle C), first distance (e.g., D1), and second distance (e.g., D2) to define or set to achieve a desired type and/or amount of correction for a bone such as a metatarsal. Furthermore, the surgeon can make this predetermination based on medical imaging taken of the patient's foot such that the resection guide 800 is unique to a particular patient. Of course, a surgeon can predetermine two or more of the first angle, second angle, third angle, first distance, and/or second distance as part of preparing for the surgical procedure. In one embodiment, a surgeon may specify aspects of the first angle, second angle, third angle, first distance, and/or second distance in a prescription for the design and/or fabrication of the resection guide 800. Depending on the nature of the correction to be performed a surgeon and/or a technician may define at least one of the first angle, the second angle, the third angle, the first distance, and the second distance to produce one of a uniplanar correction, a biplanar correction, and a triplane correction.

Referring still to FIG. 8I this view illustrates a relationship between the proximal hole 832 and the distal hole 834. In the illustrated embodiment, the proximal hole 832 and the distal hole 834 extend into the body 806 in parallel. This is advantageous because with the holes 832, 834 parallel the resection guide 800 can be readily removed after the osteotom(ies). FIG. 8H illustrates that the proximal hole 832 and distal hole 834 are aligned with each other. Such alignment can also facilitate removal of the resection feature 822 after the osteotom(ies). In addition, alignment of the holes 832, 834 helps to ensure stable engagement with sufficient thicknesses of the metatarsal to secure the resection guide 800 to the metatarsal.

In certain embodiments, the proximal hole 832, distal hole 834 and associated proximal guide pin 836 and distal guide pin 838 may cooperate to prepare for subsequent steps in the surgical procedure. In addition to coupling the body 806 to the bone, the proximal hole 832, distal hole 834 may be strategically positioned in the body to form anchor holes for fixation deployed subsequent to the use of the resection guide 800. For example, suppose a surgeon wants to use bone staples 710b for fixation after the osteotomy. Accordingly, the position of the proximal hole 832 and/or distal hole 834 may be determined to form anchor holes for the legs of the staple 710b. Driving the proximal guide pin 836 and distal guide pin 838 into the proximal hole 832 and distal hole 834 can form holes in the metatarsal that are properly spaced and/or aligned for use with a staple 710b after the osteotomy.

In embodiments where the proximal hole 832 and distal hole 834 cooperate with the proximal guide pin 836 and distal guide pin 838 to form anchor holes, one of the proximal hole 832 and the distal hole 834 may be angled relative to the other hole. The two holes may be angled such that completion of the osteotomy and reduction of the bone fragments transitions holes in the bone from an unusable angle for a staple 710b to an angled or parallel relationship suitable for use with the staple 710b. As an example, in FIG. 8I, distal hole 834 could be angled to match the angle of distal slot 826. If the distal hole 834 has such an angle, a surgeon may need to remove the distal guide pin 838 to remove the resection guide 800. The remaining hole in the bone can be used for the staple 710b. In certain embodiments, a surgeon may replace the distal guide pin 838 after removing the resection guide 800 to use the distal guide pin 838 with a compressor 770 or other instrument as part of the surgical procedure. Of course, the proximal hole 832 and distal hole 834 may be parallel to each other and angles for fixation or compressors may be built into those instruments for that stage of a surgical procedure.

Figure 9:
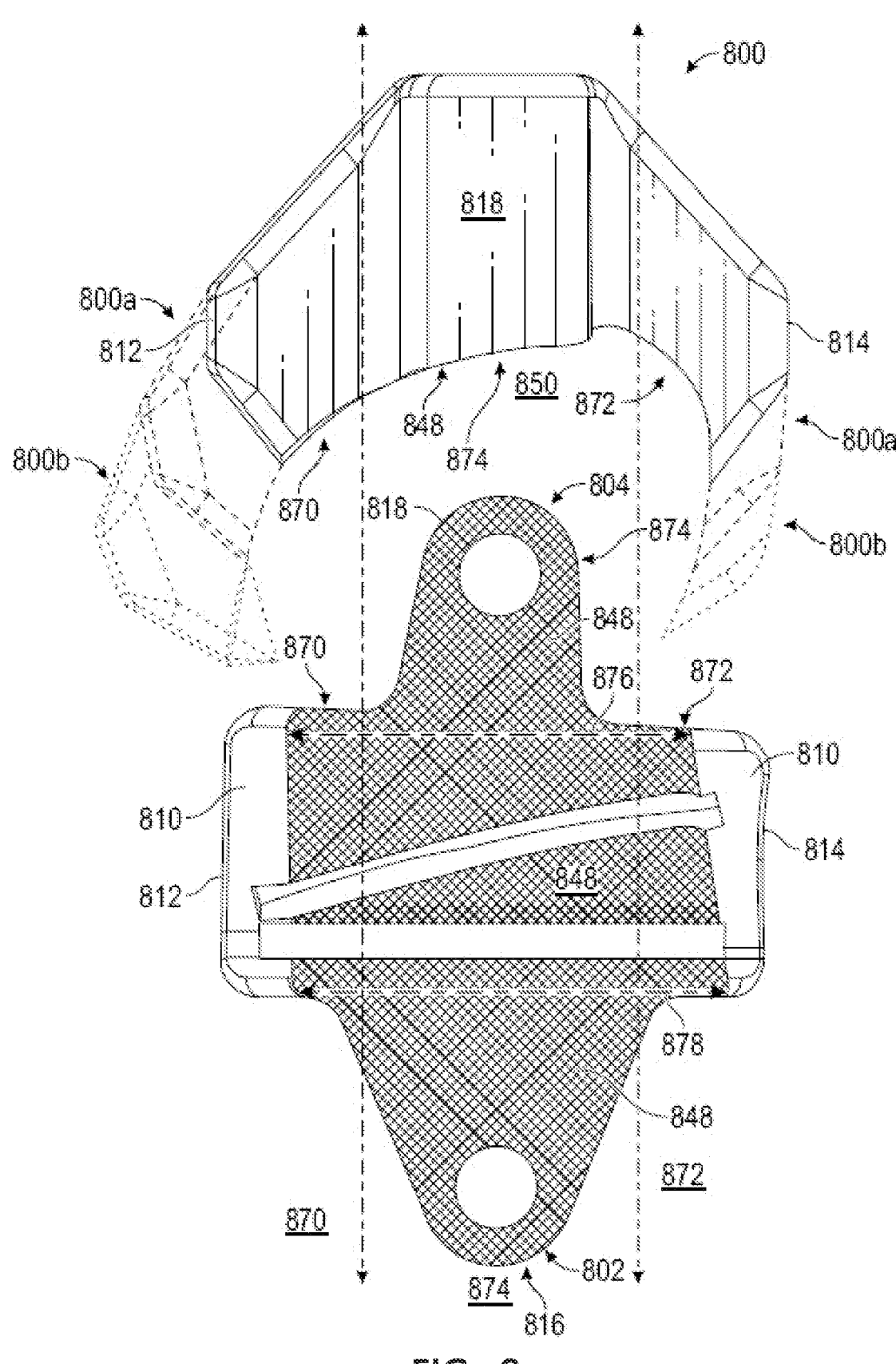
FIG. 9 is a right side or distal view and a bottom or inferior view of an example resection guide illustrating parts of a bone engagement surface according to one embodiment.

FIG. 9 is a right side or distal view and a bottom or inferior view of an example resection guide 800 illustrating parts of a bone engagement surface 848 according to one embodiment. In the distal side view, the bone engagement opening 850 is also illustrated. In the illustrated embodiment, the resection guide 800 is designed for use on a dorsal surface of a metatarsal for a particular patient and may thus be referred to as a dorsal resection guide 800 designed for a lateral closing wedge osteotomy.

FIG. 9 illustrates a distal view aligned with a bottom or inferior view with lead lines that show how parts of one view map, correlate, and/or correspond to the other.

In the illustrated embodiment, the bone engagement surface 848 is divided into three parts: a medial surface 870, a lateral surface 872, and an intermediate surface 874 between the other two surfaces. The medial surface 870 is configured to contact a medial surface of a metatarsal of the patient. In one embodiment, this means that the medial surface 870 includes cavities, protrusions, etc. on the medial surface 870 that correlate with, and will engage, or receive, corresponding protrusions and/or cavities of the medial surface of the metatarsal. The lateral surface 872 is configured to contact a lateral surface of the metatarsal of the patient. In one embodiment, this means that the lateral surface 872 includes cavities, protrusions, etc. on the lateral surface 872 that correlate with, and will engage, or receive, corresponding protrusions and/or cavities of the lateral surface of the metatarsal. The intermediate surface 874 is configured to contact a dorsal surface of a metatarsal of the patient. In one embodiment, this means that the intermediate surface 874 includes cavities, protrusions, etc. on the intermediate surface 874 that correlate with, and will engage, or receive, corresponding protrusions and/or cavities of the dorsal surface of the metatarsal. In one embodiment, the resection guide 800 is configured to contact three surface of the metatarsal, consequently, the bone engagement surface 848 includes three corresponding surfaces.

Those of skill in the art will appreciate that the embodiment of FIG. 9 is but one example of a resection guide 800. In another embodiment, the resection guide is designed to approach and engage a metatarsal from the medial side of the metatarsal. In such an embodiment, the bone engagement surface may include a plantar surface configured to contact a plantar surface of the metatarsal. In one embodiment, this means that the plantar surface includes cavities, protrusions, etc. on the plantar surface that correlate with, and will engage, or receive, corresponding protrusions and/ or cavities of the plantar surface of the metatarsal. Furthermore, the bone engagement surface may include a dorsal surface configured to contact a dorsal surface of the metatarsal. In one embodiment, this means that the dorsal surface includes cavities, protrusions, etc. on the dorsal surface that correlate with, and will engage, or receive, corresponding protrusions and/or cavities of the dorsal surface of the metatarsal. Furthermore, the bone engagement surface may include an intermediate surface between the plantar surface and the dorsal surface and configured to contact a medial surface of the metatarsal. In one embodiment, this means that the intermediate surface includes cavities, protrusions, etc. on the intermediate surface that correlate with, and will engage, or receive, corresponding protrusions and/or cavities of the medial surface of the metatarsal. Such an embodiment may be referred to as a medial dorsal closing wedge resection guide and can be used to form a wedge that includes part of the dorsal surface and converges towards the plantar side of the metatarsal.

The distal view in FIG. 9 also illustrates two alternative embodiment designs (800a and 800b) that a surgeon can request for a surgical procedure, each are shown with the same structure as in resection guide 800 with an extended medial addition on the medial side 812 and an extended lateral addition on the lateral side 814. The extended medial addition and extended lateral addition cause the resection guide 800a to engage more of a circumference of the metatarsal than the resection guide 800. The resection guide 800b includes the extended medial addition and extended lateral addition of the resection guide 800a and add another extended medial addition and another extended lateral addition. Thus, the resection guide 800b engages more of a circumference of the metatarsal than the resection guide 800a. Of course, those of skill in the art will appreciate that the resection guide 800a and/or resection guide 800b may have one or the other of the extended medial addition and extended lateral addition and the sizes of the extended medial addition and extended lateral addition may vary between embodiments. Advantageously, the embodiments of the present disclosure enable a surgeon to predetermine whether they want a resection guide that is like resection guide 800, resection guide 800a, and/or resection guide 800b.

In certain embodiments, a surgeon can dictate or define the configuration of the bone engagement surface 848 which may directly or indirectly impact the size and configuration of the medial side 812 and/or lateral side 814. For example, the surgeon can define how much of a circumference of the metatarsal they want the bone engagement surface 848 to encompass. Furthermore, a surgeon can define a length and width for the bone engagement surface 848 and/or a depth for the bone engagement opening 850. FIG. 9 illustrates a distal width 876 for the bone engagement surface 848 and a proximal width 878 for the bone engagement surface 848. Advantageously, a surgeon can define, alter, or adjust the distal width 876 and/or proximal width 878 to suit their preferences, the needs of the patient, or the like.

By adjusting the distal width 876, proximal width 878 and/or longitudinal length of the bone engagement surface 848 a surgeon can impact how the resection guide 800 seats on the metatarsal during the surgical procedure. In one embodiment, a surgeon may want a loose fit while another surgeon may want a more tight fit. In certain embodiments, the resection guide 800 is configured to engage a metaphyseal diaphyseal junction ("MDJ") of the metatarsal near a base of the metatarsal. Alternatively, or in addition, a surgeon can choose to position the resection guide 800 at another position along a length of the metatarsal or on a particular surface of the metatarsal. Those of skill in the art will appreciate that changing the position of the resection guide 800 can change the makeup and configuration of bone engagement surface 848 because the surface contacting the resection guide 800 will change.

In certain embodiments, a surgeon can setup, define, or specify one or more aspects of the resection guide 800 by completing a prescription for the fabrication of the resection guide 800. In one embodiment, the surgeon may alter predefined configurations or choose a configuration from a set of optional configurations. Alternatively, or in addition, a surgeon may define a resection guide 800 from scratch.

FIG. 9 illustrates embodiments of a resection guide 800 that may enclose a certain amount of the circumference of the metatarsal. In one embodiment, the resection guide 800 may be configured to facilitate engaging the resection guide 800 around the metatarsal (positioning the metatarsal within the bone engagement opening 850). Such a feature may be implemented as part of the bone attachment feature 830, part of the body 806, or the like.

In one embodiment, the body 806 is configured to be pliable. In addition, the medial surface 870 may extend plantarly until the medial surface 870 is opposite a lateral surface 872 that also extends plantarly. In this configuration, a user may couple the resection guide 800 to the metatarsal by driving the intermediate surface 874 towards a dorsal surface of the bone which may cause the medial surface 870 to slide along the metatarsal medial surface and the lateral surface 872 to slide along the metatarsal lateral surface until the intermediate surface 874 engages the metatarsal dorsal surface which results in the medial surface 870 contacting the metatarsal medial surface and the lateral surface 872 contacting the metatarsal lateral surface.

In certain embodiments, having a pliable body 806 driving the intermediate surface 874 towards the dorsal surface may cause the medial surface 870 and/or lateral surface 872 to snap around the metatarsal. The snap action may create an audible and/or tactile signal to a surgeon that the resection guide 800 has been properly positioned. Those of skill in the art will appreciate that there are various ways to make the body 806 pliable including forming the body 806 out of a pliable material such as nylon or PEEK, providing pliable joints in the body 806 (e.g., thinned sections of the body approximately where the dashed lead lines intersect the body 806 of the side view), providing mechanical joints in the body 806, providing elastic joints or sections of the body 806. Each of these techniques for making the body 806 pliable are included within the scope of this disclosure.

Figures 10A, 10B:
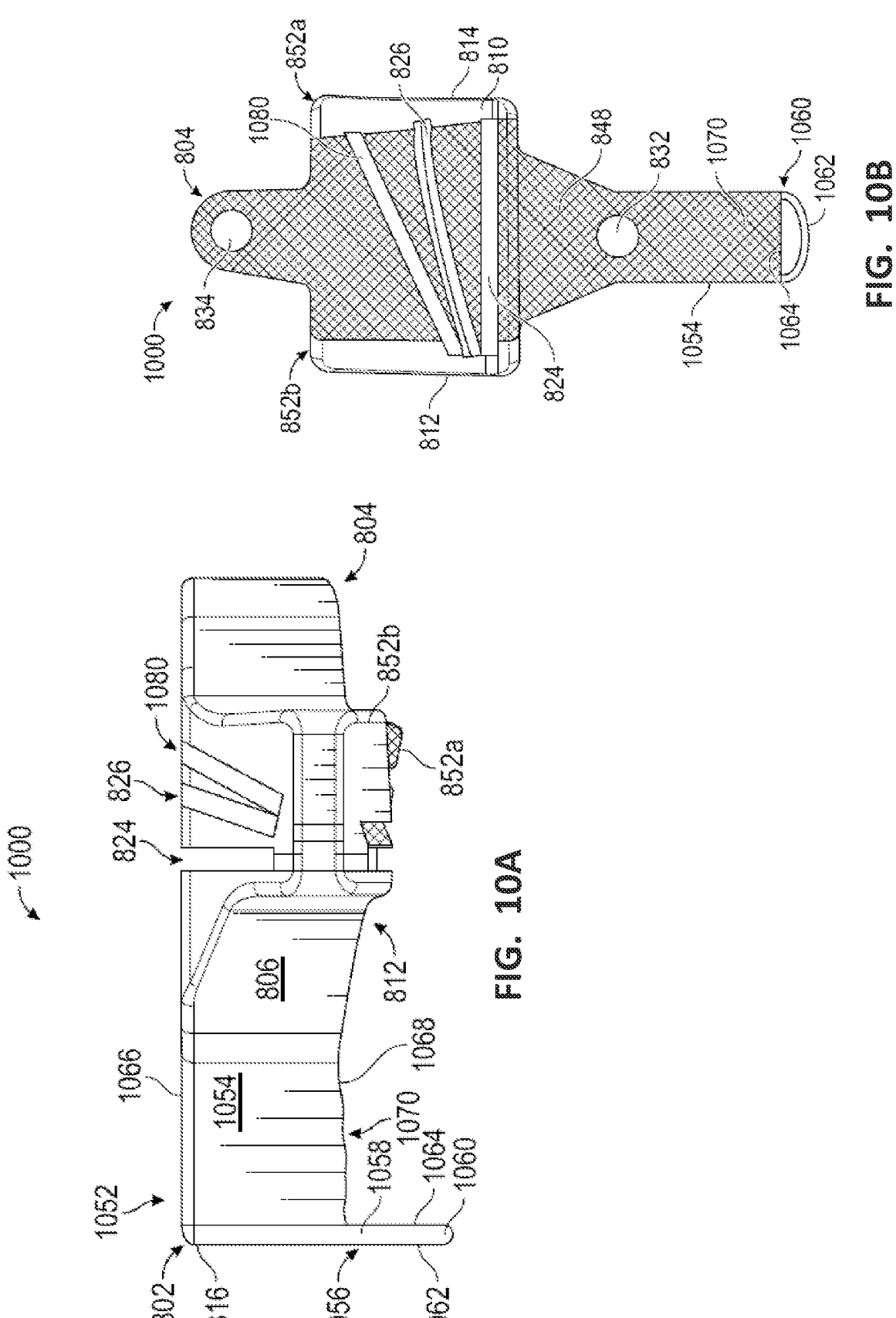
FIG. 10A is a front or medial view of a resection guide according to one embodiment, that includes a probe.
FIG. 10B is a bottom or inferior view of the resection guide of FIG. 10A, that includes a probe.

FIG. 10A is a front or medial view of a resection guide 1000 according to one embodiment, that includes a landmark registration feature 1052. One challenge in performing osteotomies on such small bones as those of a hand or foot, is how to make accurate and precise cuts on such small bones/structures. Embodiments such as the resection guide 1000 and resection guides like this embodiment can be used to help address this challenge.

The resection guide 1000 may have many structures, features, and functions, operations, and configuration similar or identical to those of the resection guide 800 described earlier, like parts are identified with the same reference numerals. However, the resection guide 1000 may include a landmark registration feature 1052 that facilitates positioning the resection guide 1000 in a predetermined position on a bone such as a metatarsal. The landmark registration feature 1052 may be included together with the lateral landmark registration features 852a and/or medial landmark registration features 852b or may be included instead of the lateral landmark registration features 852a and/or medial landmark registration features 852b.

The landmark registration feature 1052 can provide increased accuracy and/or assurance that a surgeon has positioned the resection guide 1000 in a desired location on the bone. Advantageously, the landmark registration feature 1052 is configured to register to a specific landmark on the anatomy of the patient. In the illustrated embodiment, the landmark registration feature 1052 is configured to identify and/or register to a tarso-metatarsal ("TMT") joint that engages with the bone to be resected using the resection guide 1000.

In one embodiment, the landmark registration feature 1052 includes an arm 1054 connected to a probe 1056. The arm 1054 may connect to and/or extend from a proximal side 816 of the body 806. The arm 1054 connects the probe 1056 to the body 806.

The probe 1056 is configured to fit within a TMT joint proximal to the metatarsal that is to be resected. The probe 1056 may include a leg 1058 that connects to an end 1060. The leg 1058 may be thin and/or narrow and of a length that can position the end 1060 between an articular surface of the metatarsal and an articular surface of a tarsal, such as a medial cuneiform. The end 1060 can be thin and may taper to a point to facilitate insertion between bones of the TMT joint. Alternatively, or in addition, the end 1060 can be contoured to match the contour of two articulating surface of the TMT joint when in a resting position. In the illustrated embodiment, the end 1060 is narrowed and smooth on its end.

The leg 1058 has a proximal surface 1062 and a distal surface 1064. In one embodiment, the proximal surface 1062 can be smooth or rounded. Alternatively, or in addition, the proximal surface 1062 is contoured to match a contour of a surface of a tarsal bone that contacts the leg 1058 when the leg 1058 is in the desired position within the TMT joint. In one embodiment, the distal surface 1064 is contoured to match a contour of a surface of the metatarsal bone that contacts the leg 1058 when the leg 1058 is in the desired position within the TMT joint.

FIG. 10B is a bottom or inferior view of the resection guide of FIG. 10A, that includes probe 1056. FIGS. 10A and 10B show the different parts of the landmark registration feature 1052. In the illustrated embodiment, the arm 1054 includes a superior surface 1066 and an inferior surface 1068. In certain embodiments, the inferior surface 1068 is contoured to match a contour of a surface of the metatarsal bone that contacts the inferior surface 1068 when the resection guide 1000 is in the desired position within the TMT joint. In particular, the inferior surface 1068 can include a probe bone engagement surface 1070 configured to register to a part of a surface of the metatarsal between the TMT joint and a neck of the metatarsal.

Alternatively, or in addition, the resection guide 1000 may also include an additional slot 1080. Slot 1080 may be positioned distal to the distal slot 826. In certain embodiments, a surgeon may request that the resection guide include more than one or two slots. Having slot 1080 can give the surgeon another option for the osteotomy intraoperatively. This may permit the surgeon to use any combination of the three slots (e.g., proximal slot 824, distal slot 826, and/or slot 1080) and thus intraoperatively determine the best osteotomy given the anatomy and conditions presented during the surgical procedure. Thus, the proximal slot 824, distal slot 826, and/or slot 1080 can form an alternative resection feature.

Figure 11:
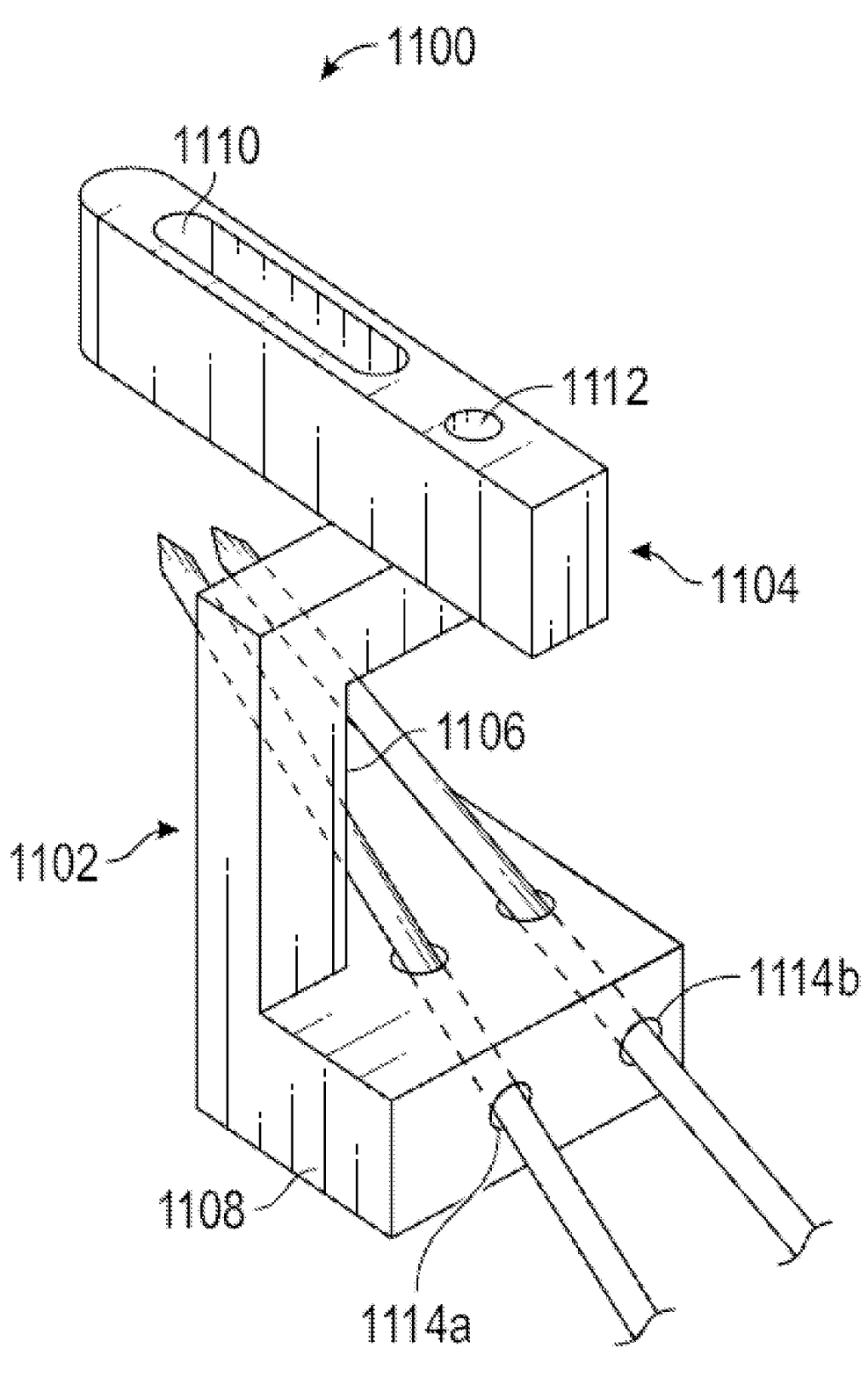
FIG. 11 is a perspective view of a trajectory guide according to one embodiment.

FIG. 11 is a perspective view of a trajectory guide 1100 according to one embodiment. Alternatively, or in addition, the trajectory guide 1100 can be referred to as a jig. The trajectory guide 1100 provides a predetermined orientation and trajectory for deployment of fasteners, such as guide pins, into a first bone and/or a second bone or bone fragment such as a neck of a metatarsal and a base of the metatarsal in order to provide temporary or permanent fixation during a surgical procedure. In certain embodiments, the trajectory guide 1100 is configured to guide one or more fasteners into one or more bones at a patient-specific trajectory. A patient-specific trajectory is a trajectory that may be unique to a particular patient. In this manner, the trajectory guide 1100 may be a patient-specific trajectory guide. The guide pins may serve to guide formation of bone tunnels and/or deployment of temporary or permanent fasteners such as cannulated bone screws. The cannulated screws may be self-tapping and self-drilling.

Advantageously, a user or surgeon can configure the trajectory for the fasteners such that the fasteners will take an optimal angle and/or path through one or more bones, one or more spaces near bones, and/or into one or more bones. Since embodiments of the resection guide can be fabricated based on medical imaging of a patient, the trajectory guide 1100 can also be customized to the particular patient, patient needs, surgeon preferences, and the like and can also be customized to one or more types or brands of hardware fasteners and/or implants that are to be used for the surgical procedure. Alternatively, or in addition, when the trajectory guide 1100 is designed and is in the form of a model, a user and/or surgeon can define, refine, adjust, and/or modify the trajectory provided by the trajectory guide 1100 such that an optimal placement of temporary and/or permanent fasteners is achieved.

The trajectory guide 1100 can be configured to engage with fasteners used in other stages of a surgical procedure. For example, the trajectory guide 1100 may engage a proximal guide pin 836 and a distal guide pin 838. In the illustrated embodiment, the trajectory guide 1100 includes a body 1102 and the body 1102 includes a head 1104, a neck 1106, and a base 1108.

The head 1104 is configured to couple to instrumentation secured to bones of a patient. In the illustrated embodiment, the head 1104 includes a proximal opening 1110 and a distal opening 1112. The proximal opening 1110 is configured to receive a proximal guide pin 836 that is deployed into a metatarsal. In the illustrated embodiment, the proximal opening 1110 is a slot that can facilitate engagement with the proximal opening 1110. The distal opening 1112 is configured to receive a distal guide pin 838 that is deployed into the metatarsal. By engaging the proximal guide pin 836 and/or distal guide pin 838, the trajectory guide 1100 is secured and stable within the operating field.

The neck 1106 connects the head 1104 to the base 1108. The neck 1106 can have a variety of configurations. In the illustrated embodiment, the neck 1106 is a slender structure connecting the head 1104 and the base 1108.

The base 1108 connects to the neck 1106 and includes at least one fastener opening 1114. The at least one fastener opening 1114 is configured to receive a fastener that is to be deployed into a bone fragment of the patient. In the illustrated embodiment, the base 1108 includes two fastener openings 1114. The diameter of the at least one fastener opening 1114 may be large enough to receive a desired fastener a surgeon would like to use for fixation. The at least one fastener opening 1114 extends through the base 1108 at an angle relative to the bone fragment(s) such that an inserted fastener will have the desired trajectory into the bone fragment(s). In one embodiment, the trajectory and at least one fastener opening 1114 may be configured to allow the at least one fastener opening 1114 to secure a distal bone fragment on one side of an osteotomy formed by a metatarsal base resection guide 720, 800 to a proximal bone fragment on an opposite side of the osteotomy.

In one embodiment, the trajectory is predefined to direct an at least one fastener opening 1114 from medial distal to medial proximal or lateral proximal into the metatarsal and across the cut faces formed by the osteotomy and engage a proximal bone fragment. While the illustrated embodiment illustrates deployment of the at least one fastener opening 1114 retrograde (or from distal to proximal), those of skill in the art will appreciate that the trajectory guide 1100 can also be configured to direct the at least one fastener opening 1114 antegrade (or from proximal to distal) and/or at any desired angle relative to the bone fragment(s).

FIG. 12 is a flowchart diagram depicting a method for remediating a condition, according to one embodiment. FIG. 12 is a flowchart of an example method 1200. In some implementations, one or more method steps of FIG. 12 may be performed by a user using instrumentation of the present disclosure.

As shown in FIG. 12, method 1200 may include deploying a metatarsal base resection guide onto a metatarsal near a neck, or body, of the metatarsal. The metatarsal base resection guide includes: a body having a proximal end and a distal end and having a superior side, an inferior side, a medial side, a lateral side, a proximal side, and a distal side; a resection feature between the proximal end and the distal end that guides resection of a metatarsal of a patient's foot; a bone attachment feature configured to couple the body to the metatarsal; and a bone engagement surface configured to register to the metatarsal based on medical imaging taken of the patient's foot (block 1202).

As also shown in FIG. 12, method 1200 may include translating the metatarsal base resection guide along the metatarsal towards a base of the metatarsal until a medial surface of the bone engagement surface engages a medial surface of the metatarsal, a lateral surface of the bone engagement surface engages a lateral surface of the metatarsal, and an intermediate surface of the bone engagement surface between the medial surface and the lateral surface form a substantially a friction fit between the medial surface, dorsal surface, and lateral surface of the metatarsal and the metatarsal base resection guide (block 1204).

As further shown in FIG. 12, method 1200 may include deploying a proximal guide pin and a distal pin guide into the bone attachment feature (block 1206).

As also shown in FIG. 12, method 1200 may include deploying a cutting tool into the resection feature of the metatarsal base resection guide to form an osteotomy of the metatarsal (block 1208).

In one embodiment, the method 1200 may further include removing the metatarsal base resection guide from the metatarsal while leaving proximal guide pin and distal guide pin in place (block 1210).

As also shown in FIG. 12, method 1200 may include deploying a positioning guide configured to join two cut faces formed by the osteotomy and reduce bone fragments formed by the osteotomy (block 1212).

As further shown in FIG. 12, method 1200 may include deploying fixation to secure the reduced bone fragments of the osteotomy (block 1214). Method 1200 may include additional implementations, such as any single implementation or any combination of implementations described below and/or in connection with one or more other methods or processes described elsewhere herein. In a first implementation, the metatarsal base resection guide may include a landmark registration feature and translating the metatarsal base resection guide along the metatarsal further may include translating the metatarsal base resection guide until a probe of the landmark registration feature seats within a tarso-metatarsal (TMT) joint that includes the metatarsal. In one embodiment, the metatarsal base resection guide may include a landmark registration feature and the translating step of method 1200 may include translating the metatarsal base resection guide until a probe of the landmark registration feature seats within a tarso-metatarsal ("TMT") joint that includes the metatarsal.

Although FIG. 12 shows example blocks or steps of a process 1200, in some implementations, A method 1200 may include additional steps, fewer steps, different steps, or differently arranged steps than those depicted in FIG. 12. Additionally, or alternatively, two or more of the steps of a method 1200 may be performed in parallel.

FIGS. 13A-13F illustrate different views of one or more stages in a surgical procedure that includes one or more embodiments of the present disclosure. Reference is made to FIGS. 13A-13F and FIG. 12. In the illustrated embodiment, the metatarsal is a patient's first metatarsal 208.

Figures 13A, 13B, 13C, 13D, 13E, 13F:
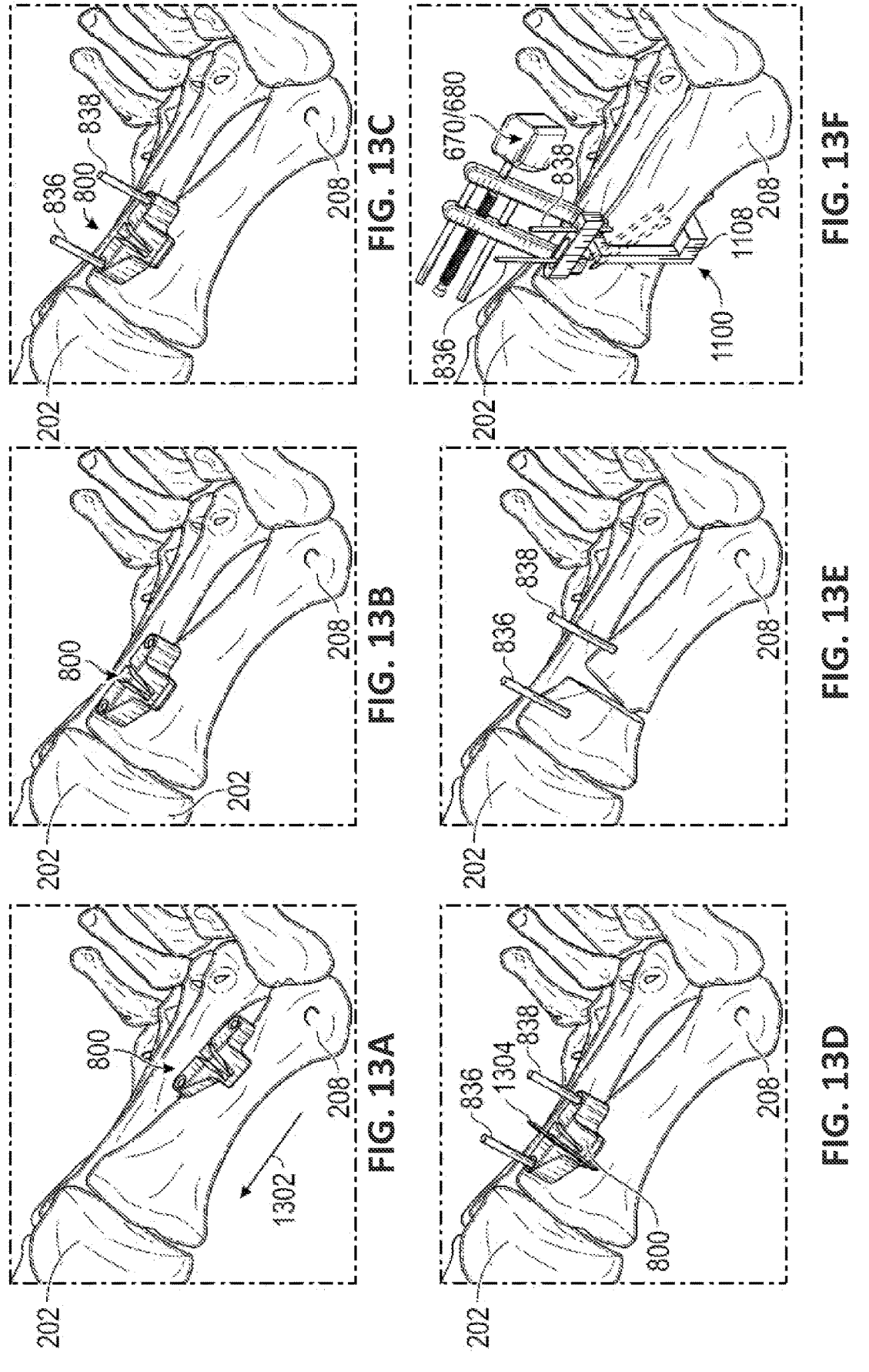
FIGS. 13A-13F illustrate different views of one or more stages in a surgical procedure that includes one or more embodiments of the present disclosure.

FIG. 13A illustrates a stage of the method 1200 in which a resection guide 800, such as a metatarsal base resection guide 720, is deployed onto a metatarsal near a neck of the metatarsal. In the illustrated embodiment, the surgeon has made an incision that permits placement on the neck and near the head. However, in other embodiments, a surgeon may make the incision smaller and initially position the resection guide 800 closer to the base. Advantageously, the initial placement and configuration of the medial surface 870, lateral surface 872 and/or intermediate surface 874 may mean that the resection guide 800 sits loose on the dorsal surface of the first metatarsal 208. Next, a surgeon may translate the resection guide 800 toward the base in the direction of arrow 1302.

FIG. 13B illustrates a stage in the surgical procedure in which the resection guide 800 has been translated into a desired position near the base, near the MDJ junction, and/or at the MDJ junction. Once the resection guide 800 is in place a surgeon can operate the bone attachment feature 830 to couple the resection guide 800 to the bone. Before doing so, a surgeon may use fluoroscopy to check the position of the resection guide 800 relative to the parts of the bone.

In one embodiment, FIG. 13C illustrates the resection guide 800 as method step 1206 is completed. A user has deployed a proximal guide pin 836 in the proximal hole 832 and a distal guide pin 838 in the distal hole 834. The initial and accurate positioning of the proximal guide pin 836 and/or distal guide pin 838 can be an important step in a surgical procedure because other steps and/or instruments may rely on accurate positioning of these pins 836, 838 to perform their respective desired functions and aspects.

The resection guide 800 is now stable and temporarily fixed to the metatarsal. A surgeon can now proceed with the osteotomy with confidence that the cuts made using the resection feature 822 will result in the angles, trajectories, and desired cuts of the metatarsal to provide the preplanned and desired correction, which have been based on the medical imaging of the patient's foot.

In one embodiment, FIG. 13D illustrates the resection guide 800 and first metatarsal 208 as method step 1208 is performed. When secured as illustrated in FIGS. 13C, 13D, a user may operate the resection guide 800 by inserting a cutting tool such as a rectangular oscillating blade 1304 attached to a manual, mechanical, pneumatic, or electric driver into proximal slot 824 and distal slot 826. Next, with the rectangular oscillating blade 1304 oscillating, the user may cut into the metatarsal and, in this embodiment, form two cut faces. As noted above, the osteotomy may form a wedge for a closing wedge osteotomy, form a wedge for a closing wedge osteotomy that preserves bone on one side of the bone to serve as a living hinge, and/or make clean cuts through both sides of the bone.

In certain embodiments, the proximal slot 824 and distal slot 826 are larger than a distal end of the rectangular oscillating blade. Consequently, in the illustrated embodiment, a user can pivot the rectangular oscillating blade 1304 such that a non-cutting end of the rectangular oscillating blade 1304 is directed dorsally, in relation to the bone, as the rectangular oscillating blade 1304 aims and moves dorsally, the rectangular oscillating blade 1304 cuts the bone towards the plantar surface of the bone (the angled medial inferior surface 856 and lateral inferior surface 862 facilitate this pivoting). Similarly, the user can pivot the rectangular oscillating blade 1304 such that the non-cutting end of the rectangular oscillating blade 1304 is directed plantarly, in relation to the bone, as the rectangular oscillating blade 1304 aims and moves plantarly, the rectangular oscillating blade 1304 cuts the bone towards the dorsal surface of the bone. In this manner, a user can resection a bone with a minimal size opening to the bone.

FIG. 13E illustrates the first metatarsal 208 after the osteotom(ies) and after method step 1210 is performed. The resection guide 800 has been removed and the proximal guide pin 836 and distal guide pin 838 remain in place. Removal of the proximal guide pin 836 and distal guide pin 838 has been facilitated by the proximal hole 832 and distal hole 834 being aligned and the proximal guide pin 836 and distal guide pin 838 being parallel to each other, in the illustrated embodiment.

The cuts are visible and a proximal cut face on a proximal end of the first metatarsal 208 is formed and a distal cut face on a more distal part of the first metatarsal 208. In one embodiment, the proximal cut face on the proximal end of the first metatarsal 208 can serve as a point or plane of reference for measuring where to position the proximal hole 832 and distal hole 834 and corresponding proximal guide pin 836 and distal guide pin 838. In one embodiment, a corresponding cut face on a bone model of a patient's first metatarsal 208 may be used to calculate measurements for the position of the proximal the proximal hole 832 and distal hole 834 and corresponding proximal guide pin 836 and distal guide pin 838. Advantageously, because the surgical procedure is preplanned it is known what kind of cutting tool will be used. Similarly, it is known what the width of the gap formed by the osteotomy will be. Consequently, a user may design one or more of the instruments to account for the width of this gap and/or to provide compression when closing this gap. Depending on the cutting tool used the width of the gap may be about 1 mm to about 1.5 mm.

FIG. 13F illustrates the first metatarsal 208 after the osteotom(ies) and after method step 1212 is performed. A user has deployed a positioning guide 680 to position the bone fragments and/or reduce the bone fragments. Alternatively, or in addition, the positioning guide 680, in the illustrated embodiment, also functions as a compression guide 670. The proximal cut face and the distal cut face are joined and the first metatarsal 208 takes on a desired corrected orientation. The surgeon has slipped the positioning guide 680 over the proximal guide pin 836 and distal guide pin 838. This action can cause the bone fragments to move into the desired (preplanned) position. Typically, this means that the proximal cut face abuts the distal cut face.

Alternatively, or in addition, the position of proximal guide pin 836 and distal guide pin 838 may result in the two cut faces being compressed together. Alternatively, or in addition, a user can operate the positioning guide 680/compression guide 670 and compress the cut faces together. As this stage the cut faces are joined and the bone fragment reduced. A surgeon can now proceed to deploy fixation with assurance that the reduction will remain in place.

FIG. 13F also illustrates a trajectory guide 1100 deployed for providing fixation. In the illustrated embodiment, the trajectory guide 1100 is slipped over the proximal guide pin 836 and distal guide pin 838 and can sit on top of the positioning guide 680/compression guide 670. Sliding the trajectory guide 1100 into the illustrated position positions the base 1108 plantar to the plantar surface of the first metatarsal 208.

With the trajectory guide 1100 in position the fastener openings 1114 align with the first metatarsal 208 and provide a trajectory for deployment of fasteners such as guide pins 710a and/or bone screws 710c. Those of skill in the art will appreciate that convention methods of fixation can be used after the stage illustrated in FIG. 13F and that method step 1214 is understood and thus an illustration is not needed. Advantageously, the ability in the embodiments of present disclosure to plan the steps, instrumentation, and/or implants of the surgical procedure enable a surgeon to also choose which fixation hardware to use, what size hardware to use, and various other aspects of the hardware because the surgical plan was put together using medical imaging of the patient's foot.

Those of skill in the art will appreciate that the osteotomy system 700 can be used on humans and animals and on bones that are relatively small in comparison to other bones of the body (e.g., bones of the foot and hand). Advantageously, the osteotomy system 700 seeks to minimize the number of fasteners or pins placed within the bones of a patient by planning a surgical procedure such that pins or fasteners placed in one stage are and/or can be reused in subsequent stages. Consequently, pins that hold the resection guide 720 in place for the osteotomy can remain in the bone or bone fragment as instruments are deployed and/or subsequent stages of the surgical procedure are performed. For example, in one embodiment, a proximal guide pin 836 and distal guide pin 838 used for the osteotomy and with the resection guide 720 can be reused by one or more of the complementary components 630 of the osteotomy system 700.

Advantageously, because the present disclosure uses a bone model of the patient's bones and, in certain embodiments, can include a model of the patient's skin in this part of the body, the sizes, dimensions, lengths and configurations of the 720, proximal hole 832, distal hole 834, proximal slot 824, distal slot 826, and the like can each be changed, adapted, revised, and/or customized to meet the needs and/or preferences of the patient and/or surgeon.

Advantageously, using the apparatus, systems, and/or methods of the present disclosure the surgeon may have a preoperative plan that identifies which specific bone screw (length, width, diameter, thread, pitch, etc.) to use for the fasteners. For example, the bone screws 710c may have a tapered proximal end so that the proximal end will be substantially flush with the cortex. Alternatively, or in addition, the bone screws 710c may include external threads, may be self-tapping, and may have a distal end that enables the bone screws 710c to be self-drilling. The bone screws 710c may be implants that serve as permanent fixation for the first metatarsal 208.

Advantageously, the present disclosure provides an apparatus, system, and/or method that can remediate a condition in a patient's foot. Those of skill in the art will appreciate that the methods, processes, apparatuses, systems, devices, and/or instruments of the present disclosure can be used to address a variety of conditions in a variety of procedures and/or parts of the body of the patient. The present disclosure can provide a system 700 that may include a plurality of metatarsal base resection guides 720 that each have differences in the trajectories or angles for the osteotomy and/or an amount of translation provided between the two bone fragments.

Conventionally, correction methods, systems, and/or instrumentation for a condition such as, for example, a bunion and/or a hallux valgus, face several challenges. One example is how to cut the bone such that the cut faces have a desired angle in relation to each other. Another example is how to confirm that the metatarsal base resection guide 720 is in a predetermined position on the first metatarsal 208, a position that is identified in a model formed based on medical imaging of the patient. Advantageously, the present disclosure can address many, if not all, of these challenges to assist a surgeon in performing the surgical procedure and improve the quality of patient care and outcomes.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. An apparatus for remediating a condition present in a patient's foot, the apparatus comprising:
   a proximal end;
   a distal end;
   a body having a superior side, an inferior side, a medial side, a lateral side, a proximal side, and a distal side;
   a resection feature between the proximal end and the distal end that guides resection of a metatarsal of a patient's foot;
   a bone attachment feature configured to couple the body to the metatarsal; and
   a bone engagement surface configured to register to a metaphyseal diaphyseal junction ("MDJ") of the metatarsal near a base of the metatarsal, the bone engagement surface based on medical imaging taken of the patient's foot.

2. The apparatus of claim 1, wherein the bone engagement surface comprises:
   a medial surface configured to contact a medial surface of the metatarsal;
   a lateral surface configured to contact a lateral surface of the metatarsal; and
   an intermediate surface between the medial surface and the lateral surface, the intermediate surface configured to contact a dorsal surface of the metatarsal.

3. The apparatus of claim 2, wherein the body is configured to be pliable and the medial surface extends opposite the lateral surface such that deployment of the apparatus by driving the intermediate surface towards the dorsal surface causes the medial surface to slide along the metatarsal medial surface and the lateral surface to slide along metatarsal lateral surface until the intermediate surface engages the metatarsal dorsal surface which results in the medial surface contacting the metatarsal medial surface and the lateral surface contacting the metatarsal lateral surface.

4. The apparatus of claim 1, wherein the bone engagement surface comprises:
   a plantar surface configured to contact a plantar surface of the metatarsal;
   a dorsal surface configured to contact a dorsal surface of the metatarsal; and
   an intermediate surface between the plantar surface and the dorsal surface, the intermediate surface configured to contact a medial surface of the metatarsal.

5. The apparatus of claim 1, wherein a configuration of the bone engagement surface is defined based on a prescription from a doctor.

6. The apparatus of claim 1, wherein the body comprises a long axis and the resection feature comprises:
   a proximal slot that extends from the superior side to the inferior side at a first angle relative to the long axis, the proximal slot having a first medial end and a first lateral end;
   a distal slot that extends from the superior side to the inferior side at a second angle relative to the long axis, the distal slot having a second medial end and a second lateral end; and
   wherein the first medial end and the second medial end are separated by a first distance and the first lateral end and the second lateral end are separated by a second distance.

7. The apparatus of claim 6, wherein the first distance and the second distance are substantially the same.

8. The apparatus of claim 6, wherein the first distance is shorter than the second distance.

9. The apparatus of claim 8, wherein the first distance is substantially zero such that the proximal slot and distal slot connect at the first medial end and the second medial end and the proximal slot and distal slot are offset by a third angle measured within the transverse plane.

10. The apparatus of claim 9, wherein one of the first angle, the second angle, the third angle, the first distance, and the second distance are predetermined by a surgeon based on the medical imaging taken of the patient's foot.

11. The apparatus of claim 6, wherein the first medial end of the proximal slot and the first medial end of the distal slot are offset by a third angle measured within the transverse plane and wherein at least one of the first angle, the second angle, the third angle, the first distance, and the second distance are defined for a correction consisting of a uniplanar correction, a biplanar correction, and a triplane correction.

12. The apparatus of claim 1, wherein the medial side of the body comprises a medial inferior surface that meets the superior side at a medial edge, the medial inferior surface angled to connect the inferior side of the body and the medial edge such that the medial inferior surface provides clearance for a cutting tool inserted into the resection feature.

13. The apparatus of claim 1, wherein the bone attachment feature comprises:

a proximal hole that extends from the superior side to the inferior side of the body, the proximal hole configured to receive a proximal guide pin;

a distal hole that extends from the superior side to the inferior side of the body, distal hole configured to receive a distal guide pin; and wherein the proximal hole extends into the body parallel and aligned with the distal hole.

14. The apparatus of claim 13, wherein proximal hole and distal hole are configured to cooperate with the proximal guide pin and the distal guide pine to form anchor holes in the metatarsal for fixation deployed subsequent to use of the apparatus.

15. The apparatus of claim 1, wherein the body comprises a landmark registration feature that extends from the proximal side, the landmark registration feature comprising a probe configured to fit within a tarso-metatarsal ("TMT") joint that includes the metatarsal.

16. The apparatus of claim 15, wherein the landmark registration feature comprises a probe bone engagement surface configured to register to a part of a surface of the metatarsal between the TMT joint and a neck of the metatarsal.

17. A system for remediating a condition present in a patient's foot, the system comprising:

a metatarsal base resection guide comprising:

a proximal end;

a distal end;

a body having a superior side, an inferior side, a medial side, a lateral side, a proximal side, and a distal side;

a proximal slot that extends from the superior side to the inferior side at a first angle relative to a long axis of a metatarsal of a patient's foot, the proximal slot having a first medial end and a first lateral end, the proximal slot configured to guide resection of the metatarsal;

a distal slot that extends from the superior side to the inferior side at a second angle relative to the long axis, the distal slot having a second medial end and a second lateral end, the distal slot configured to guide resection of the metatarsal;

a landmark registration feature that extends from the proximal side of the body, the landmark registration feature comprising a probe bone engagement surface;

a proximal hole that extends from the superior side to the inferior side of the body, the proximal hole configured to receive a proximal guide pin that cooperates with the proximal hole to secure the body to the metatarsal;

a distal hole that extends from the superior side to the inferior side of the body, distal hole configured to receive a distal guide pin that cooperates with the distal hole to secure the body to the metatarsal; and a bone engagement opening that includes a bone engagement surface configured to register to a metaphyseal diaphyseal junction ("MDJ") of the metatarsal near a base of a surface of the metatarsal, the bone engagement surface based on medical imaging taken of the patient's foot; and a trajectory guide comprising:

a body comprising:

a head comprising:

a proximal opening configured to receive the proximal guide pin deployed into the metatarsal;

a distal opening configured to receive the distal guide pin deployed into the metatarsal;

a neck connected to the head; and a base connected to the neck, the base comprising:

at least one fastener opening configured to accept a fastener configured to secure a distal bone fragment on one side of an osteotomy formed using the metatarsal base resection guide to a proximal bone fragment on an opposite side of the osteotomy.

18. A method for remediating a condition present in a patient's foot, the method comprising:

deploying a metatarsal base resection guide onto a metatarsal near a neck or body of the metatarsal, the metatarsal base resection guide comprising:

a body a proximal end and a distal end and having a superior side, an inferior side, a medial side, a lateral side, a proximal side, and a distal side;

a resection feature between the proximal end and the distal end that guides resection of a metatarsal of a patient's foot;

a bone attachment feature configured to couple the body to the metatarsal; and a bone engagement surface configured to register to a metaphyseal diaphyseal junction ("MDJ") of the metatarsal near a base of the metatarsal, the bone engagement surface based on medical imaging taken of the patient's foot;

translating the metatarsal base resection guide along the metatarsal towards a base of the metatarsal until a medial surface of the bone engagement surface engages a medial surface of the metatarsal, a lateral surface of the bone engagement surface engages a lateral surface of the metatarsal, and an intermediate surface of the bone engagement surface between the medial surface and the lateral surface form a friction fit between the medial surface, dorsal surface, and lateral surface of the metatarsal and the metatarsal base resection guide;

deploying a proximal guide pin and a distal pin guide into the bone attachment feature;

deploying a cutting tool into the resection feature of the metatarsal base resection guide to form an osteotomy of the metatarsal;

removing the metatarsal base resection guide from the metatarsal while leaving proximal guide pin and distal guide pin in place;

deploying a positioning guide configured to join two cut faces formed by the osteotomy and reduce bone fragments formed by the osteotomy; and deploying fixation to secure the reduced bone fragments of the osteotomy.

19. The method of claim 18, wherein the metatarsal base resection guide comprises a landmark registration feature and translating the metatarsal base resection guide along the metatarsal further comprises translating the metatarsal base resection guide until a probe of the landmark registration feature seats within a tarso-metatarsal ("TMT") joint that includes the metatarsal.

\* \* \* \* \*